US008679504B2

US 008679504 B2

(12) United States Patent
Sellers et al.

(10) Patent No.: US 8,679,504 B2
(45) Date of Patent: Mar. 25, 2014

(54) POULTRY VIRAL MATERIALS AND METHODS RELATED THERETO

(75) Inventors: Holly S. Sellers, Bishop, GA (US); Mark Jackwood, Watkinsville, GA (US)

(73) Assignee: University of Georgia Research Foundation Inc., Athens, GA (US)

( * ) Notice: Subject to any disclaimer, the term of this patent is extended or adjusted under 35 U.S.C. 154(b) by 433 days.

(21) Appl. No.: 12/951,352

(22) Filed: Nov. 22, 2010

(65) Prior Publication Data

US 2011/0097353 A1 Apr. 28, 2011
US 2012/0039921 A9 Feb. 16, 2012

Related U.S. Application Data

(63) Continuation-in-part of application No. PCT/US2009/044818, filed on Mar. 21, 2009.

(60) Provisional application No. 61/055,158, filed on May 22, 2008, provisional application No. 61/308,382, filed on Feb. 26, 2010.

(51) Int. Cl.
*A61K 39/00* (2006.01)
(52) U.S. Cl.
USPC .............................. 424/184.1; 530/350; 435/5
(58) Field of Classification Search
None
See application file for complete search history.

(56) References Cited

U.S. PATENT DOCUMENTS

| | | | |
|---|---|---|---|
| 6,214,538 | B1 | 4/2001 | Jackwood et al. |
| 7,291,342 | B2 | 11/2007 | Melson et al. |
| 2002/0160357 | A1 | 10/2002 | Jackwood et al. |

OTHER PUBLICATIONS

GenBank: GU437870.1. Infectious bronchitis virus isolate GPL9131 S1 glycoprotein gene, partial cds. (2010).*
Jackwood et al., "Rapid heat-treatment attenuation of infectious bronchitis virus," Jun. 2010 *Avian Pathology* 39(3):227-233. Available online on Jun. 11, 2010.
National Center for Biotechnology Information, National Library of Medicine, National Institutes of Health. GenBank Locus GU301925, Accession No. GU301925, Version GU301925.1 GI:307751095. "Infectious bronchitis virus isolate Georgia 08 S1 protein (S1) gene, partial cds," [online]. Bethesda, MD [retrieved on Nov. 16, 2010]. Retrieved from the Internet: <http://www.ncbi.nlm.nih.gov/nuccore/307751095>; 2 pgs., 2010.
National Center for Biotechnology Information, National Library of Medicine, National Institutes of Health. GenBank Locus GU360617, Accession No. GU360617, Version GU360617.1 GI:295154994. "*Tragus berteronianus* voucher US:Peterson 21615, Soreng, La Torre & Rojas Fox ribosomal protein S16 (rps16) gene, exon 2 and partial cds; and rps16-trnK intergenic spacer, partial sequence; chloroplast," [online]. Bethesda, MD [retrieved Nov. 16, 2010]. Retrieved from the Internet: < http://www.ncbi.nlm.nih.gov/nuccore/295154994>; 1 pg., 2010.
National Center for Biotechnology Information, National Library of Medicine, National Institutes of Health. GenBank Locus GU361606, Accession No. GU361606, Version GU361606.1 GI:291278205. "Infectious bronchitis virus isolate GA08/GA08pass4/08 spike glycoprotein gene, partial cds," [online]. Bethesda, MD [retrieved on Nov. 11, 2010]. Retrieved from the Internet: <http://www.ncbi.nlm.nih.gov/nuccore/291278205>; 1 pg., 2010.
National Center for Biotechnology Information, National Library of Medicine, National Institutes of Health. GenBank Locus GU361607, Accession No. GU361607, Version GU361607.1 GI:291278207. "Infectious bronchitis virus isolate GA08/GA08HSp16/08 Heat-treatment Attenuated spike glycoprotein (S1) gene, complete cds," [online]. Bethesda, MD [retrieved on Nov. 16, 2010]. Retrieved from the Internet: <http://www.ncbi.nlm.nih.gov/nuccore/GU361607.1>; 2 pgs., 2010.
National Center for Biotechnology Information, National Library of Medicine, National Institutes of Health. GenBank Locus GU734804, Accession No. GU734804, Version GU734804.1 GI:293411061. "Infectious bronchitis virus isolate GA08-GA08-08_pass16 spike glycoprotein (S1) gene, partial cds," [online]. Bethesda, MD [retrieved on Nov. 16, 2010]. Retrieved from the Internet: <http://www.ncbi.nlm.nih.gov/nuccore/293411061>; 2 pgs., 2010.
Sellers et al., "Recent isolation and characterization of nephrotic and variant infectious bronchitis isolates from Georgia," Mar./Apr. 2008 *The Poultry Informed Professional* Issue 98; 7 pages.
Zou et al., "The expression and characterization of highly antigenic region of spike protein of prevalent infectious bronchitis virus in *Escherichia coli*," 2010 *J. Anim. Vet. Adv.* 9(8):1267-1274.

* cited by examiner

*Primary Examiner* — Michelle S Horning
(74) *Attorney, Agent, or Firm* — Mueting Raasch & Gebhardt, P.A.

(57) ABSTRACT

The present invention provides materials and methods for researching poultry viruses, particularly for researching infectious bronchitis viruses in poultry. Also provided are materials and methods useful for reducing the economic impact that infectious bronchitis disease has on poultry production. In one aspect of the invention, there are provided nucleic acids, amino acids and related materials and compositions useful for combating infectious bronchitis virus in poultry.

25 Claims, 13 Drawing Sheets

*Figure 1*

| |
|---|
| *Figure 1ₐ* |
| *Figure 1ᵦ* |

Figure 1a

```
att tct agt tta gtt aag gaa aag ttt att gtt tat cgt gag aat agt        48
Ile Ser Ser Leu Val Lys Glu Lys Phe Ile Val Tyr Arg Glu Asn Ser
1               5                   10                  15 att aat acc act ttg gtt tta cat aat ttt acg ttt cat aat gaa agc        96
Ile Asn Thr Thr Leu Val Leu His Asn Phe Thr Phe His Asn Glu Ser
                20                  25                  30 aat gca caa cct aat ctt ggt ggt gtt aat aac att gct att tat caa       144
Asn Ala Gln Pro Asn Leu Gly Gly Val Asn Asn Ile Ala Ile Tyr Gln
            35                  40                  45 aca caa aca gct cag agt ggc tat tat aat ttt aat ttc tca ttt ctg       192
Thr Gln Thr Ala Gln Ser Gly Tyr Tyr Asn Phe Asn Phe Ser Phe Leu
        50                  55                  60 agt agt ttt gtt tat aag tca agt gat ttt atg tat ggg tct ttt cac       240
Ser Ser Phe Val Tyr Lys Ser Ser Asp Phe Met Tyr Gly Ser Phe His
65                  70                  75                  80 cca cag tgt agt ttt aaa cca gaa aac att aat aat ggg ctc tgg ttc       288
Pro Gln Cys Ser Phe Lys Pro Glu Asn Ile Asn Asn Gly Leu Trp Phe
                85                  90                  95 aat tca ctt tca att tca ctt gct tac ggc cca cta caa ggg ggc tgt       336
Asn Ser Leu Ser Ile Ser Leu Ala Tyr Gly Pro Leu Gln Gly Gly Cys
            100                 105                 110 aaa cag tca gtt ttt agt cgc aaa aca acg tgt tgt tat gct tat tca       384
Lys Gln Ser Val Phe Ser Arg Lys Thr Thr Cys Cys Tyr Ala Tyr Ser
        115                 120                 125 tat ggc ggt cct cat ttg tgt aaa ggt gtt tat gca ggt gag tta aca       432
Tyr Gly Gly Pro His Leu Cys Lys Gly Val Tyr Ala Gly Glu Leu Thr
    130                 135                 140 aag aat ttt gaa tgt ggc ttg tta gtt tat att act aag agt gat ggt       480
Lys Asn Phe Glu Cys Gly Leu Leu Val Tyr Ile Thr Lys Ser Asp Gly
145                 150                 155                 160 tct cgt ata caa acg gca aca gaa gca cct gta gta acc aca aat ttt       528
Ser Arg Ile Gln Thr Ala Thr Glu Ala Pro Val Val Thr Thr Asn Phe
                165                 170                 175
```

```
tac aat aac att act ttg aat aag tgt gtt gag tat aat ata tac ggt      576
Tyr Asn Asn Ile Thr Leu Asn Lys Cys Val Glu Tyr Asn Ile Tyr Gly
            180                 185                 190 aga att ggc caa ggt ttt att act aat gta act gat tta gct tct agt      624
Arg Ile Gly Gln Gly Phe Ile Thr Asn Val Thr Asp Leu Ala Ser Ser
            195                 200                 205 tac aat tat ctg gca gac ggt gga cta gct att tta gac aca tct ggt      672
Tyr Asn Tyr Leu Ala Asp Gly Gly Leu Ala Ile Leu Asp Thr Ser Gly
    210                 215                 220 gcc ata gat atc ttc gtt gta caa ggt gaa tat ggt ttt aat tat tat      720
Ala Ile Asp Ile Phe Val Val Gln Gly Glu Tyr Gly Phe Asn Tyr Tyr
225                 230                 235                 240 aag gtt aac cct tgt gaa gat gta acc aac agc gtt gta gtg tca ggt      768
Lys Val Asn Pro Cys Glu Asp Val Thr Asn Ser Val Val Val Ser Gly
            245                 250                 255 ggt aat ata gtt ggc att ctt act tca cgt aat gaa act gat tct cag      816
Gly Asn Ile Val Gly Ile Leu Thr Ser Arg Asn Glu Thr Asp Ser Gln
            260                 265                 270 cct ctt gaa aat cag ttt tat att aag tta act aat gga agt cgt cgt      864
Pro Leu Glu Asn Gln Phe Tyr Ile Lys Leu Thr Asn Gly Ser Arg Arg
            275                 280                 285 tct aga cgt tct att agt agt aat gtt act aat cgc cct tat gtt act      912
Ser Arg Arg Ser Ile Ser Ser Asn Val Thr Asn Arg Pro Tyr Val Thr
            290                 295                 300 tat gga agg gcg aat tcc agc aca ctg gcg gcc gtt act agt gga tcc      960
Tyr Gly Arg Ala Asn Ser Ser Thr Leu Ala Ala Val Thr Ser Gly Ser
305                 310                 315                 320 gag ctc ggt acc aag ctt gat gca tac                                  987
Glu Leu Gly Thr Lys Leu Asp Ala Tyr
                325
```

Figure 2

| Figure 2a |
|---|
| Figure 2b |
| Figure 2c |

Figure 2a

```
atg ccg ccg aag tca ctg tgt tta gtg acc att ttg ttt gta cta tgt         48
Met Pro Pro Lys Ser Leu Cys Leu Val Thr Ile Leu Phe Val Leu Cys
1             5                  10                 15 agt gct aat tta tat gat aat aat tct tgt gtg tat tac tac cag agt         96
Ser Ala Asn Leu Tyr Asp Asn Asn Ser Cys Val Tyr Tyr Tyr Gln Ser
             20                  25                 30 gct ttt agg cca gga ctt ggt tgg cat tta cat gga ggt gct tat gca        144
Ala Phe Arg Pro Gly Leu Gly Trp His Leu His Gly Gly Ala Tyr Ala
             35                  40                 45 gta gtt aat gtg tct tct gaa act aat aat gca ggc tcc tca tct tct        192
Val Val Asn Val Ser Ser Glu Thr Asn Asn Ala Gly Ser Ser Ser Ser
             50                  55                 60 tgc act gct ggt gct att tat tgg agt aaa aat ttt agt gca gct tct        240
Cys Thr Ala Gly Ala Ile Tyr Trp Ser Lys Asn Phe Ser Ala Ala Ser
65                  70                  75                 80 gta gcc atg act gca cca gat tct ggt atg tta tgg tct gca aac caa        288
Val Ala Met Thr Ala Pro Asp Ser Gly Met Leu Trp Ser Ala Asn Gln
             85                  90                 95 ttt tgt acg gcc cac tgc aat ttt act agt ttt aca gtg ctt gtt aca        336
Phe Cys Thr Ala His Cys Asn Phe Thr Ser Phe Thr Val Leu Val Thr
             100                 105                110 cat tgt ttt aag tca ggt gcc aag gag tgt cct ttg act ggt ctg att        384
His Cys Phe Lys Ser Gly Ala Lys Glu Cys Pro Leu Thr Gly Leu Ile
             115                 120                125 caa aag ggt tat ctt cgc att gcc gct atg aaa caa aac ggt aga ggg        432
Gln Lys Gly Tyr Leu Arg Ile Ala Ala Met Lys Gln Asn Gly Arg Gly
             130                 135                140 cct gct gac tta ttt tat aat tta aca gtt cca gtg act aga tac ccc        480
Pro Ala Asp Leu Phe Tyr Asn Leu Thr Val Pro Val Thr Arg Tyr Pro
145                 150                 155                160 gtg gtt aga tca ctt caa tgt gtt aat aat caa aca tct gtg tat tta        528
Val Val Arg Ser Leu Gln Cys Val Asn Asn Gln Thr Ser Val Tyr Leu
             165                 170                175 aat gtt gat ctt gtt ttt act tct aat gag act att gga ttc tca ggt        576
Asn Val Asp Leu Val Phe Thr Ser Asn Glu Thr Ile Gly Phe Ser Gly
             180                 185                190
```

```
gct ggt gtt cat ttt aga gct ggc ggc cct ata act tat aaa gtt atg      624
Ala Gly Val His Phe Arg Ala Gly Gly Pro Ile Thr Tyr Lys Val Met
        195                 200                 205 aga gaa gta aaa gcc ttg gct tat ttt tct aat ggt act gca caa gat      672
Arg Glu Val Lys Ala Leu Ala Tyr Phe Ser Asn Gly Thr Ala Gln Asp
    210                 215                 220 gtt att ctt tgt gat gag cca cct aga ggt ttg tta gcc tgc caa tat      720
Val Ile Leu Cys Asp Glu Pro Pro Arg Gly Leu Leu Ala Cys Gln Tyr
225                 230                 235                 240 ata ctg gcc aat ttt tca gat ggc ctt ccg tcc ctt tta ctg agt tca      768
Ile Leu Ala Asn Phe Ser Asp Gly Leu Pro Ser Leu Leu Leu Ser Ser
                245                 250                 255 agt tta gtt agg cga aag ttt att gtt tat cgt gag aat agt att aat      816
Ser Leu Val Arg Arg Lys Phe Ile Val Tyr Arg Glu Asn Ser Ile Asn
        260                 265                 270 acc act ttg gtt tta cat att ttt acg ttt cat aat gaa agc aat gca      864
Thr Thr Leu Val Leu His Ile Phe Thr Phe His Asn Glu Ser Asn Ala
    275                 280                 285 caa cct aat ctg gtg ggt gtt aag aac att gct att tat caa aca caa      912
Gln Pro Asn Leu Val Gly Val Lys Asn Ile Ala Ile Tyr Gln Thr Gln
290                 295                 300 aca gct cag agt ggc tat tat aat ttt aat ttc tca ttt ctg agt agt      960
Thr Ala Gln Ser Gly Tyr Tyr Asn Phe Asn Phe Ser Phe Leu Ser Ser
305                 310                 315                 320 ttt gtt tat aag tca agt gat ttt atg tat ggg tct ttt cac cca cag     1008
Phe Val Tyr Lys Ser Ser Asp Phe Met Tyr Gly Ser Phe His Pro Gln
                325                 330                 335 tgt agt ttt aga cca gaa aac att aat aat ggg ctc tgg ttc aat tca     1056
Cys Ser Phe Arg Pro Glu Asn Ile Asn Asn Gly Leu Trp Phe Asn Ser
        340                 345                 350 ctt tca att tca ctt gct tac ggc cca cta caa ggg ggc tgt aaa cag     1104
Leu Ser Ile Ser Leu Ala Tyr Gly Pro Leu Gln Gly Gly Cys Lys Gln
    355                 360                 365
```

Figure 2c

```
tca gtt ttt agt cgc aaa aca acg tgt tgt tat gct tat tca tat ggc      1152
Ser Val Phe Ser Arg Lys Thr Thr Cys Cys Tyr Ala Tyr Ser Tyr Gly
    370                 375                 380 ggt cct cat ttg tgt aaa ggt gtt tat gca ggt gag tta aca aag aat      1200
Gly Pro His Leu Cys Lys Gly Val Tyr Ala Gly Glu Leu Thr Lys Asn
385                 390                 395                 400 ttt gaa tgt ggc ttg tta gtt tat att act aag agt gat ggt tct cgt      1248
Phe Glu Cys Gly Leu Leu Val Tyr Ile Thr Lys Ser Asp Gly Ser Arg
                405                 410                 415 ata caa acg gca aca gaa gca cct gta gta acc aca aat ttt tac aat      1296
Ile Gln Thr Ala Thr Glu Ala Pro Val Val Thr Thr Asn Phe Tyr Asn
            420                 425                 430 aac att act ttg aat aag tgt gtt gag tat aat ata tac ggt aga att      1344
Asn Ile Thr Leu Asn Lys Cys Val Glu Tyr Asn Ile Tyr Gly Arg Ile
        435                 440                 445 ggc caa ggt ttt att act aat gta act gat tta gct tct agt tac aat      1392
Gly Gln Gly Phe Ile Thr Asn Val Thr Asp Leu Ala Ser Ser Tyr Asn
    450                 455                 460 tat ctg gca gac ggt gga cta gct att tta gac aca tct ggt gcc ata      1440
Tyr Leu Ala Asp Gly Gly Leu Ala Ile Leu Asp Thr Ser Gly Ala Ile
465                 470                 475                 480 gat atc ttc gtt gta caa ggt gaa tat ggt ttt aat tat tat aag gtt      1488
Asp Ile Phe Val Val Gln Gly Glu Tyr Gly Phe Asn Tyr Tyr Lys Val
                485                 490                 495 aac cct tgt gaa gat gtt aac caa cag ttt gta gtg tca ggt ggt aat      1536
Asn Pro Cys Glu Asp Val Asn Gln Gln Phe Val Val Ser Gly Gly Asn
            500                 505                 510 ata gtt ggc att ctt act tca cgt aat gaa act gat tct cag cct ctt      1584
Ile Val Gly Ile Leu Thr Ser Arg Asn Glu Thr Asp Ser Gln Pro Leu
        515                 520                 525 gaa aat cag ttt tat att aag tta act aat gga agt cgt cgt gcg           1629
Glu Asn Gln Phe Tyr Ile Lys Leu Thr Asn Gly Ser Arg Arg Ala
    530                 535                 540
```

*Figure 5*

| *Figure 5ₐ* |
|---|
| *Figure 5ᵦ* |
| *Figure 5 c* |

Figure 5a

| | | | | | | | | | | | | | | | | |
|---|---|---|---|---|---|---|---|---|---|---|---|---|---|---|---|---|
| atg | ttg | ggg | aag | tca | ctg | ttt | tta | gtg | act | att | ttg | ttt | gca | cta | tgt | 48 |
| Met | Leu | Gly | Lys | Ser | Leu | Phe | Leu | Val | Thr | Ile | Leu | Phe | Ala | Leu | Cys | |
| 1 | | | | 5 | | | | | 10 | | | | | 15 | | |
| agt | gca | aat | ttg | ttt | gat | cat | aat | tat | gtt | tac | tac | tac | caa | agt | gcc | 96 |
| Ser | Ala | Asn | Leu | Phe | Asp | His | Asn | Tyr | Val | Tyr | Tyr | Tyr | Gln | Ser | Ala | |
| | | | 20 | | | | | 25 | | | | | 30 | | | |
| ttt | aga | cca | tca | aat | ggt | tgg | cat | tta | caa | ggg | ggt | gcg | tat | cag | nta | 144 |
| Phe | Arg | Pro | Ser | Asn | Gly | Trp | His | Leu | Gln | Gly | Gly | Ala | Tyr | Gln | Xaa | |
| | | 35 | | | | | 40 | | | | | 45 | | | | |
| gtt | aat | tct | act | agt | cac | ttt | aat | aat | gca | ggc | gct | gca | tca | gta | tgt | 192 |
| Val | Asn | Ser | Thr | Ser | His | Phe | Asn | Asn | Ala | Gly | Ala | Ala | Ser | Val | Cys | |
| | 50 | | | | | 55 | | | | | 60 | | | | | |
| act | ggt | ggt | ttg | ctt | aca | gat | gtt | tac | aac | aac | aca | gct | gct | gct | ata | 240 |
| Thr | Gly | Gly | Leu | Leu | Thr | Asp | Val | Tyr | Asn | Asn | Thr | Ala | Ala | Ala | Ile | |
| 65 | | | | | 70 | | | | | 75 | | | | | 80 | |
| tct | atg | gta | gca | ccg | gct | tca | ggt | atg | agt | tgg | tct | aca | tca | cag | ttt | 288 |
| Ser | Met | Val | Ala | Pro | Ala | Ser | Gly | Met | Ser | Trp | Ser | Thr | Ser | Gln | Phe | |
| | | | | 85 | | | | | 90 | | | | | 95 | | |
| tgt | act | gct | cat | tgt | aga | ttc | tca | gac | ctt | act | gtg | ttt | gtt | acg | cac | 336 |
| Cys | Thr | Ala | His | Cys | Arg | Phe | Ser | Asp | Leu | Thr | Val | Phe | Val | Thr | His | |
| | | | 100 | | | | | 105 | | | | | 110 | | | |
| tgt | tat | aac | gcg | tct | aat | ggt | gct | tgt | cct | ata | aca | ggt | ttt | gta | cca | 384 |
| Cys | Tyr | Asn | Ala | Ser | Asn | Gly | Ala | Cys | Pro | Ile | Thr | Gly | Phe | Val | Pro | |
| | | 115 | | | | | 120 | | | | | 125 | | | | |
| cag | aat | cat | att | cgc | att | tct | gct | atg | aga | aat | ggt | tct | ttt | ctt | tat | 432 |
| Gln | Asn | His | Ile | Arg | Ile | Ser | Ala | Met | Arg | Asn | Gly | Ser | Phe | Leu | Tyr | |
| | 130 | | | | | 135 | | | | | 140 | | | | | |
| aac | tta | aca | gtt | agt | gtg | ctt | aaa | tac | cct | aag | ttt | cat | tct | ttt | caa | 480 |
| Asn | Leu | Thr | Val | Ser | Val | Leu | Lys | Tyr | Pro | Lys | Phe | His | Ser | Phe | Gln | |
| 145 | | | | | 150 | | | | | 155 | | | | | 160 | |
| tgt | gtt | ggc | aat | caa | aca | tct | gtg | tat | ctt | aac | ggt | gat | ctt | gtt | tac | 528 |
| Cys | Val | Gly | Asn | Gln | Thr | Ser | Val | Tyr | Leu | Asn | Gly | Asp | Leu | Val | Tyr | |
| | | | | 165 | | | | | 170 | | | | | 175 | | |

Figure 5b

```
act tcc aac acc acc act act gtt acg tca gca ggt gtg cat ttt aaa      576
Thr Ser Asn Thr Thr Thr Thr Val Thr Ser Ala Gly Val His Phe Lys
            180                 185                 190 gca ggt gga cct gta aat tat agt gtt atg aga gaa ttt cag gca ctt      624
Ala Gly Gly Pro Val Asn Tyr Ser Val Met Arg Glu Phe Gln Ala Leu
            195                 200                 205 gct tat ttt gtt aat ggg act gta caa gac gtt atc ttg tgc gat gaa      672
Ala Tyr Phe Val Asn Gly Thr Val Gln Asp Val Ile Leu Cys Asp Glu
            210                 215                 220 aca cct aga ggt tta tta gca tgt caa tat aat act ggc aat ttt tca      720
Thr Pro Arg Gly Leu Leu Ala Cys Gln Tyr Asn Thr Gly Asn Phe Ser
225                 230                 235                 240 gat gga tta tac cct ttt act aat aat act tta gta aaa cag aag ttc      768
Asp Gly Leu Tyr Pro Phe Thr Asn Asn Thr Leu Val Lys Gln Lys Phe
                245                 250                 255 att gtt tat cgg gag aat agt gtt aat acc act tng gtt tng cat aat      816
Ile Val Tyr Arg Glu Asn Ser Val Asn Thr Thr Xaa Val Xaa His Asn
            260                 265                 270 ttt act ttt agt aat gag act aat gca caa cct aat aca ggt ggt gtt      864
Phe Thr Phe Ser Asn Glu Thr Asn Ala Gln Pro Asn Thr Gly Gly Val
            275                 280                 285 cat act att aag tta tat caa aca cgt aca gct cag agt ggt tat tat      912
His Thr Ile Lys Leu Tyr Gln Thr Arg Thr Ala Gln Ser Gly Tyr Tyr
            290                 295                 300 aat ttt aat ttt tcc ttt ctg agt ggt ttt gtc tat aag gag tct aat      960
Asn Phe Asn Phe Ser Phe Leu Ser Gly Phe Val Tyr Lys Glu Ser Asn
305                 310                 315                 320 ttt atg tat gga tct tat cac cca agt tgt aag ttt aga cca gaa act     1008
Phe Met Tyr Gly Ser Tyr His Pro Ser Cys Lys Phe Arg Pro Glu Thr
                325                 330                 335 att aat aat ggc ttg tgg ttt aat tca ctt tca gtt tca ctt gca tat     1056
Ile Asn Asn Gly Leu Trp Phe Asn Ser Leu Ser Val Ser Leu Ala Tyr
            340                 345                 350
```

Figure 5c

```
ggc ccc ctt caa ggt ggg tgt aag cag tca gtt ttt ggt ggt aag gct    1104
Gly Pro Leu Gln Gly Gly Cys Lys Gln Ser Val Phe Gly Gly Lys Ala
        355                 360                 365 act tgt tgt tat gcc tac tct tat ggc gga cca cat aat tgt aaa gga    1152
Thr Cys Cys Tyr Ala Tyr Ser Tyr Gly Gly Pro His Asn Cys Lys Gly
        370                 375                 380 gtt tat agt ggt gag tta tca agt aat ttt gaa tgt ggg ctg ttg gtt    1200
Val Tyr Ser Gly Glu Leu Ser Ser Asn Phe Glu Cys Gly Leu Leu Val
385                 390                 395                 400 tat gtt act aag agt gat gct gct cgc ata caa aca gcc aca gaa tca    1248
Tyr Val Thr Lys Ser Asp Ala Ala Arg Ile Gln Thr Ala Thr Glu Ser
        405                 410                 415 ccg gtt ata act caa cac aat tat aat aat att act tta aat acg tgt    1296
Pro Val Ile Thr Gln His Asn Tyr Asn Asn Ile Thr Leu Asn Thr Cys
        420                 425                 430 gtt gag tat aat ata tat ggc aga gtt gga caa ggt ttt att act aat    1344
Val Glu Tyr Asn Ile Tyr Gly Arg Val Gly Gln Gly Phe Ile Thr Asn
        435                 440                 445 gta act gac tca gca tct atg ggg aat tat tta gca gat gca gga tta    1392
Val Thr Asp Ser Ala Ser Met Gly Asn Tyr Leu Ala Asp Ala Gly Leu
        450                 455                 460 gct att tta gat aca tca ggt gcc ata gac acc ttt gtt gta caa ggt    1440
Ala Ile Leu Asp Thr Ser Gly Ala Ile Asp Thr Phe Val Val Gln Gly
465                 470                 475                 480 gga tat ggt ctc aat tat tat aag gtt aac cct tgc gaa gat gtt aat    1488
Gly Tyr Gly Leu Asn Tyr Tyr Lys Val Asn Pro Cys Glu Asp Val Asn
        485                 490                 495 cag cag ttt gta gtg tca ggc g                                      1510
Gln Gln Phe Val Val Ser Gly
        500
```

SEQUENCE LISTING

```
<160> NUMBER OF SEQ ID NOS: 19

<210> SEQ ID NO 1
<211> LENGTH: 385
<212> TYPE: DNA
<213> ORGANISM: avian Infectious Bronchitis Virus

<400> SEQUENCE: 1
ctggcaattt tttcagatgg attatacccct tttactaata atactttagt aaaacagaag      60
ttcattgttt atcgggagaa tagtgttaat accactttgg ttttgcataa ttttactttt     120
```

-continued

| | |
|---|---|
| agtaatgaga ctaatgcaca acctaataca ggtggtgttc atactattaa gttatatcaa | 180 |
| acacgtacag ctcagagtgg ttattataat tttaattttt cctttctgag tggttttgtc | 240 |
| tataaggagt ctaattttat gtatggatct tatcacccaa gttgtaagtt tagaccagaa | 300 |
| actattaata atggtttgtg gtttaattca cttcagtttc acttgcatat ggcccccctt | 360 |
| caaggtggtt gcaagcaatc tgtaa | 385 |

<210> SEQ ID NO 2
<211> LENGTH: 719
<212> TYPE: DNA
<213> ORGANISM: avian Infectious Bronchitis Virus

<400> SEQUENCE: 2

| | |
|---|---|
| ggaaagttta ttgtttatcg tgagaatagt attaatacca ctttggtttt acataatttt | 60 |
| acgtttcata atgaaagcaa tgcacaacct aatcttggtg gtgttaataa cattgcwatt | 120 |
| tatcaaacac aaacagctca gagtggctat tataatttta atttctcatt tctgagtagt | 180 |
| tttgttttata agtcaagtga ttttatgtat gggtcttttc acccacagtg tagttttaga | 240 |
| ccagaaaaca ttaataatgg ctctggttc aattcacttt caatttcact tgcttacggc | 300 |
| ccactacaag ggggctgtaa acagtcagtt tttagtcgca aaacaacgtg ttgttatgct | 360 |
| tattcatatg gcggtcctca tttgtgtaaa ggtgtttatg caggtgagtt aacaaagaat | 420 |
| tttgaatgtg gcttgttagt ttatattact aagagtgagt gatggttctc gtatacaaac | 480 |
| ggcaacagaa gcacctgtag taaccacaaa tttttacaat aacattactt tgaataagtg | 540 |
| tgttgagtat aatatatacg gtagaattgg ccaaggtttt attactaatg taactgattt | 600 |
| agcttctagt tacaaattatc tggcagacgg tggactagct attttagaca catctggtgc | 660 |
| catagatatc ttcgttgtac acccttgtga agatgttaac caacagtttg tagtgtcag | 719 |

<210> SEQ ID NO 3
<211> LENGTH: 1628
<212> TYPE: DNA
<213> ORGANISM: avian Infectious Bronchitis Virus

<400> SEQUENCE: 3

| | |
|---|---|
| atgttgggga agtcactgtt tttagtgacc attttgtttg cactatgtag tgctaattta | 60 |
| tatgataata attcttttgt gtattactac cagagtgctt ttaggccagg acttggttgg | 120 |
| catttacatg gaggtgctta tgcagtagtt aatgtgtctt ctgaaactaa taatgcaggc | 180 |
| tcctcatctt cttgcactgc tggtgctatt tattggagta aaaattttag tgcagcttct | 240 |
| gtagccatga ctgcaccaga ttctggtatg ttatggtctg caaaccaatt ttgtacggcc | 300 |
| cactgcaatt ttactagttt tacagtgttt gttacacatt gttttaagtc aggtgccaag | 360 |
| gagtgtcctt tgactggtct gattcaaaag ggttatcttc gcattgccgc tatgaaacaa | 420 |
| aacggtagtg ggcctgctga cttattttat aatttaacag ttccagtgac taaataccct | 480 |
| gtgtttagat cacttcaatg tgttaataat caaacatctg tatatttaaa tggtgatctt | 540 |
| gtttttactt ctaatgagac tattgatgtc tcaggtgctg tgttcatttt aaagctggt | 600 |
| ggacctataa cttataaagt tatgagagaa gtaaaagctt ggcttattt tgttaatggt | 660 |
| actgcacaag atgttattct ttgtgatgag tcacctagag gtttgttagc atgccaatat | 720 |
| aatactggca ttttttcaga tggcttctat ccttttacta attctagttt agttaaggaa | 780 |
| aagtttattg tttatcgtga gaatagtatt aataccactt tggttttaca taattttacg | 840 |
| tttcataatg aaagcaatgc acaacctaat cttggtggtg ttaataacat tgctatttat | 900 |

-continued

```
caaacacaaa cagctcagag tggctattat aattttaatt tctcattcct gagtagtttt    960
gtttataagt caagtgattt tatgtatggg tcttttcacc cacagtgtag ttttagacca   1020
gaaaacatta ataatgggct ctggttcaat tcactttcaa tttcacttgc ttacggccca   1080
ctacaagggg gctgtaaaca gtcagttttt agtcgcaaaa caacgtgttg ttatgcttat   1140
tcatatggcg gtcctcattt gtgtaaaggt gtttatgcag gtgagttaac aaagaatttt   1200
gaatgtggct tgttagttta tattactaag agtgatggtt ctcgtataca aacggcaaca   1260
gaagcacctg tagtaaccac aaatttttac aataacatta ctttgaataa gtgtgttgag   1320
tataatatat acggtagaat tggccaaggt tttattacta atgtaactga tttagcttct   1380
agttacaatt atctggcaga cggtggacta gctatttag acacatctgg tgccatagat   1440
atcttcgttg tacaaggtga atatggtttt aattattata aggttaaccc ttgtgaagat   1500
gttaaccaac agtttgtagt gtcaggtggt aatatagttg gcattcttac ttcacgtaat   1560
gaaactgatt ctcagcctct tgaaaatcag ttttatatta agttaactaa tggaagtcgt   1620
cgttctag                                                           1628
```

<210> SEQ ID NO 4
<211> LENGTH: 127
<212> TYPE: PRT
<213> ORGANISM: avian Infectious Bronchitis Virus

<400> SEQUENCE: 4

```
Leu Ala Ile Phe Ser Asp Gly Leu Tyr Pro Phe Thr Asn Asn Thr Leu
1               5                   10                  15

Val Lys Gln Lys Phe Ile Val Tyr Arg Glu Asn Ser Val Asn Thr Thr
            20                  25                  30

Leu Val Leu His Asn Phe Thr Phe Ser Asn Glu Thr Asn Ala Gln Pro
        35                  40                  45

Asn Thr Gly Gly Val His Thr Ile Lys Leu Tyr Gln Thr Arg Thr Ala
    50                  55                  60

Gln Ser Gly Tyr Tyr Asn Phe Asn Phe Ser Phe Leu Ser Gly Phe Val
65                  70                  75                  80

Tyr Lys Glu Ser Asn Phe Met Tyr Gly Ser Tyr His Pro Ser Cys Lys
                85                  90                  95

Phe Arg Pro Glu Thr Ile Asn Asn Gly Leu Trp Phe Asn Ser Leu Gln
            100                 105                 110

Phe His Leu His Met Ala Pro Phe Lys Val Val Ala Ser Asn Leu
        115                 120                 125
```

<210> SEQ ID NO 5
<211> LENGTH: 249
<212> TYPE: PRT
<213> ORGANISM: avian Infectious Bronchitis Virus

<400> SEQUENCE: 5

```
Gly Lys Phe Ile Val Tyr Arg Glu Asn Ser Ile Asn Thr Thr Leu Val
1               5                   10                  15

Leu His Asn Phe Thr Phe His Asn Glu Ser Asn Ala Gln Pro Asn Leu
            20                  25                  30

Gly Gly Val Asn Asn Ile Ala Ile Tyr Gln Thr Gln Thr Ala Gln Ser
        35                  40                  45

Gly Tyr Tyr Asn Phe Asn Phe Ser Phe Leu Ser Ser Phe Val Tyr Lys
    50                  55                  60

Ser Ser Asp Phe Met Tyr Gly Ser Phe His Pro Gln Cys Ser Phe Arg
```

```
                65                  70                  75                  80
Pro Glu Asn Ile Asn Asn Gly Leu Trp Phe Asn Ser Leu Ser Ile Ser
                    85                  90                  95
Leu Ala Tyr Gly Pro Leu Gln Gly Gly Cys Lys Gln Ser Val Phe Ser
                100                 105                 110
Arg Lys Thr Thr Cys Cys Tyr Ala Tyr Ser Tyr Gly Gly Pro His Leu
                115                 120                 125
Cys Lys Gly Val Tyr Ala Gly Glu Leu Thr Lys Asn Phe Glu Cys Gly
                130                 135                 140
Leu Leu Val Tyr Ile Thr Lys Ser Asp Gly Ser Arg Ile Gln Thr Ala
145                 150                 155                 160
Thr Glu Ala Pro Val Val Thr Thr Asn Phe Tyr Asn Asn Ile Thr Leu
                165                 170                 175
Asn Lys Cys Val Glu Tyr Asn Ile Tyr Gly Arg Ile Gly Gln Gly Phe
                180                 185                 190
Ile Thr Asn Val Thr Asp Leu Ala Ser Ser Tyr Asn Tyr Leu Ala Asp
                195                 200                 205
Gly Gly Leu Ala Ile Leu Asp Thr Ser Gly Ala Ile Asp Ile Phe Val
                210                 215                 220
Val Gln Gly Glu Tyr Gly Phe Asn Tyr Tyr Lys Val Asn Pro Cys Glu
225                 230                 235                 240
Asp Val Asn Gln Gln Phe Val Val Ser
                245

<210> SEQ ID NO 6
<211> LENGTH: 542
<212> TYPE: PRT
<213> ORGANISM: avian Infectious Bronchitis Virus

<400> SEQUENCE: 6

Met Leu Gly Lys Ser Leu Phe Leu Val Thr Ile Leu Phe Ala Leu Cys
1               5                   10                  15
Ser Ala Asn Leu Tyr Asp Asn Asn Ser Phe Val Tyr Tyr Tyr Gln Ser
                20                  25                  30
Ala Phe Arg Pro Gly Leu Gly Trp His Leu His Gly Gly Ala Tyr Ala
                35                  40                  45
Val Val Asn Val Ser Ser Glu Thr Asn Asn Ala Gly Ser Ser Ser Ser
                50                  55                  60
Cys Thr Ala Gly Ala Ile Tyr Trp Ser Lys Asn Phe Ser Ala Ala Ser
65                  70                  75                  80
Val Ala Met Thr Ala Pro Asp Ser Gly Met Leu Trp Ser Ala Asn Gln
                85                  90                  95
Phe Cys Thr Ala His Cys Asn Phe Thr Ser Phe Thr Val Phe Val Thr
                100                 105                 110
His Cys Phe Lys Ser Gly Ala Lys Glu Cys Pro Leu Thr Gly Leu Ile
                115                 120                 125
Gln Lys Gly Tyr Leu Arg Ile Ala Ala Met Lys Gln Asn Gly Ser Gly
                130                 135                 140
Pro Ala Asp Leu Phe Tyr Asn Leu Thr Val Pro Val Thr Lys Tyr Pro
145                 150                 155                 160
Val Phe Arg Ser Leu Gln Cys Val Asn Asn Gln Thr Ser Val Tyr Leu
                165                 170                 175
Asn Gly Asp Leu Val Phe Thr Ser Asn Glu Thr Ile Asp Val Ser Gly
                180                 185                 190
Ala Gly Val His Phe Lys Ala Gly Gly Pro Ile Thr Tyr Lys Val Met
```

```
            195                 200                 205
Arg Glu Val Lys Ala Leu Ala Tyr Phe Val Asn Gly Thr Ala Gln Asp
210                 215                 220

Val Ile Leu Cys Asp Glu Ser Pro Arg Gly Leu Leu Ala Cys Gln Tyr
225                 230                 235                 240

Asn Thr Gly Asn Phe Ser Asp Gly Phe Tyr Pro Phe Thr Asn Ser Ser
                245                 250                 255

Leu Val Lys Glu Lys Phe Ile Val Tyr Arg Glu Asn Ser Ile Asn Thr
            260                 265                 270

Thr Leu Val Leu His Asn Phe Thr Phe His Asn Glu Ser Asn Ala Gln
        275                 280                 285

Pro Asn Leu Gly Gly Val Asn Asn Ile Ala Ile Tyr Gln Thr Gln Thr
    290                 295                 300

Ala Gln Ser Gly Tyr Tyr Asn Phe Asn Phe Ser Phe Leu Ser Ser Phe
305                 310                 315                 320

Val Tyr Lys Ser Ser Asp Phe Met Tyr Gly Ser Phe His Pro Gln Cys
                325                 330                 335

Ser Phe Arg Pro Glu Asn Ile Asn Asn Gly Leu Trp Phe Asn Ser Leu
            340                 345                 350

Ser Ile Ser Leu Ala Tyr Gly Pro Leu Gln Gly Gly Cys Lys Gln Ser
        355                 360                 365

Val Phe Ser Arg Lys Thr Thr Cys Cys Tyr Ala Tyr Ser Tyr Gly Gly
    370                 375                 380

Pro His Leu Cys Lys Gly Val Tyr Ala Gly Glu Leu Thr Lys Asn Phe
385                 390                 395                 400

Glu Cys Gly Leu Leu Val Tyr Ile Thr Lys Ser Asp Gly Ser Arg Ile
                405                 410                 415

Gln Thr Ala Thr Glu Ala Pro Val Val Thr Thr Asn Phe Tyr Asn Asn
            420                 425                 430

Ile Thr Leu Asn Lys Cys Val Glu Tyr Asn Ile Tyr Gly Arg Ile Gly
        435                 440                 445

Gln Gly Phe Ile Thr Asn Val Thr Asp Leu Ala Ser Ser Tyr Asn Tyr
    450                 455                 460

Leu Ala Asp Gly Gly Leu Ala Ile Leu Asp Thr Ser Gly Ala Ile Asp
465                 470                 475                 480

Ile Phe Val Val Gln Gly Glu Tyr Gly Phe Asn Tyr Tyr Lys Val Asn
                485                 490                 495

Pro Cys Glu Asp Val Asn Gln Gln Phe Val Val Ser Gly Gly Asn Ile
            500                 505                 510

Val Gly Ile Leu Thr Ser Arg Asn Glu Thr Asp Ser Gln Pro Leu Glu
        515                 520                 525

Asn Gln Phe Tyr Ile Lys Leu Thr Asn Gly Ser Arg Arg Ser
    530                 535                 540

<210> SEQ ID NO 7
<211> LENGTH: 1629
<212> TYPE: DNA
<213> ORGANISM: avian Infectious Bronchitis Virus
<220> FEATURE:
<221> NAME/KEY: CDS
<222> LOCATION: (1)..(1629)

<400> SEQUENCE: 7 atg ccg ccg aag tca ctg tgt tta gtg acc att ttg ttt gta cta tgt      48
Met Pro Pro Lys Ser Leu Cys Leu Val Thr Ile Leu Phe Val Leu Cys
1               5                   10                  15
```

-continued

```
agt gct aat tta tat gat aat aat tct tgt gtg tat tac tac cag agt         96
Ser Ala Asn Leu Tyr Asp Asn Asn Ser Cys Val Tyr Tyr Tyr Gln Ser
        20                  25                  30 gct ttt agg cca gga ctt ggt tgg cat tta cat gga ggt gct tat gca        144
Ala Phe Arg Pro Gly Leu Gly Trp His Leu His Gly Gly Ala Tyr Ala
            35                  40                  45 gta gtt aat gtg tct tct gaa act aat aat gca ggc tcc tca tct tct        192
Val Val Asn Val Ser Ser Glu Thr Asn Asn Ala Gly Ser Ser Ser Ser
 50                  55                  60 tgc act gct ggt gct att tat tgg agt aaa aat ttt agt gca gct tct        240
Cys Thr Ala Gly Ala Ile Tyr Trp Ser Lys Asn Phe Ser Ala Ala Ser
 65                  70                  75                  80 gta gcc atg act gca cca gat tct ggt atg tta tgg tct gca aac caa        288
Val Ala Met Thr Ala Pro Asp Ser Gly Met Leu Trp Ser Ala Asn Gln
                85                  90                  95 ttt tgt acg gcc cac tgc aat ttt act agt ttt aca gtg ctt gtt aca        336
Phe Cys Thr Ala His Cys Asn Phe Thr Ser Phe Thr Val Leu Val Thr
            100                 105                 110 cat tgt ttt aag tca ggt gcc aag gag tgt cct ttg act ggt ctg att        384
His Cys Phe Lys Ser Gly Ala Lys Glu Cys Pro Leu Thr Gly Leu Ile
        115                 120                 125 caa aag ggt tat ctt cgc att gcc gct atg aaa caa aac ggt aga ggg        432
Gln Lys Gly Tyr Leu Arg Ile Ala Ala Met Lys Gln Asn Gly Arg Gly
    130                 135                 140 cct gct gac tta ttt tat aat tta aca gtt cca gtg act aga tac ccc        480
Pro Ala Asp Leu Phe Tyr Asn Leu Thr Val Pro Val Thr Arg Tyr Pro
145                 150                 155                 160 gtg gtt aga tca ctt caa tgt gtt aat aat caa aca tct gtg tat tta        528
Val Val Arg Ser Leu Gln Cys Val Asn Asn Gln Thr Ser Val Tyr Leu
                165                 170                 175 aat gtt gat ctt gtt ttt act tct aat gag act att gga ttc tca ggt        576
Asn Val Asp Leu Val Phe Thr Ser Asn Glu Thr Ile Gly Phe Ser Gly
            180                 185                 190 gct ggt gtt cat ttt aga gct ggc ggc cct ata act tat aaa gtt atg        624
Ala Gly Val His Phe Arg Ala Gly Gly Pro Ile Thr Tyr Lys Val Met
        195                 200                 205 aga gaa gta aaa gcc ttg gct tat ttt tct aat ggt act gca caa gat        672
Arg Glu Val Lys Ala Leu Ala Tyr Phe Ser Asn Gly Thr Ala Gln Asp
    210                 215                 220 gtt att ctt tgt gat gag cca cct aga ggt ttg tta gcc tgc caa tat        720
Val Ile Leu Cys Asp Glu Pro Pro Arg Gly Leu Leu Ala Cys Gln Tyr
225                 230                 235                 240 ata ctg gcc aat ttt tca gat ggc ctt ccg tcc ctt tta ctg agt tca        768
Ile Leu Ala Asn Phe Ser Asp Gly Leu Pro Ser Leu Leu Leu Ser Ser
                245                 250                 255 agt tta gtt agg cga aag ttt att gtt tat cgt gag aat agt att aat        816
Ser Leu Val Arg Arg Lys Phe Ile Val Tyr Arg Glu Asn Ser Ile Asn
            260                 265                 270 acc act ttg gtt tta cat att ttt acg ttt cat aat gaa agc aat gca        864
Thr Thr Leu Val Leu His Ile Phe Thr Phe His Asn Glu Ser Asn Ala
        275                 280                 285 caa cct aat ctg gtg ggt gtt aag aac att gct att tat caa aca caa        912
Gln Pro Asn Leu Val Gly Val Lys Asn Ile Ala Ile Tyr Gln Thr Gln
    290                 295                 300 aca gct cag agt ggc tat tat aat ttt aat ttc tca ttt ctg agt agt        960
Thr Ala Gln Ser Gly Tyr Tyr Asn Phe Asn Phe Ser Phe Leu Ser Ser
305                 310                 315                 320 ttt gtt tat aag tca agt gat ttt atg tat ggg tct ttt cac cca cag       1008
Phe Val Tyr Lys Ser Ser Asp Phe Met Tyr Gly Ser Phe His Pro Gln
                325                 330                 335
```

```
tgt agt ttt aga cca gaa aac att aat aat ggg ctc tgg ttc aat tca      1056
Cys Ser Phe Arg Pro Glu Asn Ile Asn Asn Gly Leu Trp Phe Asn Ser
        340                 345                 350 ctt tca att tca ctt gct tac ggc cca cta caa ggg ggc tgt aaa cag      1104
Leu Ser Ile Ser Leu Ala Tyr Gly Pro Leu Gln Gly Gly Cys Lys Gln
355                 360                 365 tca gtt ttt agt cgc aaa aca acg tgt tgt tat gct tat tca tat ggc      1152
Ser Val Phe Ser Arg Lys Thr Thr Cys Cys Tyr Ala Tyr Ser Tyr Gly
    370                 375                 380 ggt cct cat ttg tgt aaa ggt gtt tat gca ggt gag tta aca aag aat      1200
Gly Pro His Leu Cys Lys Gly Val Tyr Ala Gly Glu Leu Thr Lys Asn
385                 390                 395                 400 ttt gaa tgt ggc ttg tta gtt tat att act aag agt gat ggt tct cgt      1248
Phe Glu Cys Gly Leu Leu Val Tyr Ile Thr Lys Ser Asp Gly Ser Arg
                405                 410                 415 ata caa acg gca aca gaa gca cct gta gta acc aca aat ttt tac aat      1296
Ile Gln Thr Ala Thr Glu Ala Pro Val Val Thr Thr Asn Phe Tyr Asn
            420                 425                 430 aac att act ttg aat aag tgt gtt gag tat aat ata tac ggt aga att      1344
Asn Ile Thr Leu Asn Lys Cys Val Glu Tyr Asn Ile Tyr Gly Arg Ile
        435                 440                 445 ggc caa ggt ttt att act aat gta act gat tta gct tct agt tac aat      1392
Gly Gln Gly Phe Ile Thr Asn Val Thr Asp Leu Ala Ser Ser Tyr Asn
450                 455                 460 tat ctg gca gac ggt gga cta gct att tta gac aca tct ggt gcc ata      1440
Tyr Leu Ala Asp Gly Gly Leu Ala Ile Leu Asp Thr Ser Gly Ala Ile
465                 470                 475                 480 gat atc ttc gtt gta caa ggt gaa tat ggt ttt aat tat tat aag gtt      1488
Asp Ile Phe Val Val Gln Gly Glu Tyr Gly Phe Asn Tyr Tyr Lys Val
                485                 490                 495 aac cct tgt gaa gat gtt aac caa cag ttt gta gtg tca ggt ggt aat      1536
Asn Pro Cys Glu Asp Val Asn Gln Gln Phe Val Val Ser Gly Gly Asn
            500                 505                 510 ata gtt ggc att ctt act tca cgt aat gaa act gat tct cag cct ctt      1584
Ile Val Gly Ile Leu Thr Ser Arg Asn Glu Thr Asp Ser Gln Pro Leu
        515                 520                 525 gaa aat cag ttt tat att aag tta act aat gga agt cgt cgt gcg          1629
Glu Asn Gln Phe Tyr Ile Lys Leu Thr Asn Gly Ser Arg Arg Ala
530                 535                 540

<210> SEQ ID NO 8
<211> LENGTH: 543
<212> TYPE: PRT
<213> ORGANISM: avian Infectious Bronchitis Virus

<400> SEQUENCE: 8

Met Pro Pro Lys Ser Leu Cys Leu Val Thr Ile Leu Phe Val Leu Cys
1               5                   10                  15

Ser Ala Asn Leu Tyr Asp Asn Asn Ser Cys Val Tyr Tyr Gln Ser
            20                  25                  30

Ala Phe Arg Pro Gly Leu Gly Trp His Leu His Gly Gly Ala Tyr Ala
        35                  40                  45

Val Val Asn Val Ser Ser Glu Thr Asn Asn Ala Gly Ser Ser Ser
    50                  55                  60

Cys Thr Ala Gly Ala Ile Tyr Trp Ser Lys Asn Phe Ser Ala Ala Ser
65                  70                  75                  80

Val Ala Met Thr Ala Pro Asp Ser Gly Met Leu Trp Ser Ala Asn Gln
                85                  90                  95

Phe Cys Thr Ala His Cys Asn Phe Thr Ser Phe Thr Val Leu Val Thr
            100                 105                 110
```

```
His Cys Phe Lys Ser Gly Ala Lys Glu Cys Pro Leu Thr Gly Leu Ile
            115                 120                 125
Gln Lys Gly Tyr Leu Arg Ile Ala Ala Met Lys Gln Asn Gly Arg Gly
        130                 135                 140
Pro Ala Asp Leu Phe Tyr Asn Leu Thr Val Pro Val Thr Arg Tyr Pro
145                 150                 155                 160
Val Val Arg Ser Leu Gln Cys Val Asn Gln Thr Ser Val Tyr Leu
                165                 170                 175
Asn Val Asp Leu Val Phe Thr Ser Asn Glu Thr Ile Gly Phe Ser Gly
                180                 185                 190
Ala Gly Val His Phe Arg Ala Gly Gly Pro Ile Thr Tyr Lys Val Met
                195                 200                 205
Arg Glu Val Lys Ala Leu Ala Tyr Phe Ser Asn Gly Thr Ala Gln Asp
        210                 215                 220
Val Ile Leu Cys Asp Glu Pro Pro Arg Gly Leu Leu Ala Cys Gln Tyr
225                 230                 235                 240
Ile Leu Ala Asn Phe Ser Asp Gly Leu Pro Ser Leu Leu Ser Ser
                245                 250                 255
Ser Leu Val Arg Arg Lys Phe Ile Val Tyr Arg Glu Asn Ser Ile Asn
                260                 265                 270
Thr Thr Leu Val Leu His Ile Phe Thr Phe His Asn Glu Ser Asn Ala
        275                 280                 285
Gln Pro Asn Leu Val Gly Val Lys Asn Ile Ala Ile Tyr Gln Thr Gln
        290                 295                 300
Thr Ala Gln Ser Gly Tyr Tyr Asn Phe Asn Phe Ser Phe Leu Ser Ser
305                 310                 315                 320
Phe Val Tyr Lys Ser Ser Asp Phe Met Tyr Gly Ser Phe His Pro Gln
                325                 330                 335
Cys Ser Phe Arg Pro Glu Asn Ile Asn Asn Gly Leu Trp Phe Asn Ser
                340                 345                 350
Leu Ser Ile Ser Leu Ala Tyr Gly Pro Leu Gln Gly Gly Cys Lys Gln
                355                 360                 365
Ser Val Phe Ser Arg Lys Thr Thr Cys Cys Tyr Ala Tyr Ser Tyr Gly
        370                 375                 380
Gly Pro His Leu Cys Lys Gly Val Tyr Ala Gly Glu Leu Thr Lys Asn
385                 390                 395                 400
Phe Glu Cys Gly Leu Leu Val Tyr Ile Thr Lys Ser Asp Gly Ser Arg
                405                 410                 415
Ile Gln Thr Ala Thr Glu Ala Pro Val Val Thr Thr Asn Phe Tyr Asn
                420                 425                 430
Asn Ile Thr Leu Asn Lys Cys Val Glu Tyr Asn Ile Tyr Gly Arg Ile
                435                 440                 445
Gly Gln Gly Phe Ile Thr Asn Val Thr Asp Leu Ala Ser Ser Tyr Asn
        450                 455                 460
Tyr Leu Ala Asp Gly Gly Leu Ala Ile Leu Asp Thr Ser Gly Ala Ile
465                 470                 475                 480
Asp Ile Phe Val Val Gln Gly Glu Tyr Gly Phe Asn Tyr Tyr Lys Val
                485                 490                 495
Asn Pro Cys Glu Asp Val Asn Gln Gln Phe Val Val Ser Gly Gly Asn
                500                 505                 510
Ile Val Gly Ile Leu Thr Ser Arg Asn Glu Thr Asp Ser Gln Pro Leu
                515                 520                 525
Glu Asn Gln Phe Tyr Ile Lys Leu Thr Asn Gly Ser Arg Arg Ala
```

-continued

```
                530                 535                 540

<210> SEQ ID NO 9
<211> LENGTH: 1510
<212> TYPE: DNA
<213> ORGANISM: avian Infectious Bronchitis Virus
<220> FEATURE:
<221> NAME/KEY: CDS
<222> LOCATION: (1)..(1509)
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (803)..(803)
<223> OTHER INFORMATION: n is a, c, g, or t
<220> FEATURE:
<221> NAME/KEY: misc_feature
<222> LOCATION: (809)..(809)
<223> OTHER INFORMATION: n is a, c, g, or t

<400> SEQUENCE: 9 atg ttg ggg aag tca ctg ttt tta gtg act att ttg ttt gca cta tgt      48
Met Leu Gly Lys Ser Leu Phe Leu Val Thr Ile Leu Phe Ala Leu Cys
1               5                   10                  15 agt gca aat ttg ttt gat cat aat tat gtt tac tac tac caa agt gcc     96
Ser Ala Asn Leu Phe Asp His Asn Tyr Val Tyr Tyr Tyr Gln Ser Ala
            20                  25                  30 ttt aga cca tca aat ggt tgg cat tta caa ggg ggt gcg tat cag nta    144
Phe Arg Pro Ser Asn Gly Trp His Leu Gln Gly Gly Ala Tyr Gln Xaa
        35                  40                  45 gtt aat tct act agt cac ttt aat aat gca ggc gct gca tca gta tgt    192
Val Asn Ser Thr Ser His Phe Asn Asn Ala Gly Ala Ala Ser Val Cys
    50                  55                  60 act ggt ggt ttg ctt aca gat gtt tac aac aac aca gct gct gct ata    240
Thr Gly Gly Leu Leu Thr Asp Val Tyr Asn Asn Thr Ala Ala Ala Ile
65                  70                  75                  80 tct atg gta gca ccg gct tca ggt atg agt tgg tct aca tca cag ttt    288
Ser Met Val Ala Pro Ala Ser Gly Met Ser Trp Ser Thr Ser Gln Phe
                85                  90                  95 tgt act gct cat tgt aga ttc tca gac ctt act gtg ttt gtt acg cac    336
Cys Thr Ala His Cys Arg Phe Ser Asp Leu Thr Val Phe Val Thr His
            100                 105                 110 tgt tat aac gcg tct aat ggt gct tgt cct ata aca ggt ttt gta cca    384
Cys Tyr Asn Ala Ser Asn Gly Ala Cys Pro Ile Thr Gly Phe Val Pro
        115                 120                 125 cag aat cat att cgc att tct gct atg aga aat ggt tct ttt ctt tat    432
Gln Asn His Ile Arg Ile Ser Ala Met Arg Asn Gly Ser Phe Leu Tyr
    130                 135                 140 aac tta aca gtt agt gtg ctt aaa tac cct aag ttt cat tct ttt caa    480
Asn Leu Thr Val Ser Val Leu Lys Tyr Pro Lys Phe His Ser Phe Gln
145                 150                 155                 160 tgt gtt ggc aat caa aca tct gtg tat ctt aac ggt gat ctt gtt tac    528
Cys Val Gly Asn Gln Thr Ser Val Tyr Leu Asn Gly Asp Leu Val Tyr
                165                 170                 175 act tcc aac acc acc act act gtt acg tca gca ggt gtg cat ttt aaa    576
Thr Ser Asn Thr Thr Thr Thr Val Thr Ser Ala Gly Val His Phe Lys
            180                 185                 190 gca ggt gga cct gta aat tat agt gtt atg aga gaa ttt cag gca ctt    624
Ala Gly Gly Pro Val Asn Tyr Ser Val Met Arg Glu Phe Gln Ala Leu
        195                 200                 205 gct tat ttt gtt aat ggg act gta caa gac gtt atc ttg tgc gat gaa    672
Ala Tyr Phe Val Asn Gly Thr Val Gln Asp Val Ile Leu Cys Asp Glu
    210                 215                 220
```

```
aca cct aga ggt tta tta gca tgt caa tat aat act ggc aat ttt tca      720
Thr Pro Arg Gly Leu Leu Ala Cys Gln Tyr Asn Thr Gly Asn Phe Ser
225             230                 235                 240 gat gga tta tac cct ttt act aat aat act tta gta aaa cag aag ttc      768
Asp Gly Leu Tyr Pro Phe Thr Asn Asn Thr Leu Val Lys Gln Lys Phe
                245                 250                 255 att gtt tat cgg gag aat agt gtt aat acc act tng gtt tng cat aat      816
Ile Val Tyr Arg Glu Asn Ser Val Asn Thr Thr Xaa Val Xaa His Asn
            260                 265                 270 ttt act ttt agt aat gag act aat gca caa cct aat aca ggt ggt gtt      864
Phe Thr Phe Ser Asn Glu Thr Asn Ala Gln Pro Asn Thr Gly Gly Val
        275                 280                 285 cat act att aag tta tat caa aca cgt aca gct cag agt ggt tat tat      912
His Thr Ile Lys Leu Tyr Gln Thr Arg Thr Ala Gln Ser Gly Tyr Tyr
    290                 295                 300 aat ttt aat ttt tcc ttt ctg agt ggt ttt gtc tat aag gag tct aat      960
Asn Phe Asn Phe Ser Phe Leu Ser Gly Phe Val Tyr Lys Glu Ser Asn
305                 310                 315                 320 ttt atg tat gga tct tat cac cca agt tgt aag ttt aga cca gaa act     1008
Phe Met Tyr Gly Ser Tyr His Pro Ser Cys Lys Phe Arg Pro Glu Thr
                325                 330                 335 att aat aat ggc ttg tgg ttt aat tca ctt tca gtt tca ctt gca tat     1056
Ile Asn Asn Gly Leu Trp Phe Asn Ser Leu Ser Val Ser Leu Ala Tyr
            340                 345                 350 ggc ccc ctt caa ggt ggg tgt aag cag tca gtt ttt ggt ggt aag gct     1104
Gly Pro Leu Gln Gly Gly Cys Lys Gln Ser Val Phe Gly Gly Lys Ala
        355                 360                 365 act tgt tgt tat gcc tac tct tat ggc gga cca cat aat tgt aaa gga     1152
Thr Cys Cys Tyr Ala Tyr Ser Tyr Gly Gly Pro His Asn Cys Lys Gly
    370                 375                 380 gtt tat agt ggt gag tta tca agt aat ttt gaa tgt ggg ctg ttg gtt     1200
Val Tyr Ser Gly Glu Leu Ser Ser Asn Phe Glu Cys Gly Leu Leu Val
385                 390                 395                 400 tat gtt act aag agt gat gct gct cgc ata caa aca gcc aca gaa tca     1248
Tyr Val Thr Lys Ser Asp Ala Ala Arg Ile Gln Thr Ala Thr Glu Ser
                405                 410                 415 ccg gtt ata act caa cac aat tat aat aat att act tta aat acg tgt     1296
Pro Val Ile Thr Gln His Asn Tyr Asn Asn Ile Thr Leu Asn Thr Cys
            420                 425                 430 gtt gag tat aat ata tat ggc aga gtt gga caa ggt ttt att act aat     1344
Val Glu Tyr Asn Ile Tyr Gly Arg Val Gly Gln Gly Phe Ile Thr Asn
        435                 440                 445 gta act gac tca gca tct atg ggg aat tat tta gca gat gca gga tta     1392
Val Thr Asp Ser Ala Ser Met Gly Asn Tyr Leu Ala Asp Ala Gly Leu
    450                 455                 460 gct att tta gat aca tca ggt gcc ata gac acc ttt gtt gta caa ggt     1440
Ala Ile Leu Asp Thr Ser Gly Ala Ile Asp Thr Phe Val Val Gln Gly
465                 470                 475                 480 gga tat ggt ctc aat tat tat aag gtt aac cct tgc gaa gat gtt aat     1488
Gly Tyr Gly Leu Asn Tyr Tyr Lys Val Asn Pro Cys Glu Asp Val Asn
                485                 490                 495 cag cag ttt gta gtg tca ggc g                                        1510
Gln Gln Phe Val Val Ser Gly
                500

<210> SEQ ID NO 10
<211> LENGTH: 503
<212> TYPE: PRT
<213> ORGANISM: avian Infectious Bronchitis Virus
<220> FEATURE:
<221> NAME/KEY: misc_feature
```

```
<222> LOCATION: (48)..(48)
<223> OTHER INFORMATION: The 'Xaa' at location 48 stands for Ile, Val,
      or Leu.
<220> FEATURE:
<221> NAME/KEY: misc_feature
<222> LOCATION: (268)..(268)
<223> OTHER INFORMATION: The 'Xaa' at location 268 stands for Trp, Ser,
      or Leu.
<220> FEATURE:
<221> NAME/KEY: misc_feature
<222> LOCATION: (270)..(270)
<223> OTHER INFORMATION: The 'Xaa' at location 270 stands for Trp, Ser,
      or Leu.

<400> SEQUENCE: 10

Met Leu Gly Lys Ser Leu Phe Leu Val Thr Ile Leu Phe Ala Leu Cys
1               5                   10                  15

Ser Ala Asn Leu Phe Asp His Asn Tyr Val Tyr Tyr Gln Ser Ala
            20                  25                  30

Phe Arg Pro Ser Asn Gly Trp His Leu Gln Gly Gly Ala Tyr Gln Xaa
        35                  40                  45

Val Asn Ser Thr Ser His Phe Asn Asn Ala Gly Ala Ala Ser Val Cys
50                  55                  60

Thr Gly Gly Leu Leu Thr Asp Val Tyr Asn Asn Thr Ala Ala Ala Ile
65                  70                  75                  80

Ser Met Val Ala Pro Ala Ser Gly Met Ser Trp Ser Thr Ser Gln Phe
                85                  90                  95

Cys Thr Ala His Cys Arg Phe Ser Asp Leu Thr Val Phe Val Thr His
            100                 105                 110

Cys Tyr Asn Ala Ser Asn Gly Ala Cys Pro Ile Thr Gly Phe Val Pro
        115                 120                 125

Gln Asn His Ile Arg Ile Ser Ala Met Arg Asn Gly Ser Phe Leu Tyr
130                 135                 140

Asn Leu Thr Val Ser Val Leu Lys Tyr Pro Lys Phe His Ser Phe Gln
145                 150                 155                 160

Cys Val Gly Asn Gln Thr Ser Val Tyr Leu Asn Gly Asp Leu Val Tyr
                165                 170                 175

Thr Ser Asn Thr Thr Thr Thr Val Thr Ser Ala Gly Val His Phe Lys
            180                 185                 190

Ala Gly Gly Pro Val Asn Tyr Ser Val Met Arg Glu Phe Gln Ala Leu
        195                 200                 205

Ala Tyr Phe Val Asn Gly Thr Val Gln Asp Val Ile Leu Cys Asp Glu
210                 215                 220

Thr Pro Arg Gly Leu Leu Ala Cys Gln Tyr Asn Thr Gly Asn Phe Ser
225                 230                 235                 240

Asp Gly Leu Tyr Pro Phe Thr Asn Asn Thr Leu Val Lys Gln Lys Phe
                245                 250                 255

Ile Val Tyr Arg Glu Asn Ser Val Asn Thr Thr Xaa Val Xaa His Asn
            260                 265                 270

Phe Thr Phe Ser Asn Glu Thr Asn Ala Gln Pro Asn Thr Gly Gly Val
        275                 280                 285

His Thr Ile Lys Leu Tyr Gln Thr Arg Thr Ala Gln Ser Gly Tyr Tyr
290                 295                 300

Asn Phe Asn Phe Ser Phe Leu Ser Gly Phe Val Tyr Lys Glu Ser Asn
305                 310                 315                 320

Phe Met Tyr Gly Ser Tyr His Pro Ser Cys Lys Phe Arg Pro Glu Thr
                325                 330                 335

Ile Asn Asn Gly Leu Trp Phe Asn Ser Leu Ser Val Ser Leu Ala Tyr
```

```
                  340               345               350
Gly Pro Leu Gln Gly Gly Cys Lys Gln Ser Val Phe Gly Gly Lys Ala
            355                 360                 365

Thr Cys Cys Tyr Ala Tyr Ser Tyr Gly Gly Pro His Asn Cys Lys Gly
        370                 375                 380

Val Tyr Ser Gly Glu Leu Ser Ser Asn Phe Glu Cys Gly Leu Leu Val
385                 390                 395                 400

Tyr Val Thr Lys Ser Asp Ala Ala Arg Ile Gln Thr Ala Thr Glu Ser
                405                 410                 415

Pro Val Ile Thr Gln His Asn Tyr Asn Asn Ile Thr Leu Asn Thr Cys
            420                 425                 430

Val Glu Tyr Asn Ile Tyr Gly Arg Val Gly Gln Gly Phe Ile Thr Asn
        435                 440                 445

Val Thr Asp Ser Ala Ser Met Gly Asn Tyr Leu Ala Asp Ala Gly Leu
    450                 455                 460

Ala Ile Leu Asp Thr Ser Gly Ala Ile Asp Thr Phe Val Val Gln Gly
465                 470                 475                 480

Gly Tyr Gly Leu Asn Tyr Tyr Lys Val Asn Pro Cys Glu Asp Val Asn
                485                 490                 495

Gln Gln Phe Val Val Ser Gly
            500

<210> SEQ ID NO 11
<211> LENGTH: 987
<212> TYPE: DNA
<213> ORGANISM: avian Infectious Bronchitis Virus
<220> FEATURE:
<221> NAME/KEY: CDS
<222> LOCATION: (1)..(987)

<400> SEQUENCE: 11 att tct agt tta gtt aag gaa aag ttt att gtt tat cgt gag aat agt      48
Ile Ser Ser Leu Val Lys Glu Lys Phe Ile Val Tyr Arg Glu Asn Ser
1               5                   10                  15 att aat acc act ttg gtt tta cat aat ttt acg ttt cat aat gaa agc      96
Ile Asn Thr Thr Leu Val Leu His Asn Phe Thr Phe His Asn Glu Ser
            20                  25                  30 aat gca caa cct aat ctt ggt ggt gtt aat aac att gct att tat caa     144
Asn Ala Gln Pro Asn Leu Gly Gly Val Asn Asn Ile Ala Ile Tyr Gln
        35                  40                  45 aca caa aca gct cag agt ggc tat tat aat ttt aat ttc tca ttt ctg     192
Thr Gln Thr Ala Gln Ser Gly Tyr Tyr Asn Phe Asn Phe Ser Phe Leu
    50                  55                  60 agt agt ttt gtt tat aag tca agt gat ttt atg tat ggg tct ttt cac     240
Ser Ser Phe Val Tyr Lys Ser Ser Asp Phe Met Tyr Gly Ser Phe His
65                  70                  75                  80 cca cag tgt agt ttt aaa cca gaa aac att aat aat ggg ctc tgg ttc     288
Pro Gln Cys Ser Phe Lys Pro Glu Asn Ile Asn Asn Gly Leu Trp Phe
                85                  90                  95 aat tca ctt tca att tca ctt gct tac ggc cca cta caa ggg ggc tgt     336
Asn Ser Leu Ser Ile Ser Leu Ala Tyr Gly Pro Leu Gln Gly Gly Cys
            100                 105                 110 aaa cag tca gtt ttt agt cgc aaa aca acg tgt tgt tat gct tat tca     384
Lys Gln Ser Val Phe Ser Arg Lys Thr Thr Cys Cys Tyr Ala Tyr Ser
        115                 120                 125 tat ggc ggt cct cat ttg tgt aaa ggt gtt tat gca ggt gag tta aca     432
Tyr Gly Gly Pro His Leu Cys Lys Gly Val Tyr Ala Gly Glu Leu Thr
    130                 135                 140 aag aat ttt gaa tgt ggc ttg tta gtt tat att act aag agt gat ggt     480
Lys Asn Phe Glu Cys Gly Leu Leu Val Tyr Ile Thr Lys Ser Asp Gly
```

```
Lys Asn Phe Glu Cys Gly Leu Leu Val Tyr Ile Thr Lys Ser Asp Gly
145                 150                 155                 160 tct cgt ata caa acg gca aca gaa gca cct gta gta acc aca aat ttt    528
Ser Arg Ile Gln Thr Ala Thr Glu Ala Pro Val Val Thr Thr Asn Phe
                165                 170                 175 tac aat aac att act ttg aat aag tgt gtt gag tat aat ata tac ggt    576
Tyr Asn Asn Ile Thr Leu Asn Lys Cys Val Glu Tyr Asn Ile Tyr Gly
                180                 185                 190 aga att ggc caa ggt ttt att act aat gta act gat tta gct tct agt    624
Arg Ile Gly Gln Gly Phe Ile Thr Asn Val Thr Asp Leu Ala Ser Ser
                195                 200                 205 tac aat tat ctg gca gac ggt gga cta gct att tta gac aca tct ggt    672
Tyr Asn Tyr Leu Ala Asp Gly Gly Leu Ala Ile Leu Asp Thr Ser Gly
            210                 215                 220 gcc ata gat atc ttc gtt gta caa ggt gaa tat ggt ttt aat tat tat    720
Ala Ile Asp Ile Phe Val Val Gln Gly Glu Tyr Gly Phe Asn Tyr Tyr
225                 230                 235                 240 aag gtt aac cct tgt gaa gat gta acc aac agc gtt gta gtg tca ggt    768
Lys Val Asn Pro Cys Glu Asp Val Thr Asn Ser Val Val Val Ser Gly
                245                 250                 255 ggt aat ata gtt ggc att ctt act tca cgt aat gaa act gat tct cag    816
Gly Asn Ile Val Gly Ile Leu Thr Ser Arg Asn Glu Thr Asp Ser Gln
                260                 265                 270 cct ctt gaa aat cag ttt tat att aag tta act aat gga agt cgt cgt    864
Pro Leu Glu Asn Gln Phe Tyr Ile Lys Leu Thr Asn Gly Ser Arg Arg
                275                 280                 285 tct aga cgt tct att agt agt aat gtt act aat cgc cct tat gtt act    912
Ser Arg Arg Ser Ile Ser Ser Asn Val Thr Asn Arg Pro Tyr Val Thr
290                 295                 300 tat gga agg gcg aat tcc agc aca ctg gcg gcc gtt act agt gga tcc    960
Tyr Gly Arg Ala Asn Ser Ser Thr Leu Ala Ala Val Thr Ser Gly Ser
305                 310                 315                 320 gag ctc ggt acc aag ctt gat gca tac                                987
Glu Leu Gly Thr Lys Leu Asp Ala Tyr
                325

<210> SEQ ID NO 12
<211> LENGTH: 329
<212> TYPE: PRT
<213> ORGANISM: avian Infectious Bronchitis Virus

<400> SEQUENCE: 12

Ile Ser Ser Leu Val Lys Glu Lys Phe Ile Val Tyr Arg Glu Asn Ser
1               5                   10                  15

Ile Asn Thr Thr Leu Val Leu His Asn Phe Thr Phe His Asn Glu Ser
                20                  25                  30

Asn Ala Gln Pro Asn Leu Gly Gly Val Asn Asn Ile Ala Ile Tyr Gln
            35                  40                  45

Thr Gln Thr Ala Gln Ser Gly Tyr Tyr Asn Phe Asn Phe Ser Phe Leu
        50                  55                  60

Ser Ser Phe Val Tyr Lys Ser Ser Asp Phe Met Tyr Gly Ser Phe His
65                  70                  75                  80

Pro Gln Cys Ser Phe Lys Pro Glu Asn Ile Asn Asn Gly Leu Trp Phe
                85                  90                  95

Asn Ser Leu Ser Ile Ser Leu Ala Tyr Gly Pro Leu Gln Gly Gly Cys
                100                 105                 110

Lys Gln Ser Val Phe Ser Arg Lys Thr Thr Cys Cys Tyr Ala Tyr Ser
            115                 120                 125

Tyr Gly Gly Pro His Leu Cys Lys Gly Val Tyr Ala Gly Glu Leu Thr
```

```
                130              135              140
Lys Asn Phe Glu Cys Gly Leu Leu Val Tyr Ile Thr Lys Ser Asp Gly
145                 150                 155                 160

Ser Arg Ile Gln Thr Ala Thr Glu Ala Pro Val Val Thr Thr Asn Phe
                165                 170                 175

Tyr Asn Asn Ile Thr Leu Asn Lys Cys Val Glu Tyr Asn Ile Tyr Gly
                180                 185                 190

Arg Ile Gly Gln Gly Phe Ile Thr Asn Val Thr Asp Leu Ala Ser Ser
            195                 200                 205

Tyr Asn Tyr Leu Ala Asp Gly Gly Leu Ala Ile Leu Asp Thr Ser Gly
                210                 215                 220

Ala Ile Asp Ile Phe Val Val Gln Gly Glu Tyr Gly Phe Asn Tyr Tyr
225                 230                 235                 240

Lys Val Asn Pro Cys Glu Asp Val Thr Asn Ser Val Val Ser Gly
                245                 250                 255

Gly Asn Ile Val Gly Ile Leu Thr Ser Arg Asn Glu Thr Asp Ser Gln
                260                 265                 270

Pro Leu Glu Asn Gln Phe Tyr Ile Lys Leu Thr Asn Gly Ser Arg Arg
                275                 280                 285

Ser Arg Arg Ser Ile Ser Ser Asn Val Thr Asn Arg Pro Tyr Val Thr
290                 295                 300

Tyr Gly Arg Ala Asn Ser Ser Thr Leu Ala Ala Val Thr Ser Gly Ser
305                 310                 315                 320

Glu Leu Gly Thr Lys Leu Asp Ala Tyr
                325

<210> SEQ ID NO 13
<211> LENGTH: 18
<212> TYPE: DNA
<213> ORGANISM: artificial
<220> FEATURE:
<223> OTHER INFORMATION: synthetic oligonucleotide primer

<400> SEQUENCE: 13
actggcaatt ttttcaga                                              18

<210> SEQ ID NO 14
<211> LENGTH: 19
<212> TYPE: DNA
<213> ORGANISM: artificial
<220> FEATURE:
<223> OTHER INFORMATION: synthetic oligonucleotide primer

<400> SEQUENCE: 14
acagattgct tgcaaccac                                             19

<210> SEQ ID NO 15
<211> LENGTH: 18
<212> TYPE: DNA
<213> ORGANISM: artificial
<220> FEATURE:
<223> OTHER INFORMATION: synthetic oligonucleotide primer

<400> SEQUENCE: 15
gcttttgagc ctagcgtt                                              18

<210> SEQ ID NO 16
<211> LENGTH: 22
<212> TYPE: DNA
<213> ORGANISM: artificial
<220> FEATURE:
```

-continued

```
<223> OTHER INFORMATION: synthetic oligonucleotide primer

<400> SEQUENCE: 16
gccatgttgt cactgtctat tg                                              22

<210> SEQ ID NO 17
<211> LENGTH: 22
<212> TYPE: DNA
<213> ORGANISM: artificial
<220> FEATURE:
<223> OTHER INFORMATION: synthetic oligonucleotide probe
<220> FEATURE:
<221> NAME/KEY: misc_feature
<222> LOCATION: (1)..(1)
<223> OTHER INFORMATION: labelled with a FAM fluorescent dye
<220> FEATURE:
<221> NAME/KEY: misc_feature
<222> LOCATION: (22)..(22)
<223> OTHER INFORMATION: labelled with a BHQ1 fluorescent quencher

<400> SEQUENCE: 17
caccaccaga acctgtcacc tc                                              22

<210> SEQ ID NO 18
<211> LENGTH: 21
<212> TYPE: DNA
<213> ORGANISM: artificial
<220> FEATURE:
<223> OTHER INFORMATION: synthetic oligonucleotide primer

<400> SEQUENCE: 18
ccataagtaa cataaggrcr a                                               21

<210> SEQ ID NO 19
<211> LENGTH: 18
<212> TYPE: DNA
<213> ORGANISM: artificial
<220> FEATURE:
<223> OTHER INFORMATION: synthetic oligonucleotide primer

<400> SEQUENCE: 19
tgaaactgaa caaaagac                                                   18
```

US 8,679,504 B2

POULTRY VIRAL MATERIALS AND METHODS RELATED THERETO

CONTINUING APPLICATION DATA

This application is a continuation-in-part of International Application No. PCT/US2009/044818, filed Mar. 21, 2009, which claims the benefit of U.S. Provisional Application Ser. No. 61/055,158, filed May 22, 2008; further this application claims the benefit of U.S. Provisional Application Ser. No. 61/308,382, filed Feb. 26, 2010; all of which are incorporated herein by reference in their entireties.

BACKGROUND

Infectious bronchitis virus (IBV) is a group 3 avian coronavirus that causes a highly contagious upper-respiratory tract disease in chickens characterized by tracheal rales, coughing, and sneezing. In addition, the disease may affect kidneys, and in laying flocks there is usually a drop in egg production and egg quality. Mortality may occur in young chicks due to respiratory or kidney manifestations of the infection. The disease is prevalent worldwide with significant economic consequences.

Control of the disease is extremely important because IBV predisposes birds to potentially lethal secondary pathogens. Attenuated live vaccines and killed vaccines are used in an attempt to prevent the disease. However, extensive genetic diversity and a high mutation rate results in many different types of the virus that do not serologically cross-react, making it important to vaccinate chickens with the type of IBV causing the disease. IBV variant viruses are consistently circulating in commercial poultry and are capable of causing disease outbreaks. There is little cross-protection between different serotypes of IBV.

Control of IBV relies primarily on the use of mass applied modified live vaccines. Poultry producers face several challenges when trying to control IBV infections in the field. First, very little to no cross-protection is afforded between serotypes of IBV. Therefore, successful vaccination programs must include the serotypes of the prevailing IBV field challenge. Second, IBVs are prone to genetic variation through several distinct genetic mechanisms that may or may not give rise to a new serotype. A few changes in the sequence of the spike glycoprotein can result in a new serotype. It has been documented that as little as a 5% difference in the S1 sequence of IBV can result in a loss of cross-protection between otherwise similar isolates (Cavanagh, 2003, *Avian Pathol;* 32:567-582).

Identifying the type of IBV causing disease in commercial chickens is the first step in controlling this highly infectious virus, but it is of little value if commercially available vaccines do not protect against it. Thus there is a need for the characterization of newly arising IBV variant and the development of vaccines effective against these variants.

SUMMARY OF THE INVENTION

The present invention includes a composition of matter including an S1 glycoprotein subunit having an amino acid sequence having at least 90%, at least 91%, at least 92%, at least 93%, at least 94%, at least 95%, at least 96%, at least 97%, at least 98%, or at least 99% sequence identity to SEQ ID NO:4, SEQ ID NO:5, SEQ ID NO:6, SEQ ID NO:8, SEQ ID NO:10, or SEQ ID NO:12.

In some embodiments, the composition of matter of claim is an isolated infectious bronchitis virus (IBV) having an S1 glycoprotein subunit having an amino acid sequence having at least 90%, at least 91%, at least 92%, at least 93%, at least 94%, at least 95%, at least 96%, at least 97%, at least 98%, or at least 99% sequence identity to SEQ ID NO:4, SEQ ID NO:5, SEQ ID NO:6, SEQ ID NO:8, SEQ ID NO:10, or SEQ ID NO:12. In some embodiments, the isolated infectious bronchitis virus (IBV) is the GA07 isolate, or an attenuated variant thereof. In some embodiments, the isolated infectious bronchitis virus (IBV) is the GA08 isolate, or an attenuated variant thereof. In some embodiments, the isolated infectious bronchitis virus (IBV) virus is attenuated. In some embodiments, the isolated infectious bronchitis virus (IBV) is the E71 attenuated GA08 isolate, GA08/GU301925/08. GA08/pass4/08, GA08/08/08 strain passage 16, GA08/HSp16/08, GA08 isolate 64513, or GA07 isolate 60173.

In some embodiments, the composition of matter is an isolated nucleotide sequence encoding an S1 glycoprotein subunit having an amino acid sequence having at least 90%, at least 91%, at least 92%, at least 93%, at least 94%, at least 95%, at least 96%, at least 97%, at least 98%, or at least 99% sequence identity to SEQ ID NO:4, SEQ ID NO:5, SEQ ID NO:6, SEQ ID NO:8, SEQ ID NO:10, or SEQ ID NO:12. Also included are vectors including one or more such isolated nucleotide sequences and host cells including one or more such isolated nucleotide sequences and/or vectors.

In some embodiments, the composition of matter is an isolated polypeptide having at least 90%, at least 91%, at least 92%, at least 93%, at least 94%, at least 95%, at least 96%, at least 97%, at least 98%, or at least 99% sequence identity to SEQ ID NO:4, SEQ ID NO:5, SEQ ID NO:6, SEQ ID NO:8, SEQ ID NO:10, or SEQ ID NO:12.

The present invention includes a composition of matter including an S1 glycoprotein subunit encoded by a nucleotide sequence acid sequence having at least 90%, at least 91%, at least 92%, at least 93%, at least 94%, at least 95%, at least 96%, at least 97%, at least 98%, or at least 99% sequence identity to SEQ ID NO:1, SEQ ID NO:2, SEQ ID NO:3, SEQ ID NO:7, SEQ ID NO:9, or SEQ ID NO:11.

In some embodiments, the composition of matter is an isolated infectious bronchitis virus (IBV) having an S1 glycoprotein subunit encoded by a nucleotide sequence having at least 90%, at least 91%, at least 92%, at least 93%, at least 94%, at least 95%, at least 96%, at least 97%, at least 98%, or at least 99% sequence identity to SEQ ID NO:1, SEQ ID NO:2, SEQ ID NO:3, SEQ ID NO:7, SEQ ID NO:9, or SEQ ID NO:11. In some embodiments, the isolated infectious bronchitis virus (IBV) is the GA07 isolate, or an attenuated variant thereof. In some embodiments, the isolated infectious bronchitis virus (IBV) is the GA08 isolate, or an attenuated variant thereof. In some embodiments, the isolated infectious bronchitis virus (IBV) virus is attenuated. In some embodiments, the isolated infectious bronchitis virus (IBV) is the E71 attenuated GA08 isolate, GA08/GU301925/08. GA08/pass4/08, GA08/08/08 strain passage 16, GA08/HSp16/08, GA08 isolate 64513, or GA07 isolate 60173. In some embodiments, the composition of matter is an isolated nucleotide sequence having at least 90%, at least 91%, at least 92%, at least 93%, at least 94%, at least 95%, at least 96%, at least 97%, at least 98%, or at least 99% sequence identity to SEQ ID NO:1, SEQ ID NO:2, SEQ ID NO:3, SEQ ID NO:7, SEQ ID NO:9, or SEQ ID NO:11. Also included are vectors including one or more such isolated nucleotide sequences and host cells including one or more such isolated nucleotide sequences and/or vectors.

In some embodiments, the composition of matter is an isolated polypeptide encoded by a nucleotide sequence having at least 90%, at least 91%, at least 92%, at least 93%, at least 94%, at least 95%, at least 96%, at least 97%, at least 98%, or at least 99% sequence identity to SEQ ID NO:1, SEQ ID NO:2, SEQ ID NO:3, SEQ ID NO:7, SEQ ID NO:9, or SEQ ID NO:11.

The present invention includes an antibody that binds to a polypeptide having at least 90%, at least 91%, at least 92%, at least 93%, at least 94%, at least 95%, at least 96%, at least 97%, at least 98%, or at least 99% sequence identity to SEQ ID NO:4, SEQ ID NO:5, SEQ ID NO:6, SEQ ID NO:8, SEQ ID NO:10, or SEQ ID NO:12 or a polypeptide encoded by a nucleotide sequence having at least 90%, at least 91%, at least 92%, at least 93%, at least 94%, at least 95%, at least 96%, at least 97%, at least 98%, or at least 99% sequence identity to SEQ ID NO:1, SEQ ID NO:2, SEQ ID NO:3, SEQ ID NO:7, SEQ ID NO:9, or SEQ ID NO:11. In some embodiments, the antibody does not bind to one or more of the IBV viral isolates HN99, JAAS/04, N1/62, CA/557/03, CAV/CAV1686/95, CA/CA12495/98, CAV/CAV9437/95, Ark, Ark/ArkDPI/81, C2NDV, and/or CU84074. In some embodiments, the antibody is a monoclonal antibody.

The present invention a diagnostic kit including one or more isolated polypeptides of the present invention and/or one or more antibodies of the present invention.

In some embodiments a composition of matter of the present invention is lyophilized.

The present invention includes methods including introducing a one or more of the compositions of matter of the present invention into the body of poultry. In some embodiments, the composition is administered by spraying. In some embodiments, the method further includes the administration of other viral material.

The present invention includes a method of producing an immune response to the IBV virus in poultry, the method including administering one or more of the compositions of matter of the present invention.

The present invention includes a method of preventing an IBV infection in poultry, the method including administering one or more of the compositions of matter of the present invention.

The present invention includes a method of detecting an infectious bronchitis virus (IBV) in a sample, the method including identifying in the sample a nucleotide sequence having at least 90%, at least 91%, at least 92%, at least 93%, at least 94%, at least 95%, at least 96%, at least 97%, at least 98%, or at least 99% sequence identity to SEQ ID NO:1, SEQ ID NO:2, SEQ ID NO:3, SEQ ID NO:7, SEQ ID NO:9, or SEQ ID NO:11.

The present invention includes a method of detecting an infectious bronchitis virus (IBV) in a sample, the method including identifying in the sample an amino acid sequence having at least 90%, at least 91%, at least 92%, at least 93%, at least 94%, at least 95%, at least 96%, at least 97%, at least 98%, or at least 99% sequence identity to SEQ ID NO:4, SEQ ID NO:5, SEQ ID NO:6, SEQ ID NO:8, SEQ ID NO:10, or SEQ ID NO:12.

The terms "comprises" and variations thereof do not have a limiting meaning where these terms appear in the description and claims.

Unless otherwise specified, "a," "an," "the," and "at least one" are used interchangeably and mean one or more than one.

BRIEF DESCRIPTION OF THE FIGURES

FIGS. 1a and 1b. Partial nucleotide (SEQ ID NO:11) and amino acid sequences (SEQ ID NO:12) of the S1 subunit of the spike gene for the attenuated GA08 isolate E71.

FIGS. 2a-2c. The nucleotide (SEQ ID NO:7) and amino acid sequences (SEQ ID NO:8) of the S1 subunit of the spike gene for the heat-treated, attenuated GA08 isolate GA08/HSp16/08.

FIGS. 5a-5c. The nucleotide (SEQ ID NO:9) and amino acid sequence (SEQ ID NO:10) of the S1 subunit of the spike gene for pathogenic avian Infectious Bronchitis Virus (IBV) GA07/GA07/2007GA07.

DETAILED DESCRIPTION OF ILLUSTRATIVE EMBODIMENTS OF THE INVENTION

Figure 3:
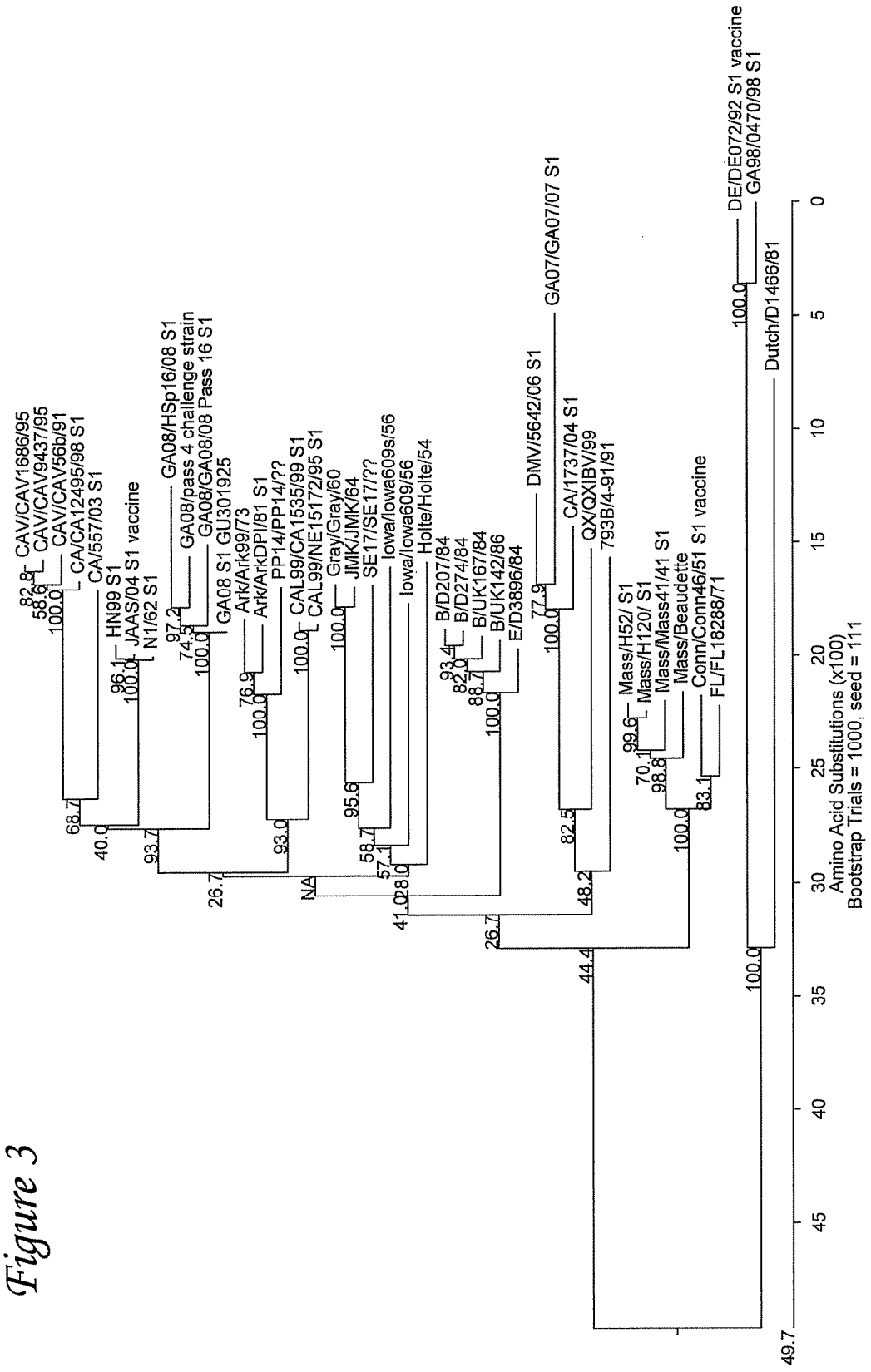
FIG. 3. Phylogenetic tree showing amino acid sequence relatedness of S1 proteins computed using Neighbor-Joining and the Nei-Gojobori method with 1000 bootstrap replicates. The amino acid sequences were aligned with ClustalW (MEGA 4.0.2), and the amino acid substitutions (X100) are shown. GenBank accession numbers are as follows: CAV/1686/95=AF027511, CAV/CAV9437/95=AF027510, CAV/CAV56b/91=AF027509, CA/CA12495/98=AF520604, CA/557/03=DQ912828, HN99=AY775551, JAAS/04=AY839140, N1/62=U29522, GA08/HSp16/08=GU361607, GA08/08/08 pass16=GU734804, GA08/pass4 challenge strain=GU361606, GA08/S1/GU301925=GU301925, Ark/Ark99/73=L10384, Ark/ArkDPI/81=AF006624, PP14/PP14/93=M99483, CAL99/CA1535/99=DQ912831, CAL99/NE15172/95=DQ912832, Holte/Holte/54=L18988, JMK/JMK/64=L14070, Gray/Gray/60=L14069, SE17/SE17/93=M99484, Iowa/Iowa609/56=GU361608, B/D207/84=X58003, B/D274/84=X15832, B/UK167/84=X58065, B/UK142/86=X58066, E/D3896/84=X52084, CAV/CA1737/04=DQ912830, DMV/5642/06=EU694402, QX/IBVQX/99=AF193423, 793B/4-91/91=Z83975, Mass/H52=AF352315, Mass/H120=EU822341, Mass/Mass41/41=AY561711, Mass/Beaudette=M95169, Conn/Conn46/51=L18990, FL/FL18288/71=AF027512, DE/DE072/92=U77298, GA98/CWL470/98=AF274437, Dutch/D1466/81=M21971.

The present invention relates to new materials and methods in the field of poultry virology, particularly in the field of the infectious bronchitis virus, also referred to herein as "IBV," a virus that causes respiratory, reproductive and renal disease in poultry. As is the case with many viruses, the IBV virus has multiple serotypes. More than 20 serotypes within IBV have been recognized worldwide (see, for example, Lee and Jackwood, 2000, Arch Viral; 145:2135-48). IBV can change rapidly in nature to yield variant viruses with new serotypes and causing disease in a susceptible host (Jackwood et al., 2005, Avian Dis; 49(4):614-8). Significant serotype-altered variants arise periodically and are suspected when vaccinated poultry flocks become symptomatic of the disease. Such significant serotype variations in IBV have been characterized in 1962, 1987, 1992 and 1998-99. This application describes the identification, characterization, and attenuation of two new, significant IBV variants, the GA07 and GA08 IBV variants.

The present invention includes isolated GA07 and GA08 infectious bronchitis virus. The original isolates of GA07 and GA08 are virulent, also referred to herein as "pathogenic." That is, poultry, such as chickens, when exposed to such an isolate exhibit one or more of the clinical symptoms of IBV infection. Such GA07 and GA08 isolates may be represented by, for example, any of those described herein, including, but not limited to, GA08/GU301925/08, GA08 isolate 64513, and GA07 isolate 60173.

GA07 IBV viral isolates of the present invention may include IBV viral isolates having the serotype and/or genotype of the GA07 viral isolate described herein. GA08 IBV viral isolates of the present invention may include IBV viral isolates having the serotype and/or genotype of the GA08 viral isolate described herein.

The present invention also includes attenuated isolates of the pathogenic GA07 and GA08 IBV strains. Attenuated isolates demonstrate limiting virulence. The attenuation process is known in the art. For example, attenuated isolates may be obtained by passage through specific pathogen free (SPF) chicken embryos and/or by heat treatment. Examples of such attenuation processes are described herein, and show that the isolates herein may be successfully attenuated. For example, attenuated isolates may be obtained by passaging virulent isolates of the present invention in a culture on a suitable medium a sufficient number of times to reduce its pathogenicity while retaining its immunogenicity. A preferred medium for such passaging is a SPF embryonated egg. Inoculation of the eggs can be via the allantoic cavity, chorioallantoic membrane, yolk sac, amniotic cavity or even direct into the embryo. The virus can be passaged at regular intervals of from 7 hours up to 4 days. Commonly, passaging takes place between 16 to 36 hours, preferably every 24 hours. Alternatively, attenuation may also be achieved by passaging the isolate in avian cell culture, such as chick embryo kidney cells.

Attenuated GA07 and GA08 isolates include, but are not limited to, isolates of either GA07 or GA08 obtained by any of the methods described herein, including, but not limited to, passage through embryonated eggs, as described in Example 4, and heat treatment, as described in Example 7.

Attenuated GA07 and GA08 isolates include, but are not limited to, attenuated isolates obtained by passage of a GA07 or GA08 viral isolate through emryonated eggs. Such isolates may be obtained after, for example, 10 or more passages, 20 or more passages, 50 or more passages, 70 or more passage, or 100 or more passages. Such isolates may be obtained after, for example, with 6 passages (E6), 16 passages (E16), 20 passages (E20), 70 passages, (E70), 71 passages (E71), or any number of passages from 1 to 150 (EN, wherein N is an integer from 1 to 150). Such attenuated GA07 and GA08 isolates include, but are not limited to, any of those described herein, such as, for example, the E71 attenuated GA08 isolate and GA08/HSp16/08.

An IBV isolate of the present invention, pathogenic or attenuated, may be deposited with the American Type Culture Collection (ATCC®) 10801 University Boulevard, Manassas, Va. 20110-2209, USA. Such a deposit may be in accordance with the Budapest Treaty on the International Recognition of the Deposit of Microorganisms for the Purposes of Patent Procedure.

The enveloped IBV virus has a single stranded-positive sense RNA genome that codes for the viral RNA-dependent RNA-polymerase, three major structural proteins (the nucleocapsid, membrane, and spike (S) proteins), and numerous regulatory proteins (Masters, 2006, *Adv Vir Res;* 66:193-292). The spike glycoprotein of IBV is translated as a precursor protein (So) and then cleaved into two subunits, the N-terminal S1 glycoprotein and the C-terminal S2 glycoprotein by host cell serine proteases. The S1 and S2 glycoproteins mediate cell attachment, virus-cell membrane fusion, and play an important role in host cell specificity, forming club shaped projections on the surface of the virus. The S1 glycoprotein induces virus-neutralizing and hemagglutination-inhibiting antibodies.

The IBV virus has multiple serotypes, with more than 20 serotypes within IBV recognized worldwide (Lee and Jackwood, 2000, *Arch Virol;* 145:2135-48). New variant strains arise due to rapid recombination, insertions, deletions, or point mutation events, predominantly in the S1 spike protein gene. Along with the use of serologic based tests, PCR and partial sequencing of the S1 gene can be used to group and type IBV isolates. The sequence from the hypervariable regions of the IBV S1 gene often correlates well with virus neutralization tests and can be reliably used to serotype an IBV isolate (Lee et al., 2003, *J Vet Diagn Invest;* 15:344-348). In the S1 subunit, three hypervariable regions (HVR) have been identified, located within amino acids 38-67, 91-141, and 274-387 (see, for example, Cavanagh et al., 1988, *Virus Res;* 11:141-150; Koch et al., 1990, *J Gen Virol;* 71:1929-1935; and Moore et al., 1997, *Arch Virol;* 142:2249-2256).

The GA07 and GA08 IBV isolates described herein represent two new, genetically distinct groups of IBVs that are not similar to previously known, endemic IBVs. Based on sequence analysis of the S1 region, including the hypervariable regions of S1, each isolates represents a new, unique S1 serotype and S1 genotype in comparison to previously known IBV S1 sequences.

The present invention includes a nucleotide sequence encoding an S1 polypeptide of a S1 serotype and/or genotype defined by the GA07 isolate described herein. Such a nucleotide sequence may be a nucleotide sequence encoding an S1 polypeptide from a pathogenic isolate of GA07, including, but not limited to, a pathogenic GA07 isolate as described here. For example, the present invention includes a nucleotide sequence having SEQ ID NO:1 or SEQ ID NO:9. Such a nucleotide sequence may encode an S1 polypeptide having the amino acid sequence of SEQ ID NO:4 or SEQ ID NO:10. Such a nucleotide sequence encoding an S1 polypeptide may be from an attenuated isolate of GA07, including, but not limited to, a nucleotide sequence encoding an S1 polypeptide of an attenuated GA07 isolate as described here. Such a nucleotide sequence may encode one or more of the three S1 hypervariable regions (for example amino acids 38-67, 91-141, and/or 274-387 of the S1 glycoprotein) of a S1 glycoprotein of a pathogenic or attenuated GA07 isolate as described herein. For example, such a nucleotide sequence may encode one or more of the three S1 hypervariable regions represented by SEQ ID NO:4 or SEQ ID NO:10, such as, for example, amino acids 38-67, 91-141, and/or 274-387 of the S1 glycoprotein represented by SEQ ID NO:4 or SEQ ID NO:10.

The present invention includes a nucleotide sequence encoding an S1 polypeptide of the S1 serotype and/or genotype defined by the GA08 isolate as described herein. Such a nucleotide sequence encoding an S1 polypeptide may be from a pathogenic isolate of GA08, including, but not limited to, a nucleotide sequence encoding an 51 polypeptide of a pathogenic GA08 isolate as described here. For example, the present invention includes a nucleotide sequence having SEQ ID NO:2 or SEQ ID NO:3. Such a nucleotide sequence encoding an 51 polypeptide may be from an attenuated isolate of GA08, including, but not limited to, a nucleotide sequence encoding an S1 polypeptide of an attenuated GA08 isolate as described here, including, but not limited to, a nucleotide sequence encoding an S1 polypeptide of the attenuated GA08 isolate E71 or the heat attenuated GA08 isolate GA08/HSp16/08. For example, the present invention includes a nucleotide sequence having SEQ ID NO:7 (the nucleotide sequence of the S1 subunit of the spike gene for the heat attenuated GA08 isolate GA08/HSp16/08) or SEQ ID NO:11 (the nucleotide sequence of the S1 subunit of the spike gene for the attenuated GA08 isolate E71). Such a nucleotide sequence may encode an S1 polypeptide having the amino acid sequence of SEQ ID NO:5, SEQ ID NO:6, SEQ ID NO:8, or SEQ ID NO:12. Such a nucleotide sequence may encode one or more of the three 51 hypervariable regions of the S1 glycoprotein of an IBV isolated described herein, (for example amino acids 38-67, 91-141, and/or 274-387 of the 51 glycoprotein), including any of the pathogenic or attenuated GA08 isolates described herein, such as for example, the attenuated GA08 isolate E71 or the heat attenuated GA08 isolate GA08/HSp16/08. For example, such a nucleotide sequence may encode one or more of the three S1 hypervariable regions of SEQ ID NO:5, SEQ ID NO:6, SEQ ID NO:8, or SEQ ID NO:12, such as, for example, amino acids 38-67, 91-141, and/or 274-387 of the S1 glycoprotein represented by SEQ ID NO:5, SEQ ID NO:6, SEQ ID NO:8, or SEQ ID NO:12.

The present invention includes polynucleotide sequences with at least about 60% sequence identity, at least about 65% sequence identity, at least about 70% sequence identity, at least about 75% sequence identity, at least about 80% sequence identity, at least about 85% sequence identity, at least about 86% sequence identity, at least about 87% sequence identity, at least about 88% sequence identity, at least about 89% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, or at least about 99% sequence identity to the polynucleotide sequence of SEQ ID NO:1, SEQ ID NO:2, SEQ ID NO:3, SEQ ID NO:7, SEQ ID NO:9, or SEQ ID NO:11. The present invention includes polypeptides encoded by such polynucleotide sequences. Sequence identity may be determined, for example, using BLAST analysis. "BLAST analysis" is intended to mean the nucleotide or protein sequence analysis program available from the United States National Center for Biotechnology, and as described in more detail herein.

The present invention includes polynucleotide sequences that hybridize to the nucleotide sequence of SEQ ID NO:1, SEQ ID NO:2, SEQ ID NO:3, SEQ ID NO:7, SEQ ID NO:9, or SEQ ID NO:11, or a complement thereof, under various stringency conditions, and fragments thereof. Stringency conditions include, but are not limited to, moderate and high stringency. High stringency hybridization conditions may be, for example, 6×SSC, 5× Denhardt, 0.5% sodium dodecyl sulfate (SDS), and 100 µg/ml fragmented and denatured salmon sperm DNA hybridized overnight at 65° C. and washed in 2×SSC, 0.1% SDS at least one time at room temperature for about 10 minutes followed by at least one wash at 65° C. for about 15 minutes followed by at least one wash in 0.2×SSC, 0.1% SDS at room temperature for at least 3 to 5 minutes. The present invention includes polypeptides encoded by such hybridizing polynucleotide sequences.

A polynucleotide sequence may be DNA, RNA, or a modification thereof. A polynucleotide sequence may be single or double stranded, sense (positive) or antisense (negative) sequences.

Also included in the present invention are polynucleotide fragments. A polynucleotide fragment is a portion of an isolated polynucleotide as described herein. Such a portion may be several hundred nucleotides in length, for example about 100, about 200, about 300, about 400, about 500, about 600, or about 700, nucleotides in length. Such a portion may be about 10 nucleotides to about 100 nucleotides in length, including but not limited to, about 14 to about 40 nucleotides in length. Fragments of about 12 to about 100 nucleotides may be used as primers to, for example, amplify all or part of an IBV S1 gene or modify an IBV 51 gene by site-specific mutagenesis. Fragments of about 10 to about 30 nucleic acids can be used, for example, in single stranded forms, double stranded forms, short hairpin RNAs, microRNAs or small interfering RNAs to alter the expression of the an IBV S1 gene by RNA interference or other DICER-mediated mechanisms. Fragments of about 20 to about 1000 nucleotides can be used, for example, in a variety of blot-based assays, including dot blots, northern blots, southern blots, and in situ hybridization assays.

Also included in the present invention are complements of the polynucleotides described herein. As used herein, "complement" and "complementary" refer to the ability of two single stranded polynucleotides to base pair with each other, where an adenine on one polynucleotide will base pair to a thymine on a second polynucleotide and a cytosine on one polynucleotide will base pair to a guanine on a second polynucleotide. Two polynucleotides are complementary to each other when a nucleotide sequence in a polynucleotide can base pair with a nucleotide sequence in a second polynucleotide. For instance, 5'-ATGC and 5'-GCAT are complementary. Typically two polynucleotides are complementary if they hybridize under the standard conditions referred to herein.

The present invention includes polynucleotide sequences having a substitution of one, two, three, four, five, six, seven, eight, nine, ten, or more nucleotides from that of SEQ ID NO:1, SEQ ID NO:2, SEQ ID NO:3, SEQ ID NO:7, SEQ ID NO:9, or SEQ ID NO:11. The present invention also includes the polynucleotide sequences described herein in which codon usage has been adapted to optimize expression in a given host cell. For example, codon usage may be adapted to optimize for expression in host cells including, but not limited to, baculovirus, yeast, E. coli, poultry, or human cells. Such adaptation can be carried out by techniques know in the art.

The present invention provides a recombinant vector containing one or more of the nucleotide sequences described herein. Such a recombinant vector may also include other sequences such as expression control sequences, markers, amplifying genes, signal sequences, promoters, and the like, as is known in the art. Useful vectors for this purpose are plasmids, and viruses such as baculoviruses, paramyxovirus, coronavirus, herpes virus (for example, herpes virus of turkeys (HVT)) and pox viruses, for example, fowl pox virus, and the like. Such a vector may be an expression vector selected for expression in vitro or in vivo or expression in prokaryotic cells or eukaryotic cells. The nucleic acids of the present invention may be used to produce constructs that express antigens. Such antigens may be utilized, for example, to produce antibodies, which may be used for identifying field or laboratory isolates of the present invention.

The present invention also includes host cells transformed with a polynucleotide sequence described herein and host cells transformed with a recombinant vector described herein. The host cell may be, for example, a eukaryotic or a prokaryotic host cell. Suitable examples are E. coli, insect cell lines such as Sf-9, chicken embryo fibroblast (CEF) cells, chicken embryo kidney (CEK) cells, African green monkey Vero cells and the like.

The present invention includes polypeptides having an amino acid sequence of an S1 polypeptide of the S1 serotype and/or genotype defined by a GA07 isolate as described herein. Such an amino acid sequence may be from a pathogenic isolate of GA07, including, but not limited to, a pathogenic GA07 isolate as described herein. For example, the present invention includes a polypeptides having SEQ ID NO:4 or SEQ ID NO:10. Such an amino acid sequence may be from an attenuated isolate of GA07, including, but not limited to, an attenuated GA07 isolate as described herein. Such a polypeptide may include the amino acid sequence of one or more of the three S1 hypervariable regions of the S1 glycoprotein (for example, amino acids 38-67, 91-141, and/or 274-387 of the S1 glycoprotein) of a pathogenic or an attenuated GA07 isolate as described herein. For example, such a polypeptide may include the amino acid sequence of one or more of the three S1 hypervariable regions of the S1 glycoprotein represented by SEQ ID NO:4 or SEQ ID NO:10, such as, for example, including amino acids 38-67, 91-141, and/or 274-387 of the S1 glycoprotein) represented by SEQ ID NO:4 or SEQ ID NO:10.

The present invention includes polypeptides having an amino acid sequence of an S1 polypeptide of the S1 serotype and/or genotype defined by an GA08 isolate as described herein. Such an amino acid sequence may be from a pathogenic isolate of GA08, including, but not limited to, a pathogenic GA08 isolates as described herein. For example, the present invention includes polypeptides having SEQ ID NO:5 or SEQ ID NO:6. Such an amino acid sequence may be from an attenuated isolate of GA08, including, but not limited to, any of the attenuated GA08 isolates described herein, such as for example, an amino acid sequence of an S1 polypeptide of the attenuated GA08 isolates E71 or GA08/HSp16/08. For example, the present invention includes polypeptides having SEQ ID NO:8 (the amino acid sequence of the S1 subunit of the spike gene for the heat attenuated GA08 isolate GA08/HSp16/08) or SEQ ID NO:12 (the amino acid sequence of the S1 subunit of the spike gene for the attenuated GA08 isolate E71). Such a polypeptide may include the amino acid sequence of one or more of the three S1 hypervariable regions of the S1 glycoprotein (for example, amino acids 38-67, 91-141, and 274-387 of the S1 glycoprotein) of a pathogenic or an attenuated GA08 isolate as described herein, such as for example, the attenuated GA08 isolates E71 or GA08/HSp16/08. For example, such a polypeptide may include the amino acid sequence of one or more of the three S1 hypervariable regions of the S1 glycoprotein represented by SEQ ID NO:5, SEQ ID NO:6, SEQ ID NO:8, or SEQ ID NO:12, such as, for example, polypeptides including amino acids 38-67, 91-141, and/or 274-387 of the S1 glycoprotein represented by SEQ ID NO:5, SEQ ID NO:6, SEQ ID NO:8, or SEQ ID NO:12.

"Polypeptide" as used herein refers to a polymer of amino acids and does not refer to a specific length of a polymer of amino acids. Thus, for example, the terms peptide, oligopeptide, protein, and enzyme are included within the definition of polypeptide, whether naturally occurring or synthetically derived, for instance, by recombinant techniques or chemically or enzymatically synthesized. This term also includes post-expression modifications of the polypeptide, for example, glycosylations, acetylations, phosphorylations, and the like.

The present invention includes polypeptides having the amino acid sequence shown in SEQ ID NO:4, SEQ ID NO:5, SEQ ID NO:6, SEQ ID NO:8, SEQ ID NO:10, or SEQ ID NO:12, and truncations and fragments thereof. Truncations include, but are not limited to, amino acid sequences in which one, two, three, four, five, six, or more amino acids are removed from the amino terminus of the amino acid sequence and/or one, two, three, four, five, six, or more amino acids are removed from the carboxy terminus of the amino acid sequence. Fragments include, but are not limited to, for example, fragments having about 5, about 10, about 15, about 20, about 25, about 50, about 75, about 100, about 150, about 200, about 250, about 300, about 350, about 400, about 450, about 500, about 550, about 600, about 650, and about 700 consecutive amino acid residues of the sequence of SEQ ID NO:4, SEQ ID NO:5, SEQ ID NO:6, SEQ ID NO:8, SEQ ID NO:10, or SEQ ID NO:12. Fragments also include, for example, fragments of a size range of any combination of the above fragment sizes. Fragments include, but are not limited to, for example, fragments having at least 5, at least 10, at least 15, at least 20, at least 25, at least 50, at least 75, at least 100, at least 150, at least 200, at least 250, at least 300, at least 350, at least 400, at least 450, at least 500, at least 550, at least 600, at least 650, and at least 700 consecutive amino acid residues of SEQ ID NO:4, SEQ ID NO:5, SEQ ID NO:6, SEQ ID NO:8, SEQ ID NO:10, or SEQ ID NO:12.

The present invention includes polypeptides having an amino acid sequence with one, two, three, four, five, six, seven, eight, nine, ten, eleven, twelve, thirteen, fourteen, fifteen, sixteen, seventeen, eighteen, nineteen, twenty, or more amino acid changes from the amino acid sequence of SEQ ID NO:4, SEQ ID NO:5, SEQ ID NO:6, SEQ ID NO:8, SEQ ID NO:10, or SEQ ID NO:12. Such amino acid changes include, but are not limited to, conservative amino acid changes. As used herein, the term "conservative substitution" refers to the replacement of an amino acid residue by a structurally similar residue. Examples of conservative substitutions include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like.

The present invention includes polypeptides having an amino acid sequence with at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% amino acid sequence similarity with the amino acid sequence of SEQ ID NO:4, SEQ ID NO:5, SEQ ID NO:6, SEQ ID NO:8, SEQ ID NO:10, or SEQ ID NO:12.

The present invention includes polypeptides having an amino acid sequence with at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% amino acid sequence identity with the amino acid sequence of SEQ ID NO:4, SEQ ID NO:5, SEQ ID NO:6, SEQ ID NO:8, SEQ ID NO:10, or SEQ ID NO:12.

As used herein, "structural similarity" refers to the identity between two polypeptides. Structural similarity is generally determined by aligning the residues of the two polypeptides to optimize the number of identical amino acids along the lengths of their sequences; gaps in either or both sequences are permitted in making the alignment in order to optimize the number of identical amino acids, although the amino acids in each sequence must nonetheless remain in their proper order. For example, polypeptides may be compared using the Blastp program of the BLAST 2 search algorithm, as described by Tatusova et al. (FEMS Microbiol. Lett., 174; 247-250, 1999) and available on the world wide web at ncbi.nlm.nih.gov/BLAST/. In the comparison of two amino acid sequences using the BLAST search algorithm, structural similarity may be referred to by percent "identity" or may be referred to by percent "similarity." "Identity" refers to the presence of identical amino acids and "similarity" refers to the presence of not only identical amino acids but also the presence of conservative substitutions.

The present invention includes compositions of matter including or encoding an S1 polypeptide of the same S1 serotype and or S1 genotype as described herein. A composition of matter may be, for example, a virus, a polypeptide, or a nucleotide sequence.

The present invention includes antibodies that bind to a S1 polypeptide, as described herein, and various antibody fragments, also referred to as antigen binding fragments, which include only a portion of an intact antibody, generally including an antigen binding site of the intact antibody and thus retaining the ability to bind antigen.

For example, such an antibody, or antigen binding fragment thereof, may bind to a polypeptide having an amino acid sequence with at least 90% sequence identity, at least about 95% sequence identity to, at least about 98% sequence identity to, or about at least 99% sequence identity to SEQ ID NO:4, SEQ ID NO:5, SEQ ID NO:6, SEQ ID NO:8, SEQ ID NO:10, or SEQ ID NO:12.

Such an antibody, or antigen binding fragment thereof, may bind to a polypeptide having the amino acid sequence of SEQ ID NO:4, SEQ ID NO:5, SEQ ID NO:6, SEQ ID NO:8, SEQ ID NO:10, or SEQ ID NO:12. Such an antibody, or antigen binding fragment thereof, may bind to a polypeptide including at least five, at least ten, at least eleven, at least twelve, at least thirteen, at least fourteen, at least fifteen, at least twenty, at least twenty five, at least thirty, at least forty, at least fifty, at least seventy-five, at least one hundred, at least two hundred, at least three hundred, at least four hundred, at least five hundred, at least six hundred, or at least seven hundred consecutive amino acid residues of SEQ ID NO:4, SEQ ID NO:5, SEQ ID NO:6, SEQ ID NO:8, SEQ ID NO:10, or SEQ ID NO:12.

In some embodiments, while binding to an amino acid sequence of an S1 polypeptide as described herein, or a fragment thereof, such an antibody may not bind to a previously known IBV isolate. Such a previously known isolate of IBV may include HN99, JAAS/04, N1/62, CA/557/03, CAV/CAV1686/95, CA/CA12495/98, CAV/CAV9437/95, Ark, Ark/ArkDPI/81, C2NDV, CU84074, CAV/CAV56b/91, CA/CA12495/98, Ark/Ark99/73, PP14/PP14/93, CAL99/CA 1535/99, CAL99/NE15172/95, Holte/Holte/54, JMK/JMK/64, Gray/Gray/60, SE17/SE17/93, Iowa/Iowa609/56, B/D207/84, B/UK167/84, B/UK142/86, E/D3896/84, CAV/CA1737/04, DMV/5642/06, QX/IBVQX/99, 793B/4-91/91, Mass/H52, Mass/H120, Mass/Mass41/41, Mass/Beaudette, Conn/Conn46/51, FL/FL18288/71, DE/DE072/92, GA98/CWL470/98, or Dutch/D1466/81.

Examples of antibody fragments include, for example, Fab, Fab', Fd, Fd', Fv, dAB, and F(ab')2 fragments produced by proteolytic digestion and/or reducing disulfide bridges and fragments produced from an Fab expression library. Antibodies include, but are not limited to, polyclonal antibodies and monoclonal antibodies. The antibodies of the present invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Immunoglobulins can have both heavy and light chains. An array of IgG, IgE, IgM, IgD, IgA, and IgY heavy chains can be paired with a light chain of the kappa or lambda form.

The antibodies of the invention can be from any animal origin, including birds and mammals. In some embodiments, the antibodies are human, murine, rat, donkey, sheep, rabbit, goat, guinea pig, camel, horse, or chicken antibodies. As used herein, "human" antibodies include antibodies having the amino acid sequence of a human immunoglobulin and include antibodies isolated from human immunoglobulin libraries or from animals transgenic for one or more human immunoglobulins.

Monoclonal antibodies of the present invention can be obtained by various techniques familiar to those skilled in the art. For example, spleen cells from an animal immunized with a desired antigen are immortalized, commonly by fusion with a myeloma cell. Monoclonal antibodies can be isolated and purified from hybridoma cultures by techniques well known in the art. Other known methods of producing transformed B cell lines that produce monoclonal antibodies may also be used. In some embodiments, the antibody can be recombinantly produced, for example, produced by phage display or by combinatorial methods. Such methods can be used to generate human monoclonal antibodies.

Also included in the present invention are hybridoma cell lines, transformed B cell lines, and host cells that produce the monoclonal antibodies of the present invention; the progeny or derivatives of these hybridomas, transformed B cell lines, and host cells; and equivalent or similar hybridomas, transformed B cell lines, and host cells.

The present invention includes isolated viruses, polypeptides, polynucleotides, and antibodies. As used herein, "isolated" refers to material removed from its original environment (e.g., the natural environment if it is naturally occurring), and thus is altered "by the hand of man" from its natural state. Viruses, polypeptides, polynucleotides, antibodies, and compositions thereof of the present invention may be stored until use in any of a variety of forms. For example, such materials, including, but not limited to, attenuated viral material, may be lyophilized and may be rehydrated for use. In another embodiment, materials may be frozen.

The present invention includes kits employing one or more of the viruses, polypeptides, polynucleotides, and/or antibodies described herein. Such kits may provide for the administration of a polypeptide or polynucleotide of the present invention to an animal in order to elicit an immune response. Such kits may provide for the detection of a polypeptide, antibody or polynucleotide, for example, for the detection of IBV infection or exposure to an IBV agent in an animal. Kits of the present invention may include other reagents such as buffers and solutions needed to practice the invention are also included. Optionally associated with such container(s) can be a notice or printed instructions. As used herein, the phrase "packaging material" refers to one or more physical structures used to house the contents of the kit. The packaging material is constructed by well known methods, preferably to provide a sterile, contaminant-free environment. As used herein, the term "package" refers to a solid matrix or material such as glass, plastic, paper, foil, and the like, capable of holding within fixed limits a polypeptide. Kits of the present invention may also include instructions for use. Instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

In one embodiment, the present invention includes a process for the preparation of live attenuated infectious bronchitis vaccine from a poultry virus isolate herein. Such a process may include one or more of the steps of passaging a poultry virus isolate herein in a culture on a suitable medium for sufficient number of times to reduce its pathogenicity while retaining its immunogenicity, heat treating the passaged culture, and/or harvesting the attenuated materials, wherein the material is of the same S1 serotype and/or S1 genotype as described herein.

The viruses, polypeptides, polynucleotides, vectors, host cells, and compositions of the present invention may be administered to poultry or other animals to elicit an immune response to IBV virus and/or an IBV S1 polypeptide of the S1 serotype and/or genotype defined by the GA08 isolate or the GA07 isolate. The immune response may or may not confer protective immunity. Such an immune response may result in a reduction or mitigation of the symptoms of future IBV infection. Such an immune response may prevent a future RSS infection in poultry. Such an immune response may be a humoral immune response, a cellular immune response, and/or a mucosal immune response. A humoral immune response may include an IgG, IgM, IgA, IgD, and/or IgE response. The determination of a humoral, cellular, or mucosal immune response may be determined by any of a variety of methods, including, but not limited to, any of those described herein.

Vaccination for IBV is common for most commercial chickens. The vaccines are usually modified-live virus vaccines delivered through mass aerosol applications. The serotypes used in vaccination are often selected based on what serotypes the birds may be exposed to in the field. There is very little cross-protection between different serotypes of IBV. Accordingly, it is an object of the present invention to provide immunological materials that do not result in significant clinical signs or lesions indicative of IBV disease. It is another object to provide immunological materials of low virulence. It is another object to provide immunological materials with no increase in virulence when back passaged. It is another object to provide immunological materials that prevent infection with virulent wild type strains of IBV.

The viruses, polypeptides, polynucleotides, vectors, host cells, and compositions of the present invention may be administered to poultry or other animals as vaccines that reduce the susceptibility to disease induced by IBV. With such administration, the materials do not result in significant clinical signs or lesions indicative of IBV infection. Such animals may demonstrate circulating antibodies to IBV and/or reduced symptoms of IBV. Such compositions of matter may serve as vaccines that protect the birds from disease induced by IBV.

Compositions and vaccines of the present invention may include, for example, water or culture medium. Such compositions and vaccines may include pharmaceutically acceptable carriers or diluents. Carriers include, for example, stabilizers, preservatives and buffers. Suitable stabilizers include, for example, SPGA, carbohydrates (such as sorbitol, mannitol, starch, sucrose, dextran, glutamate or glucose), proteins (such as dried milk serum, albumin or casein) or degradation products thereof. Suitable buffers include, for example, alkali metal phosphates. Suitable preservatives include, for example, thimerosal, merthiolate and gentamicin. Diluents, include, but are not limited to, water, aqueous buffer (such as buffered saline), alcohols, and polyols (such as glycerol).

Compositions of matter of the present invention may be substantially pure. As used herein, "substantially pure" will mean material essentially free of any similar macromolecules or other biological entities that would normally be found with it in nature. In some embodiments, the organisms used in such formulations are live. In some embodiments, the organisms, compositions, or vaccines may be lyophilized.

Immunogenic compositions and vaccines of the present invention may be administered to birds of any of a variety of avian species that are susceptible to IBV infection, including, but not limited to, poultry, birds of the order Galliformes, and exotic bird species. Birds of the order Galliformes include, but are not limited to, chickens, turkeys, grouse, quails, and pheasants. As used herein, poultry includes domesticated birds that are kept for the purpose of collecting their eggs, or killing for their meat and/or feathers. These most typically are members of the superorder Galloanserae (fowl), especially the order Galliformes (which includes, for example, chickens, quail, turkeys, and grouse) and the family Anatidae (in order Anseriformes), commonly known as "waterfowl" (including, for example, ducks, geese, and swans). Poultry may also include other birds which are killed for their meat, such as pigeons or doves or birds considered to be game, like pheasants.

"Poultry" is intended to embrace any breed of chicken, pheasant, emu, ostrich and other type of bird that is susceptible to infection by IBV. Chickens include, but are not limited to, hens, roosters, broilers, roasters, layers, breeders, the offspring of breeder hens, and layers. In some embodiments, the compositions of matter and methods of the present invention also apply to animals other than poultry that are susceptible to infection with IBV. As used herein, the term "susceptible to" means the possibility or actuality of a detrimental response to the referenced microorganism, such as, for example, reduced vigor or a failure to thrive, when compared to a non-susceptible individuals or groups, and/or one or more pathological state(s) indicative of an IBV infection, including, but not limited to, any of those described herein.

Compositions and vaccines of the present invention may be formulated for delivery by any of a variety of routes known in the veterinary arts, such as for example, mucosal, intranasal, intraocular, or oral administration. Compositions and vaccines of the present invention may be formulated for delivery to the respiratory mucosa and may be administered such that it is immediately or eventually brought into contact with the bird's respiratory mucosal membranes. Compositions and vaccines of the present invention may be formulated for delivery by any of a variety of modes known in the veterinary arts, such as for example, spraying or aerolizing.

An immunogenic composition or vaccine of the present invention may be administered by any suitable known method of inoculating birds including, but not limited to, nasally, ophthalmically, by injection, in drinking water, in the feed, by exposure, in ovo, maternally, and the like.

The immunogenic composition or vaccine may be administered by mass administration techniques such as by placing the vaccine in drinking water or by spraying the animals' environment. A composition may be administered by spraying an individual or the flock with a solution, such aerosol delivery may involve the administration of the composition incorporated in small liquid particles. Such spray-type particles may have a droplet size ranging from between about 10 to about 100 microns, more preferably, a droplet size from between about <1 to about 50 microns. For the generation of the small particles, conventional spray-apparatus and aerosol generators may be used, such as the commercially available spray generators for knapsack spray, hatchery spray and atomist spray. Administration through drinking water may can be carried out using conventional apparatus. When administered by injection, the immunogenic composition or vaccine may be administered parenterally. Parenteral administration includes, for example, administration by intravenous, subcutaneous, intramuscular, or intraperitoneal injection.

A composition or vaccine of the present invention may be administered to birds before or after hatching. Birds may receive such a composition of vaccine at any of a variety of ages. With delivery after hatching, materials may be delivered, for example, about one week after hatching, about two weeks after hatching, about three weeks after hatching, about four weeks after hatching, about five weeks after hatching, about six weeks after hatching, or any range thereof. For in ovo administration, materials may be delivered about seventeen days of incubation, about eighteen days of incubation, about nineteen days of incubation, about twenty days of incubation, and any range thereof.

An immunogenic composition or vaccine of the present invention may further include one or more immunogens derived from other pathogens infectious to poultry. Such immunogens may be derived from, for example, Marek's disease virus (MDV), other serotypes of infectious bronchitis virus (IBV), including, but not limited to, any of those described herein, Newcastle disease virus (NDV), egg drop syndrome (EDS) virus, turkey rhinotracheitis virus (TRTV), poxvirus, or reovirus.

The viruses, polypeptides, polynucleotides, vectors, host cells, and antibodies of the present invention may be utilized in any of the commonly used methods for IBV detection, such as, for example, hemagglutination (HA) (Lashgari and Newman, 1984, *Avian Dis;* 28:435-443), hemagglutination inhibition (King and Hopkins, 1983, *Avian Dis;* 27:100-112), AGPT (Lohr, 1980, *Avian Dis;* 24:463-467; and Lohr 1981, *Avian Dis;* 25:1058-1064), and RT-PCR (Kwon et al., 1993, *Avian Dis;* 37:194-202).

The present invention also includes methods for the detection of IBV isolates, the identification of IBV serotypes, the detection of IBV genotypes, and the detection of antibodies to IBV, including the detection of an IBV infection or the detection of previous exposure of an animal to IBV, wherein the IBV virus is of the S1 serotype and/or genotype defined by the GA08 isolate or the GA07 isolate. Such a method may employ determining that an antisera sample includes antibodies that specifically bind to a polypeptide of the present invention. Such a method may employ detecting the hybridization of a polynucleotide of the present invention to a sample, preferably under high stringency conditions. Such a method may employ producing a polymerase chain reaction (PCR) amplification, where the resultant amplicon demonstrates a sequence similar to a nucleotide sequence of the present invention. Such a method may employ producing a polymerase chain reaction (PCR) amplification utilizing a primer pair described herein. The polypeptides, polynucleotides, and/or antibodies may be labeled with one or more of the detectable markers known to the skilled artisan. In some aspects, the polypeptides, polynucleotides, and/or antibodies may be bound to a solid substrate.

Antibodies may be detected by any of a variety of methods, including, but not limited to, the methods described herein and any suitable method available to the skilled artisan. Immunoassays that can be used include, but are not limited to, competitive and non-competitive assay systems using techniques such as BIAcore analysis, FACS (Fluorescence activated cell sorter) analysis, immunofluorescence, immunocytochemistry, Western blots, radio-immunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art.

In some embodiments, primers, including, but not limited to any of those described herein, may be used in PCR to amplify the nucleotide sequence encoding a S1 glycoprotein from a sample, and the products compared via sequence analysis or hybridization, to nucleic acid sequence described herein, to identify an MY virus of the S1 serotype and/or genotype defined by the GA08 isolate or the GA07 isolate.

Any of the diagnostic methods of the present invention may include the additional step of providing a report or print out of the results. The sample may be any sample in which IBV antibodies, viruses, antigens, or nucleotides are present, for example, a blood, serum or tissue sample. Such methods and kits may also provide for the detection of infectious IBV agents in environmental samples.

While the invention has been described in connection with specific embodiments, it will be understood that it is capable of further modifications and the appended Claims are intended to cover any variations, uses, or adaptations of the invention following, in general, the principles of the invention and including such departures from the present disclosure as come within known or customary practice within the, art to which the invention pertains and as may be applied to the essential features hereinbefore set forth whether now existing or after arising.

The present invention is illustrated by the following examples. It is to be understood that the particular examples, materials, amounts, and procedures are to be interpreted broadly in accordance with the scope and spirit of the invention as set forth herein.

EXAMPLES

Example 1

Isolation and Characterization of Nephrotropic and Variant Infectious Bronchitis Virus Isolates from Georgia Between May and August, severe flushing in 25-35 day-old broilers was reported on several farms in Northeast Georgia. Kidneys were submitted for histopathology and virus isolation. Histologic evaluation of the kidneys from affected flocks revealed lesions suggestive of nephropathogenic IBV. In addition, IBV was isolated from the kidneys. As with all clinical IBV isolations, molecular characterization was performed using PCR to amplify a region within the S1 subunit of the spike glycoprotein. It has been well documented that the sequence of the hypervariable region of the IBV S1 gene correlates well with virus neutralization tests and can be reliably used to type IBV isolates (Lee et al., 2003, *J Vet Diagn Invest;* 15:344-348). The amino acid sequences of the field isolates from these flocks were 85% similar to NIBV isolates from Australia, specifically the N1-62 strain. The closest match to any U.S. commercial vaccine, was to MASS (80% similar). Cross neutralization studies in SPF embryos using several of these recent isolates in combination with the US vaccine strains (MASS, Conn, DE072 and ARK) showed little to no neutralization, suggesting these viruses are antigenically unrelated. Based on this information it was concluded that the isolates were likely a new serotype of IBV. In November, a similar case was submitted to the lab from 33 week old broiler breeder hens. IBV was isolated from the kidneys and characterization of the virus revealed its high degree of similarity (98%) to the isolates from the summer (GA07 viruses). No additional reports of severe flushing or variant IBV isolations were made for several months. This group of viruses is referred to as GA07.

In January of the next year, additional clinical cases were submitted to the diagnostic lab from approximately 35 day old broiler flocks. Clinical signs ranging from excessive flushing, to respiratory disease, to a combination of the two have been reported in these flocks. In many of the affected flocks, excessive mortality often accompanies the clinical signs. Most of the mortality appears to be from secondary issues, such as *E. coli* infections, following the original viral infection. Oftentimes elevated mortality is accompanied by high condemnations at the processing plant due to airsacculitis. The airsacculitis ranges from a mild "sudsy" airsacculitis to a more chronic appearing caseous airsacculitis. In two cases submitted with a primary complaint of severe flushing, IBVs were isolated from the kidneys. In addition to histologic lesions suggestive of NIBV, molecular characterization of the viruses resulted in 98% similarity with IBV isolates from the summer of 2007. In addition, a second distinct group of IBVs was isolated from either the tracheas or kidneys or both on farms with respiratory disease and high condemnations.

Molecular characterization of this group of viruses reveals an 83% amino acid similarity to the GA07 IBVs, 80% similarity to MASS and 87% similarity to NIBV N1-62. This group of viruses is referred to as GA08.

While serological evaluation of GA08 flocks using IBV ELISA detected positive geometric mean titers (GMT), the serotype specific hemagglutination inhibition (HI) results were inconclusive. Attempts to produce HI antigen to the new serotypes of IBV were not successful as these isolates do not hemagglutinate chicken red blood cells following treatment with neuraminidase. These viruses replicate in primary chicken embryo kidney cells causing characteristic IBV cytopathic effect and thus it may be possible to perform virus neutralization characterization.

With this example, two genetically distinct groups of IBVs have been isolated from vaccinated broilers experiencing renal and respiratory disease. The isolates are not similar to endemic IBVs in the U.S. based on sequence analysis of the hypervariable region of S1. This example has also published as Sellers et al., March/April 2008, *The Poultry Informed Professional;* 98:1-4.

Example 2

Isolate Identification and Characterization

Tracheas and kidneys from flocks in the field were obtained. Generally, "GA07 IBV" was isolated from IBV-vaccinated flocks exhibiting severe mortality and flushing at approximately 28-35 days of age. "GA08 IBV" was isolated from IBV-vaccinated flocks wherein the primary clinical complaint was airsacculitis either on the farm or at the processing plant, resulting in high condemnations. Viral material isolation was performed in 9-11 day old specific pathogen free embryos inoculated by the chorioallantoic sac. At 48 hours post inoculation (embryo passage 1, E1), allantoic fluid was aseptically removed and tested for hemagglutination activity (HA) with 5% chicken red blood cells (CRBC). Additionally, allantoic fluid was treated with 10 UIml type V Neuraminidase and incubated at 37° C. for 30 minutes. Following incubation, neuraminidase-treated allantoic fluid was tested for HA activity with 5% CRBCs. Neither untreated or treated allantoic fluid hemagglutinated CRBCs. Allantoic fluid from this passage was passed into a second set of 9-11 day-of embryonation SPFs embryos (embryo passage 2, E2). As with E1, the E2 passage was tested for HA with CRBCs with and without neuraminidase treatment. The E2 passage was negative for HA. Passaging of the samples was carried out to E5 for GA07 isolate (60173) and to E4 for the GA08 isolate (64513). Embryo viability was examined on a daily basis and mortality documented. In addition, at 7 days post inoculation, all embryo passages were opened and evaluated for IBV-specific lesions such as embryo stunting, curled toes, clubbed down, presence of kidney mates. Suspect infectious bronchitis virus isolation was based on embryo lesions and mortality patterns which were consistent with IBV. As described in Example 3, confirmation and characterization of IBV isolates GA07 and GA08 was performed using RT-PCR of a region of the spike glycoprotein, S1 subunit.

Example 3

Genetic Characterization of GA07 and GA08 IBV

Allantoic fluid from embryo passages consistent with IBV isolation were further tested for IBV by RT-PCR of the S1 gene. Primers used for amplification were 5' ACTG-GCAATTTTTTCAGA 3' (SEQ ID NO:13) (IBV LC forward); and 5' ACAGATTGCTTGCAACCAC 3' (SEQ ID NO:14) (IBV LC reverse). This primer pair has been shown to amplify the S1 gene between hypervariable region 1 and 2, yielding an intended product of 348 bp. Additionally, an 800 bp product (not the intended 348 bp) was observed for several isolates due to the phenomenon of mispriming downstream of intended reverse primer location which has been observed on occasion.

Sequence analysis of either product confirmed presence of IBV nucleic acid in allantoic fluid from suspect embryos. In addition, BLAST analysis of GA07 IBV isolates with IBV S1 sequences available on GenBank revealed the highest similarity of nucleotide sequence (at 86-88%) to a nephropathogenic IBV isolated in Australia. Similarity to current U.S. commercial vaccines (at the nucleotide level) was between 80-83%. Sequence analysis of the nucleotide sequence of GA08 isolates with public domain sequences resulted in an 85-88% similarity to a variant IBV isolate called CU84074. Multiple GA07 and GA08 isolates were taken from multiple flocks, with phylogenetic analysis revealing a high degree of similarity within each GA07 and GA08 group (98-100%). The isolation of these variant strains of IBV from multiple flocks of chickens are not similar to endemic strains of IBV in the U.S. It has been well established that the sequence of the S1 gene (nucleotide and amino acid) correlates well with serotype.

For the GA07 isolate, the following partial S1 LC glycoprotein-encoding nucleic acid sequence was obtained:

```
                                              (SEQ ID NO: 1)
CTGGCAATTTTTTCAGATGGATTATACCCTTTTACTAATAATACTTTAG

TAAAACAGAAGTTCATTGTTTATCGGGAGAATAGTGTTAATACCACTTT

GGTTTTGCATAATTTTACTTTTAGTAATGAGACTAATGCACAACCTAAT

ACAGGTGGTGTTCATACTATTAAGTTATATCAAACACGTACAGCTCAGA

GTGGTTATTATAATTTTAATTTTTCCTTTCTGAGTGGTTTTGTCTATAA

GGAGTCTAATTTTATGTATGGATCTTATCACCCAAGTTGTAAGTTTAGA

CCAGAAACTATTAATAATGGTTTGTGGTTTAATTCACTTCAGTTTCACT

TGCATATGGCCCCCCTTCAAGGTGGTTGCAAGCAATCTGTAA.
```

For the GA08 isolate, the following partial S1 LC glycoprotein-encoding nucleic acid sequence was obtained:

```
                                              (SEQ ID NO: 2)
GGAAAGTTTATTGTTTATCGTGAGAATAGTATTAATACCACTTTGGTTT

TACATAATTTTACGTTTCATAATGAAAGCAATGCACAACCTAATCTTGG
```

TGGTGTTAATAACATTGCWATTTATCAAACACAAACAGCTCAGAGTGGC

TATTATAATTTTAATTTCTCATTTCTGAGTAGTTTTGTTTATAAGTCAA

GTGATTTTATGTATGGGTCTTTTCACCCACAGTGTAGTTTTAGACCAGA

AAACATTAATAATGGGCTCTGGTTCAATTCACTTTCAATTTCACTTGCT

TACGGCCCACTACAAGGGGGCTGTAAACAGTCAGTTTTTAGTCGCAAAA

CAACGTGTTGTTATGCTTATTCATATGGCGGTCCTCATTTGTGTAAAGG

TGTTTATGCAGGTGAGTTAACAAAGAATTTTGAATGTGGCTTGTTAGTT

TATATTACTAAGAGTGAGTGATGGTTCTCGTATACAAACGGCAACAGAA

GCACCTGTAGTAACCACAAATTTTTACAATAACATTACTTTGAATAAGT

GTGTTGAGTATAATATACGGTAGAATTGGCCAAGGTTTTATTACTAA

TGTAACTGATTTAGCTTCTAGTTACAATTATCTGGCAGACGGTGGACTA

GCTATTTTAGACACATCTGGTGCCATAGATATCTTCGTTGTACACCCTT

GTGAAGATGTTAACCAACAGTTTGTAGTGTCAG.

Further, the following GA08 full-length S1 glycoprotein nucleic acid sequence was obtained:

(SEQ ID NO: 3)
ATGTTGGGGAAGTCACTGTTTTTAGTGACCATTTTGTTTGCACTATGTA

GTGCTAATTTATATGATAATAATTCTTTTGTGTATTACTACCAGAGTGC

TTTTAGGCCAGGACTTGGTTGGCATTTACATGGAGGTGCTTATGCAGTA

GTTAATGTGTCTTCTGAAACTAATAATGCAGGCTCCTCATCTTCTTGCA

CTGCTGGTGCTATTTATTGGAGTAAAAATTTTAGTGCAGCTTCTGTAGC

CATGACTGCACCAGATTCTGGTATGTTATGGTCTGCAAACCAATTTTGT

ACGGCCCACTGCAATTTTACTAGTTTTACAGTGTTTGTTACACATTGTT

TTAAGTCAGGTGCCAAGGAGTGTCCTTTGACTGGTCTGATTCAAAAGGG

TTATCTTCGCATTGCCGCTATGAAACAAAACGGTAGTGGGCCTGCTGAC

TTATTTTATAATTTAACAGTTCCAGTGACTAAATACCCTGTGTTTAGAT

CACTTCAATGTGTTAATAATCAAACATCTGTATATTTAAATGGTGATCT

TGTTTTTACTTCTAATGAGACTATTGATGTCTCAGGTGCTGGTGTTCAT

TTTAAAGCTGGTGGACCTATAACTTATAAAGTTATGAGAGAAGTAAAAG

CTTTGGCTTATTTTGTTAATGGTACTGCACAAGATGTTATTCTTTGTGA

TGAGTCACCTAGAGGTTTGTTAGCATGCCAATATAATACTGGCAATTTT

TCAGATGGCTTCTATCCTTTTACTAATTCTAGTTTAGTTAAGGAAAAGT

TTATTGTTTATCGTGAGAATAGTATTAATACCACTTTGGTTTTACATAA

TTTTACGTTTCATAATGAAAGCAATGCACAACCTAATCTTGGTGGTGTT

AATAACATTGCTATTTATCAAACACAAACAGCTCAGAGTGGCTATTATA

ATTTTAATTTCTCATTTCTGAGTAGTTTTGTTTATAAGTCAAGTGATTT

TATGTATGGGTCTTTTCACCCACAGTGTAGTTTTAGACCAGAAAACATT

AATAATGGGCTCTGGTTCAATTCACTTTCAATTTCACTTGCTTACGGCC

CACTACAAGGGGGCTGTAAACAGTCAGTTTTTAGTCGCAAAACAACGTG

TTGTTATGCTTATTCATATGGCGGTCCTCATTTGTGTAAAGGTGTTTAT

GCAGGTGAGTTAACAAAGAATTTTGAATGTGGCTTGTTAGTTTATATTA

CTAAGAGTGATGGTTCTCGTATACAAACGGCAACAGAAGCACCTGTAGT

AACCACAAATTTTTACAATAACATTACTTTGAATAAGTGTGTTGAGTAT

AATATATACGGTAGAATTGGCCAAGGTTTTATTACTAATGTAACTGATT

TAGCTTCTAGTTACAATTATCTGGCAGACGGTGGACTAGCTATTTTAGA

CACATCTGGTGCCATAGATATCTTCGTTGTACAAGGTGAATATGGTTTT

AATTATTATAAGGTTAACCCTTGTGAAGATGTTAACCAACAGTTTGTAG

TGTCAGGTGGTAATATAGTTGGCATTCTTACTTCACGTAATGAAACTGA

TTCTCAGCCTCTTGAAAATCAGTTTTATATTAAGTTAACTAATGGAAGT

CGTCGTTCTAG.

The following partial S1 LC glycoprotein amino acid sequence is deduced from the GA07 nucleotide sequence of SEQ ID NO:1:

(SEQ ID NO: 4)
LAIFSDGLYPFTNNTLVKQKFIVYRENSVNTTLVLHNFTFSNETNAQPN

TGGVHTIKLYQTRTAQSGYYNFNFSFLSGFVYKESNFMYGSYHPSCKFR

PETINNGLWFNSLQFHLHMAPFKVVASNL.

The following partial S1 LC glycoprotein amino acid sequence is deduced from the GA08 nucleotide sequence SEQ ID NO:2:

(SEQ ID NO: 5)
GKFIVYRENSINTTLVLHNFTFHNESNAQPNLGGVNNIAIYQTQTAQSG

YYNFNFSFLSSFVYKSSDFMYGSFHPQCSFRPENINNGLWFNSLSISLA

YGPLQGGCKQSVFSRKTTCCYAYSYGGPHLCKGVYAGELTKNFECGLLV

YITKSDGSRIQTATEAPVVTTNFYNNITLNKCVEYNIYGRIGQGFITNV

TDLASSYNYLADGGLAILDTSGAIDIFVVQGEYGFNYYKVNPCEDVNQQ

FVVS.

And, the following GA08 full length S1 glycoprotein amino acid sequence (start codon to stop codon) is deduced from the nucleotide sequence SEQ ID NO:4:

(SEQ ID NO: 6)
MLGKSLFLVTILFALCSANLYDNNSFVYYYQSAFRPGLGWHLHGGAYAV

VNVSSETNNAGSSSSCTAGAIYWSKNFSAASVAMTAPDSGMLWSANQFC

TAHCNFTSFTVFVTHCFKSGAKECPLTGLIQKGYLRIAAMKQNGSGPAD

LFYNLTVPVTKYPVFRSLQCVNNQTSVYLNGDLVFTSNETIDVSGAGVH

FKAGGPITYKVMREVKALAYFVNGTAQDVILCDESPRGLLACQYNTGNF

SDGFYPFTNSSLVKEKFIVYRENSINTTLVLHNFTFHNESNAQPNLGGV

NNIAIYQTQTAQSGYYNFNFSFLSSFVYKSSDFMYGSFHPQCSFRPENI

NNGLWFNSLSISLAYGPLQGGCKQSVFSRKTTCCYAYSYGGPHLCKGVY

AGELTKNFECGLLVYITKSDGSRIQTATEAPVVTTNFYNNITLNKCVEY

NIYGRIGQGFITNVTDLASSYNYLADGGLAILDTSGAIDIFVVQGEYGF

NYYKVNPCEDVNQQFVVSGGNIVGILTSRNETDSQPLENQFYIKLTNGS

RRS.

Example 4

Attenuation of IBV Isolates

While many isolates within each group (GA07 and GA08) were identified according to the processes herein, representative isolates were selected for attenuation (continued passage to reduce pathogenicity) in chicken embryos for a live virus vaccine master seed production.

The embryo passage for isolates was continued in successive embryo passages in 9-11 day old embryos inoculated via the chorioallantoic sac (CAS) route of inoculation. Allantoic fluid was harvested between 32-36 hours post-inoculation and subsequently passed in 9-11 day old embryos as before. Every tenth passage, additional embryos were inoculated and incubated out to the seventh day post inoculation and at that time, opened for visual examination of embryos. Additionally, allantoic fluid from every 10th passage was tested by RT-PCR of the IBV S1 LC region followed by sequence analysis to confirm the presence of the original IBV isolate. At the 50th embryo passage, allantoic fluid was collected and saved for further passage as well as, titrated in 9-11 day old embryos, viral titer was determined using the method of Reed and Meunch resulting in representation of virus concentration in embryo infective dose 50 (EID50). Titrated viruses was safety tested in 2 week-old chickens. Two week old broilers or SPF chickens were challenged according to procedures outlined in the 9 CFR (Code of Federal Regulations). When the embryo passage that was considered attenuated had been safety tested, viral stock was then tested for extraneous viral and bacterial agents, propagated as before, and titrated in chicken embryos.

Figure 1:
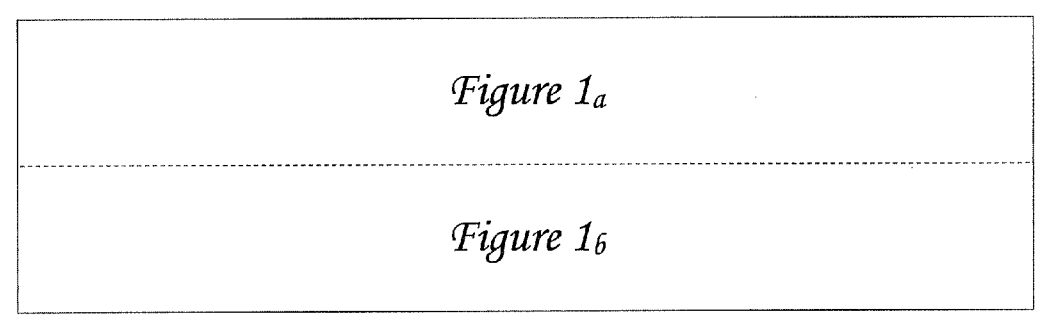

One resultant, live attenuated GA08 isolate was the E71 isolate. The partial nucleotide sequence (SEQ ID NO:11) and amino acid sequence (SEQ ID NO:12) of the S1 glycoprotein of the attenuated GA08 isolate E71 are shown in FIG. 1.

Example 5

Backpassage in Chicks

The attenuated GA08 IBV isolate E71 was backpassaged in commercial broiler chicks between 1-5 days of age, as shown in Table 1. Day-old, nonvaccinated commercial broilers were obtained. For the BP #1, ten one-day-old chicks were inoculated via eye drop with the attenuated GA08 at $10^4$ EID50/bird. The negative control group (n=10) was inoculated with 100 ul of sterile PBS. At 5 days post inoculation, tracheal swabs were collected from each bird and pooled (by treatment group) in sterile PBS. Birds were euthanized and tracheas harvested and fixed in formalin per group. For BP #2-10, 50 ul of swab supernatant from 1) GA08 and 2) negative controls was used to inoculate the next group of chicks via the trachea. At 5 days post inoculation, tracheal swabs were collected from each bird and pooled (by treatment group) in sterile PBS. Birds were euthanized and tracheas harvested and fixed in formalin by group. Histological scoring on cross and longitudinal trachea sections was performed. Routine IBV PCR was used to evaluate tracheal swabs from GA08 groups at each backpassage.

Sequencing of IBV PCR products was performed on Backpassages #1 and #5. No clinical signs or significant macroscopic lesions were observed in any of the backpassages #1-10 at 5 days post inoculation. No significant difference in tracheal lesion scores were observed between vaccinates and negative controls. Tracheal lesion scores were mild (<2.2) in all groups at each backpassage. IBV was detected by RT PCR in swabs from each GA08 group in BP #1-6. No IBV was detected in tracheal swabs from BP #7-10. The GA08 live attenuated vaccine (E71) is stably attenuated and does not pose the risk of becoming more virulent throughout the course of 10 backpassages in susceptible chicks. In addition, replicating virus was not detected beyond the $6^{th}$ backpassage.

Example 6

IBV Protection in Commercial Broilers Vaccinated as Day-of-Hatch with NDV C2-GA08 IBV-Ark IBV Two groups of day-of-hatch commercial broilers were delivered to the research facility. One group contained 30 chicks that were spray vaccinated in the hatchery with a combination of live C2NDV-GA08IBV-Ark IBV. This group was divided into 3 groups of 10 birds each and placed into Horsfall Bauer forced air, positive pressure (FAPP) isolation units. A second group contained non-vaccinated chicks and 10 were placed into Horsfall Bauer forced air, positive pressure (FAPP) isolation units. Birds were given food and water ad libitum throughout the trial. At 14 days-of-age, birds in groups 2-4 were challenged with either $10^{4.5}$ GA08 IBV or $10^{4.0}$ $ED_{50}$Ark IBV (see Table 1) via eye drop. Five days post-challenge (5 dpc), the birds were evaluated for clinical signs and necropsied. The treatment groups are outlined in Table 1.

TABLE 1

Group identification and treatment designations at day-of-hatch and 14 days-of-age.

| Group | Day of hatch vaccination C2-GA08-Ark | Challenge at 14 days of age | Number of birds |
|---|---|---|---|
| 1. Vaccine/no challenge | Yes | No | 10 |
| 2. Vaccine/GA08 challenge | Yes | Yes - GA08 | 10 |
| 3. Vaccine/Arkansas challenge | Yes | Yes - Ark | 10 |
| 4. No vaccine/GA08 challenge | Yes | Yes - GA08 | 10 |

On the day of necropsy (5 dpc), clinical signs were evaluated in all birds. The birds were bled for IDEXX IBV ELISA (See Table 2) and tracheal swabs were taken for IBV real time RT-PCR. Following euthanasia, cross and longitudinal trachea sections (below the point of swabbing) were collected, fixed in neutral buffered formalin, and histologically evaluated and histological scoring performed. Ten serum samples were collected from each group. Results are summarized in Table 2.

TABLE 2

IBV ELISA results from serum collected 5 days post challenge (19 days of age).

| Group | GMT | % CV | case # |
|---|---|---|---|
| 1. Vaccine/no challenge | 13 | 97 | 74019 |
| 2. Vaccine/GA08 challenge | 8 | 132.3 | 74017 |
| 3. Vaccine/Arkansas challenge | 17 | 100.2 | 74018 |
| 4. No vaccine/GA08 challenge | 9 | 125.5 | 74016 |

All groups were negative for IBV antibodies at 19 days of age as evaluated by IBV ELISA. Clinical signs observed in the vaccinated/unchallenged group were mild and limited to conjunctivitis and airsacculitis in 2/10 birds. In addition, mean tracheal lesion scores in this group were less than the other 3 treatment groups and considered normal for birds this age reared in isolation units. IBV was not detected from the tracheal scrapings in the vaccinated/unchallenged group by real time RT-PCR.

Clinical signs were observed in all birds from the unvaccinated/GA08 challenge group. This group served as the positive challenge control group. Moderate to severe airsacculitis was observed in 10/10 birds. Despite the fact that the mean tracheal lesions scores in this group (ring and longitudinal) were not significantly higher than either vaccinated/challenged group, the histological lesions were more severe. IBV was detected from the tracheal scrapings in the unvaccinated/GA08 challenge group. The quantity of viral genome was slightly less than both vaccinated/challenge groups. Clinical signs were observed in both vaccinated/GA08 challenged groups. The airsacculitis observed in 4/10 (VX/GA08 Chall) and 6/10 (VX/Ark Chall) was mild and not as severe as the UnVWGA08 Challenged group. The tracheal lesions scores for all GA08 challenged groups were numerically similar however, both vaccinated groups had less severe lesions than in the UnVX/GA08 chall group. IBV was detected equally from both vaccinated/GA08 challenged groups.

Example 7

Rapid Heat-Treatment Attenuation of Infectious Bronchitis Virus

This example describes the rapid development of an attenuated live vaccine for GA08, a new serotype of infectious bronchitis virus (IBV), using a heat-treatment method. Incubation of the GA08 strain of IBV at 56° C. and passage in embryonated eggs was used as a method to fast track the attenuation process. The virus was incubated in a 56° C. water bath and aliquots were removed every 5 minutes for up to 1 hour then each aliquot was inoculated into 10-day old embryonated eggs. Virus with the longest incubation time that produced lesions in the embryos was harvested, again incubated at 56° C. as described and passaged in embryonated eggs. Attenuation of the virus designated GA08/GA08HSp16/08 was verified in 1-day old specific pathogen free (SPF) chicks. A 10× dose of the vaccine was found to be safe for 2-week old broiler chicks of commercial origin. The efficacy of the heat-treated attenuated virus was determined by vaccinating broiler chicks of commercial origin at 1 and 14 days of age intraocularly/intranasally. Vaccinated birds that were challenged with $1\times10^{4.5}$ 50% embryo infectious doses of pathogenic GA08 virus/bird at 28 days of age were protected from the disease and challenge virus was only detected in the trachea of 1 of 21 birds by real time RT-PCR at 5 days post-challenge. The attenuation process took 10 weeks to complete, which is a substantially shorter time required to attenuate IBV by serial passage in eggs without heat-treatment (38 weeks or more).

In January 2008, a new IBV variant was first detected in a flock of 48-day old broilers in northern Georgia and has since been isolated from chickens with respiratory disease in Georgia and South Carolina. Clinical signs and lesions associated with this virus, designated GA08, are generally mild and consist of conjunctivitis, and mild tracheal rales, tracheitis and abdominal air sacculitis. Commercially available live IBV vaccines, either alone or in combination did not provide protection against GA08. This example describes a rapid heat-treatment attenuation process for the GA08 strain of IBV as well as safety and efficacy testing to examine the utility of the vaccine. Attenuation of the GA08/pass4/08 strain of IBV by heat-treatment follows a protocol similar to the method used to attenuate the JMK and H strains of IBV. But, it should be noted that infectious bronchitis virus isolates can be vastly different with respect to growth characteristics and resistance to environmental conditions and this attenuation process may not work for all IBV types.

Materials and Methods

Viruses. The GA08/pass4/08 strain of IBV (titer $1.0\times10^{5.5}$ 50% embryo infectious dose [$EID_{50}$/ml]) was used as the starting material for the heat-treatment as well as for challenge.

Heat-treatment attenuation. The GA08/pass4/08 virus was incubated at 56° C. and one milliliter (ml) aliquots were removed every 5 minutes for 60 minutes. Each aliquot was inoculated (0.1 ml/egg) into the chorioallantoic sac of at least five 10-day old embryonated chicken eggs and incubated for 6 days. The embryos were examined and allantoic fluid was harvested from the eggs inoculated with the longest heat-treatment that induced lesions in the embryos. That allantoic fluid was then used in a subsequent round of heat-treatment followed by inoculation into embryonated eggs. The procedure was repeated 8 times. Virus harvested from the last heat-treatment was passaged 4 additional times in 10-day old embryonated eggs (allantoic fluid was harvested at 48 hours post-inoculation) without heat-treatment to increase the volume and titer of the virus. Following each heat-treatment passage, the allantoic fluid used for the subsequent passage was examined for the presence of virus by real time reverse transcriptase-polymerase chain reaction (RT-PCR) as previously described (Callison et al., 2006, *J Virol Meth;* 138:60-65). The titer of 16th passage (4 initial passages plus 8 heat-treatment passages plus 4 additional passages) of the virus designated GA08/HSp16/08 was determined in 10-day old embryonated eggs and the titer was calculated by the method of Reed and Muench as described (Gelb and Jackwood, 2008, Infectious bronchitis, In: L. Dufour-Zavala, D. E. Swayne, J. R. Glisson, J. E. Pearson, W. M. Reed, M. W. Jackwood & P. Woolcock (Eds.); A laboratory manual for the isolation, identification, and characterization of avian pathogens, 5th ed. (pp. 146-149). Kennett Square, Pa., American Association of Avian Pathologists; and Villegas, 2008, Titration of biological suspensions, In: Dufour-Zavala, L., Swayne, D. E., Glisson, J. R., Jackwood, M. W., Pearson, J. E., Reed, W. M. & Woolcock, P. R. (Eds.); A laboratory manual for the isolation and identification of avian pathogens, 5th ed. (pp. 217-221); Jacksonville, Fla., American Association of Avian Pathologists).

Purity and virus identity tests were conducted as described in section 113.300 of Title 9 of the Code of Federal Regulations (1999). Passage 16 of the GA08/HSp16/08 virus was tested for purity from bacteria, fungi, mycoplasma, and extraneous viruses including chicken anemia virus, hemagglutinating viruses and avian leukosis virus (Dufour-Zavala et al., 2008, A laboratory manual for the isolation and identification of avian pathogens. American Association of Avian Pathologists, Jacksonville, Fla.). The virus was also tested for attenuation in one-day-old SPF leghorn chicks (Charles River SPAFAS, N. Franklin, Conn.) according to the procedures in section 113.327 of Title 9 code of Federal Regulations (1999). Chicks were randomly divided into two groups of 10 birds each and housed in positive-pressure Horsfal isolation units. Feed and water were given ad libitum and the birds were examined twice daily. Birds in the first group were given $1 \times 10^4$ EID$_{50}$/bird of pass 16 of the GA08/HSp16/08 virus by eyedrop and intranasally. This dose was selected because in our experience, it is an amount of virus likely to infect and produce disease.

The safety of the virus was evaluated in a separate experiment using a 10× dose, as described below for see Safety testing. The second group of birds, which served as a positive control, was given $1\times10^4$ $EID_{50}$/bird of pass 16 of the virus without heat-treatment. The third group of birds were not exposed and served as a negative control. Five birds in each group were euthanized and necropsied at 5 and at ten days post-exposure. Tracheal swabs were placed in 1 ml of ice cold phosphate-buffered saline (PBS, pH 7.4) and stored at −80° C. until tested for the presence of viral RNA by real time RT-PCR. The lower portion of the trachea (below the swabbed area) was fixed in 10% neutral buffered formalin, routinely processed, and embedded into paraffin blocks. Thin sections were cut and stained with hematoxylin and eosin and examined by light microscopy. Epithelial hyperplasia, lymphocyte infiltration and the severity of epithelial deciliation were scored for each trachea from 1 to 4 with 1=normal, 2=focal, 3=multifocal, and 4=diffuse. The least significant difference of the means was statistically calculated with the Student t-test for each pair using JMP Statistical Discovery Software (SAS Institute, Inc., Cary, N.C.) as previously described (Jackwood et al., 2003, *Avian Dis;* 47:627-632).

Safety testing. Twenty-five commercial broiler chicks (Fieldale Farms, Baldwin, Ga.) were housed in positive-pressure Horsfal isolation units, given feed and water ad libitum and used to test the safety of the GA08/HSp16/08 virus (pass 16) according to section 113.327, d, 2, of Title 9 Code of Federal Regulations (1999). A 10× dose ($1\times10^5$ $EID_{50}$) of virus was given by eyedrop to the chicks at 5 days of age and the birds were examined for clinical signs twice daily for 21 days. Five additional birds were maintained as negative controls. Prior to exposure, sera were collected from 7 birds and stored at −20° C. until tested for maternal antibodies by commercial ELISA (IDEXX, Westbrook, Me.). In this ELISA test, titers of greater than 256 are considered positive. At the end of the experiment, sera were collected and stored at −20° C. until tested by ELISA (IDEXX) and the birds were euthanized and tracheas were collected and processed for histopathology as described above.

Efficacy testing. Thirty-three one-day old commercial broilers (Fieldale Farms) were randomly divided into 3 groups. Twenty-one birds in the first group were vaccinated intraocularly and intranasally ($1\times10^4$ $EID_{50}$/bird) with the GA08/HSp16/08 virus at 1 and 14 days of age. Six birds each in the second and third group were not vaccinated. The first and second groups of birds were challenged intranasally ($1\times10^{4.5}$ $EID_{50}$/bird) with pathogenic GA08/pass4/08 at 35 days of age. At 5 days post-challenge, all of the birds were euthanized and necropsied. At necropsy, tracheal swabs and sera were collected and stored as described above. Efficacy was based on not less than 90% of the controls positive for virus recovery and not less than 90% of the vaccinates negative for virus recovery. The lower halves of tracheas were collected and processed for histopathology as described above. Scoring and statistical analysis were also as described above.

RNA extraction and real time RT-PCR. Viral RNA was extracted from 50 ul of the PBS from the tracheal swab using the MagMAX-96 RNA Isolation Kit (Ambion Inc., Austin Tex.) according to the manufacturer's protocol on a KingFisher magnetic particle processor (Thermo Scientific, Waltham, Mass.). Real time RT-PCR was conducted using a Smart Cycler II (Cepheid, Sunnyvale, Calif.) and the AgPath-IDtm One-Step RT-PCR kit (Ambion Inc.) according to the manufacturer's recommendations. Primers and probe for the real time RT-PCR were previously published (Callison et al., 2006, *J Virol Meth;* 138:60-65) and consist of a forward primer IBV5'GU391 (5'-GCTTTTGAGCCTAGCGTT-3') (SEQ ID NO:15), a reverse primer IBV5'GL533 (5'-GCCATGTTGTCACTGTCTATTG-3') (SEQ ID NO:16) and a Taqman dual-labled probe IBV5'G probe (5'-FAM-CACCACCAG AACCTGTCACCTC-BHQ1-3') (SEQ ID NO:17). The primers were obtained from Integrated DNA Technologies (Coralville, Iowa) and Taqman probe was synthesized by BioSearch Technologies (Novato, Calif.). Real time RT-PCR components and thermocycler parameters were conducted as previously described, and a standard curve for the assay, which was previously published was used to calculate the approximate genome copy number for each sample (Callison et al., 2006, *J Virol Meth;* 138:60-65). Any sample below the calculated level of detection (100 genome copies) was considered negative.

Negative control swab samples, which were swabs placed in buffer during necropsy, were included in the RNA extraction and real time RT-PCR assay. In addition, known negative and positive samples for RNA isolation and for real-time RT-PCR were included at every 10th sample analyzed. Negative controls also included allantoic fluid collected from non-inoculated SPF eggs, and the isolated material was carried forward to the real time RT-PCR assay as well as real-time RT-PCR assay reaction mixture without RNA template. Positive controls consisting of allantoic fluid containing Mass41 type IBV whole virus ($1\times10^{4.0}$ $EID_{50}$/ml) was included for the RNA extraction and carried forward to the real time RT-PCR assay, as well as known positive (from previous real time RT-PCR positive samples) IBV RNA from the Mass41 strain of IBV, which was used as template in the real time RT-PCR assay. If any of the controls were not as expected, the experimental samples and controls were retested.

Molecular characterization. Viral RNA was extracted from 50 ul of allantoic fluid containing virus using the MagMAX-96 RNA Isolation Kit (Ambion Inc.) according to the manufacturer's protocol on a KingFisher magnetic particle processor (Thermo Scientific). The S1 glycoprotein gene was RT-PCR amplified from the extracted RNA following previously published methods and the amplified product was sequenced. The amplified products were purified using GenElute™ spin columns (Supelco, Bellefonte, Pa.) and concentrated using Microcon 30 columns (Amicon, Beverly, Mass.). The 3' primer designated Degenerate 3' (5'-CCATAAGTAACATAAGGRCRA-3') (SEQ ID NO:18) and a 5' primer designated NEWS1OLIGO5' (5'TGAAACTGAACAAAAGAC3') (SEQ ID NO:19) were previously published (Lee et al., 2000). Sequencing was conducted with the Prism™ DyeDeoxy terminator cycle sequencing kit according to the manufacturer's recommendations (Perkin Elmer, Foster City, Calif.).

Sequences were compared by nucleotide-nucleotide BLASTn and protein-protein BLASTp search analyses on-line at the National Center of Biotechnology Information (ncbi.nlm.nih.gov/BLAST/ on the worldwide web). Sequences identified by BLAST analysis as well as previously published IBV vaccine sequences (McKinley et al., 2008, *Vaccine;* 26:1274-1284) were used for ClustalW alignment (MegAlign software version 1.03, DNASTAR, Inc., Madison, Wis.) and phylogenetic trees were constructed with the Neighbor-Joining method, Maximum Parsimony method, and UPGMA with 1000 bootstrap replicates (MEGA4, megasoftware.net/index.html on the worldwide web) (Tamura et al., 2007, *Mol Biol Evol;* 24:1596-1599).

Results

Attenuation. Data on the heat-treatment attenuation of GA08/pass4/08 are presented in Table 3. The time of heat-treatment at 56° C. ranged from 10 minutes to 55 minutes and did not appear to show a relationship with passage number or virus titer as determined by real time RT-PCR. Passage 13 of the virus in embryonated eggs was conducted without prior heat-treatment and the titer of the virus as determined in embryonated eggs was $1\times10^{4.45}$ $EID_{50}$/ml. To increase the titer, the virus was passaged 4 more times (virus containing allantoic fluid was harvested at 48 hours post-inoculation) in embryonated eggs without prior heat-treatment and the titer of the 16th embryo passage designated GA08/HSp16/08 was determined to be $1\times10^{6.63}$ $EID_{50}$/ml. The 16th embryo passage of GA08/HSp16/08 was negative for bacteria, fungi, mycoplasma, chicken anemia virus, hemagglutinating viruses and avian leukosis virus and was used in subsequent safety and efficacy experiments.

No clinical signs were observed in one-day old SPF leghorn chicks given $1\times10^4$ $EID_{50}$/bird by eyedrop and intranasally at either 5 or 10 days post-inoculation (Table 4). In addition, the average tracheal lesion scores (1.0) from birds on both necropsy days were identical to the negative control birds (Table 4). In contrast, all of the birds given pass 16 of the virus without heat-treatment had clinical signs, challenge virus was detected in all the birds and tracheal lesions (average score 2.95) indicated all of the birds had acute tracheitis.

TABLE 3

Heat treatment[a] of attenuation of IBV GA08/pass4.08.

| Passage number following heat treatment | Heat-treatment time (min)[b] | Ct value (calculated virus titre)[c] |
|---|---|---|
| 5[d] | 35 | 20.87 ($10^{5.9}$) |
| 6 | 55 | 16.48 ($10^{7.2}$) |
| 7 | 10 | 24.57 ($10^{4.9}$) |
| 8 | 15 | 16.20 ($10^{7.3}$) |
| 9 | 40 | 15.71 ($10^{7.4}$) |
| 10 | 30 | 16.64 ($10^{7.2}$) |
| 11 | 15 | 24.83 ($10^{4.8}$) |
| 12 | 20 | 22.33 ($10^{5.6}$) |

[a]Virus was incubated at 56 C. and 1 ml aliquots were removed every 5 min for 60 min and inoculated (0.1 ml) into the chorioallantoic sac of 10-day-old embryonating eggs.
[b]Allantoic fluid from the longest heat-treatment (56 C.) time that caused lesions in embryos at 6 days post inoculation was harvested and used for subsequent passages.
[c]Ct = real-time RT-PCT cycle threshold value (calculated virus titre based on the standard curve formula Y = −0.282X + 11.861).
[d]Passages 1 to 4 in embryonating eggs were conducted prior to heat treatment.

TABLE 4

Attenuation testing of IBV GA08/HSp16/08 in 1-day-old SPF chicks.

| | Virus isolation | | Tracheal lesion scores | |
|---|---|---|---|---|
| Treatment[a] | Day 5[b] | Day 10 | Day 5 | Day 10 |
| GA08/HSp16/08 | | | | |
| Heat-treated pass 16 virus GA08/08/08 | 0/5[c] | 0/5 | 1.0 | 1.0 |
| Pass 16 (no heat treatment) | 5/5 | 5/5 | 2.8 | 3.1 |
| Negative controls | 0/5 | 0/5 | 1.0 | 1.0 |

[a]Birds given virus were given $10^4$ $EID_{50}$ by eye drop and intranasally.
[b]Days post exposure.
[c]Number positive/number examined.

Safety testing. Twenty-five commercial broiler chicks were given $1\times10^5$ $EID_{50}$/bird (10× dose) of the GA08/HSp16/08 virus at 5-days of age and no clinical signs were observed for 21 days when the birds were euthanized and necropsied. In addition, no clinical signs were observed in five additional birds maintained as negative controls at the same time. Maternal antibody titers were detected in sera collected prior to treatment (at 5-days of age) with 6 of 7 birds positive and a geometric mean ELISA titer of 588. No antibody titers were observed in the control birds at necropsy. Sera collected from the treated birds 21 days after exposure and tested by ELISA resulted in 5 of 25 birds positive with a geometric mean titer standard deviation of 866.9±831.9 for the positive birds only. Tracheas collected 21 days after infection and processed for histopathology showed no microscopic lesions (score=1.0) in the treated birds as well as the negative controls.

Efficacy testing. The efficacy testing data are presented in Table 5. None of the broilers vaccinated intraocularly and intranasally at 1 and 14 days of age with $1\times10^4$ $EID_{50}$/bird of the GA08/HSp16/08 virus and challenged with GA08/pass4/08 at 35 days of age had clinical signs of disease at 5 days post-challenge (Table 5). Six birds not vaccinated and challenged intranasally ($1\times10^{4.5}$ $EID_{50}$/bird) with GA08/pass4/08 at 35 days of age had clinical signs consisting of watery eyes, nasal mucus, and tracheal rales, at 5 days post-challenge. No clinical signs were observed in negative control birds 5 days post-challenge. Challenge virus was detected in tracheal swabs by real time RT-PCR in one bird in the vaccinated and challenged group at necropsy. Whereas virus was detected in all 6 birds in the non-vaccinated and challenged group at necropsy indicating our time point of 5-days post-challenge for virus detection was suitable. The tracheal lesion scores for the vaccinated and challenged birds were statistically higher than the negative controls but not as high as the non-vaccinated challenged group (p<0.05) indicating that some virus replication occurred in the challenged birds.

TABLE 5

Efficacy testing fo the GA08/HSp16/08 virus in commercial broiler chickens at day 5 following challenge at 35 days of age with GA08/pass4/08.

| Treatment | Clinical signs[a] (% protection) | Virus isolation[b] (% protection) | Histopathology[c] | ELISA antibody titre (number positive/total)[d] |
|---|---|---|---|---|
| Vaccinated[e] and challenged[f] | 0/21 (100%) | 1/21 (92.2%), $C_t$ = 35.4 g | 2.3[B] | 590 ± 620 (17/21) |
| Challenged[f] | 6/6 (0%) | 6/6 (0%) | 3.2[C] | 15 ± 21 (0/6) |
| Negative controls | 0/6 | 0/6 | 1.0[A] | 57 ± 90 (0/6) |

[a]Clinical signs were based on ocular and nasal discharge and tracheal rales.
[b]Individual tracheal swab samples tested by real-time RT-PCR.
[c]Average tracheal lesion scores. Numbers with different uppercase superscript letters are statistically different (P < 0.05).
[d]Geometric mean serum antibody titre ± standard deviation. Titres > 256 are considered positive.
[e]Birds were vaccinated intraocularly and intranasally with 1 × 10$^4$ EID$_{50}$/bird IBV GA08/HSp16/08 at 1 and 14 days of age.
[f]Birds were challenged intranasally with 1 × 10$^{4.5}$ EID$_{50}$/bird of pathgenic IBV GA08/pass4/08 at 35 days of age.
[g]$C_t$ = real-time RT-PCR cycle threshold value (calculated virus titre based on the standard curve formula Y = –0.282X + 11.861).

No ELISA serum antibody titers (Table 5) were detected for the negative control birds or for the challenge control birds. Seventeen of 21 vaccinated and challenged birds were positive for IBV antibodies with a geometric mean antibody ELISA titer of 590. The antibody ELISA titers ranged from 462 to 2,691.

Figures 2, 2A, 2B, 2C:
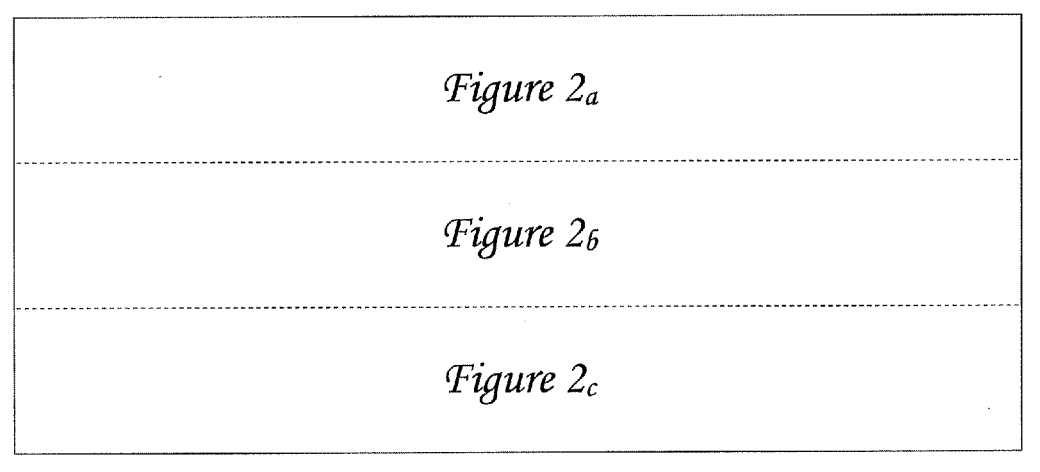

Molecular Characterization. The S1 subunit of the spike gene for the GA08/pass4/08 challenge strain, the GA08/08/08 pass 16 non-heat treated strain and the GA08/HSp16/08 the heat-treated strain were sequenced The nucleotide (SEQ ID NO:7) and amino acid sequences (SEQ ID NO:8) of the S1 glycoprotein of the GA08/HSp16/08 the heat-treated strain are shown in FIG. 2.

The sequences for the S1 subunit of the spike gene for the GA08/pass4/08 challenge strain, the GA08/08/08 pass 16 non-heat treated strain and the GA08/HSp16/08 the heat-treated strain were submitted to GenBank (accession nos. GU361606, GU734804 and GU360617 respectively).

ClustalW was used to align the S1 protein sequences and phylogenetic analysis computed using Neighbor-Joining and the Nei-Gojobori method for the GA08 isolate from the index case GA08/GU301925/08 (GenBank accession no. GU301925), GA08/pass4/08, GA08/08/08 strain passage 16 and GA08/HSp16/08 showed the sequences to be from 91.5% to 96.9% similar. The phylogenetic reconstruction with other representative IBV strains is presented in FIG. 3. The GA08 viruses cluster in a distinct group. They border the group containing HN99, JAAS/04, and N1/62 with 80.4% to 85.6% similarity (Table 6). They are also adjacent to the group of California IBV isolates CA/557/03, CA/CA12495/98, CA/12495/98, and CAV/CAV9437/95 with 78.7% to 83.5% sequence similarities as well as Ark/ArkDPI/81 with 77.8% to 82.5% similarity (Table 6).

TABLE 6

Sequence distances (percentage identity) of S1 protein alignment (ClustalW).

| | GA08/ GU301925/08 | GA08/ pass4/08 | GA08/ HSp16/08 | GA08/ 08/08 pass 16[a] |
|---|---|---|---|---|
| GA08/GU301925/08[b] | — | | | |
| GA08/pass4/08 | 96.9 | — | | |
| GA08/HSp16/08 | 94.5 | 92.8 | — | |
| GA08/08/08 pass 16 | 96.2 | 93.9 | 91.5 | — |
| HN99 | 85.3 | 82.5 | 80.4 | 81.8 |
| JAAS/04 | 85.6 | 82.8 | 80.8 | 82.5 |
| N1/62 | 85.6 | 82.8 | 80.8 | 82.5 |
| Ark/ArkDPI/81 | 82.5 | 80.0 | 77.8 | 79.7 |

TABLE 6-continued

Sequence distances (percentage identity) of S1 protein alignment (ClustalW).

| | GA08/ GU301925/08 | GA08/ pass4/08 | GA08/ HSp16/08 | GA08/ 08/08 pass 16[a] |
|---|---|---|---|---|
| CA/557/03 | 82.9 | 80.4 | 78.2 | 79.0 |
| CAV/CAV1686/95 | 83.1 | 80.3 | 78.8 | 79.5 |
| CA/CA12495-98 | 83.5 | 80.7 | 79.2 | 79.7 |
| CAV/CAV9437/95 | 83.0 | 80.1 | 78.7 | 79.3 |

[a]Virus passaged 16 times in embyonated eggs without heat treatment.
[b]Virus isolate from the index GA08 case in broilers submitted to GenBank (accession number GU301925).

Discussion

In this example, a heat-treatment method that was used to shorten the time required to attenuate the GA08 strain of IBV. The GA08 heat-treated virus was tested for attenuation, safety and efficacy. Attenuation of GA08/pass4/08 in one-day old chicks was accomplished by exposure of the virus to 56° C. followed by propagation in embryonated eggs 8 times (pass 5 to pass 12). Because the titer of the virus was low (1×10$^{4.45}$/ml) it was passaged in embryonated eggs 4 more times (to pass 16) to increase the titer for use in safety and efficacy studies. Infectious bronchitis virus is heat-labile; being inactivated at 56° C. for 15 minutes (Cavanagh and Gelb, 2008, Infectious bronchitis, in: Saif, Y. M., H. J. Barns, A. M. Fadley, J. R. Glisson, L. R. McDougald, D. E. Swayne (Eds.), Diseases of poultry, 12th ed. pp. 117-135). Ames, Iowa, Blackwell Publishing, Ames, Iowa). From one passage to the next, the longest 56° C. incubation time that did not completely inactivate the virus varied from 15 minutes to 55 minutes. The incubation times did not appear to correlate with virus titer. Studies on severe acute respiratory syndrome coronavirus (SARS-CoV) showed that incubating the virus at 56° C. for 60 minutes or longer reduced the titer to undetectable levels (Kariwa et al., 2006, Dermatology; 212 Supplement 1:119-123). However, coronavirus inactivation is apparently dependent on the amount of protein in the sample. Addition of protein to 20% of a sample containing the SARS-CoV resulted in infectious virus following heat-treatment at 56° C. for 60 minutes (Rabenau et al., 2005, Med Microbiol Immunol; 194:1-6). The protein content of egg albumen is approximately 10% (Stadelman and Cotterill, 1977, Egg science and technology, 2nd ed. AVI Publishing Company, Inc., Westport, Conn.), which may account for the presence of live IBV following incubations at 56° C. for over 15 minutes (see Table 3).

Based on these data, it would appear that IBV subpopulations resistant to heat-inactivation are less virulent for chickens. The mechanism of action of heat-treatment attenuation is unknown but heat-inactivation of coronaviruses is thought to be through disruption of the virus structure. Stability studies on the SARS-CoV nucleocapsid protein, the alpha-helical viral protein that interacts with the viral genomic RNA to form the viral nucleocapsid, was reported to begin unfolding at 35° C. and was completely denatured at 55° C. in phosphate buffered saline (Wang et al., 2004, *Biochem;* 43:11103-11108). Since nucleocapsid protein has an RNA-binding domain and is closely associated with the viral genomic RNA it is possible that disruption of the nucleocapsid protein could leave the viral RNA open to mutagenesis leading to attenuation.

Safety of the GA08/HSp16/08 was demonstrated by giving a 10× dose to 5-day old broiler chicks. Broiler chicks were used so that the characteristics of the vaccine in commercial birds with maternal antibodies could be studied. A previous study showed that a high percentage of chicks failed to produce IBV serum antibodies following a single intraocular vaccination at 1 day of age regardless of maternal antibody status (Mondal and Naqi, 2001, *Vet Immunol Immunopathol;* 79:31-40). This example is consistent with that report since only 5 of 25 birds given a single dose of GA08/HSp16/08 produced detectable serum antibodies. It is well known that IgM can be detected soon after an initial IBV infection, and that it wanes quickly. That plus the fact that the ELISA test primarily detects IgG specific serum antibodies against IBV could explain the low percentage of antibody positive chicks following a single vaccination. The efficacy experiment showed that two doses of the GA08/HSp16/08 induced a protective immune response in maternal antibody positive birds, which is consistent with previously reported data (Mondal and Naqi, 2001, *Vet Immunol Immunopathol;* 79:31-40).

Sequence analysis and comparison of the parent virus GA08/pass4/08 with the attenuated virus GA08/HSp16/08 showed 41 residue changes (all within the first 282 amino acids) of the 543 residue S1 subunit of the spike gene, which calculates to 92.8% identity indicating that heat-treatment and passage in embryonated eggs did result in genetic changes. However, the pathogenic GA08/08/08 strain passed 16 times in eggs without heat-treatment showed 36 amino acid changes in the S1 subunit when compared with the parent GA08/pass4/08 virus, which calculates to 93.9% identity. It is not possible from these data to determine if the genetic changes were a result of mutations that occurred during virus replication or if the observed changes were due to selection of existing virus subpopulations in the original inoculum or both. The S1 gene is the most variable gene within IBV and plays a role in host cell attachment, virus entry, and stimulation of neutralizing and serotype specific antibodies. However, it was recently shown that pathogenicity (attenuation) related genes are located in the replicase genes (1a/1ab) (Armesto et al., 2009, *PLoS One;* 4(10):e7384). Therefore it is likely that mutations leading to the attenuation of GA08/HSp16/08 are located in the 1a/1ab genes. It logically follows that for an attenuated strain of IBV to induce a neutralizing antibody response, the S1 gene of the attenuated virus ought to be relatively similar to the pathogenic virus. To evaluate the relative similarity of the GA08 viruses we compared them to each other and to viruses of different serotypes (FIG. 3) and found the GA08 viruses including the attenuated heat-treated virus clustered into a distinct group. These data indicated the GA08/HSp16/08 virus ought to induce neutralizing antibodies against the GA08 virus type, which was verified by the efficacy studies in chickens.

Viruses in an adjacent Glade with 80% to 85% similarity were HN99 a nephropathogenic strain and JAAS/04 a vaccine strain from China, and N1/62 a subgroup I nephropathogenic strain from Australia (Liu et al., 2006, *Avian Pathol;* 35:394-399; and Sapats et al., 1996, *J Gen Virol;* 77:413-418). The GA08 virus group also neighbored the California viruses CA/557/03, CAV/CAV1686/95, CA/CA12495/98, and CAV/CAV9437/95 (78% to 83% similarity) as well as Ark/ArkDPI/81 (77% to 82% similarity) indicating that the spike glycoproteins of these viruses may be related. Although exceptions do occur, typically genetically distant viruses (<89% similarity in S1) that fall into different genetic groups do not cross protect (Jackwood et al., 2007, *Avian Dis;* 51:527-533; and Lee et al., 2001, *Avian Dis;* 45:164-172).

It should be acknowledged that although the safety and efficacy testing of the GA08/HSp16/08 virus (pass 16) was performed according to section 113.327, d, 2, of Title 9 Code of Federal Regulations (1999) for IBV vaccine testing, a rather limited number of birds were used and the dose for safety testing was relatively low. In addition, broilers of commercial origin with potentially undetected maternal immunity to the GA08 virus could have altered the results.

In summary, the IBV GA08 type virus, a new variant virus identified in Georgia in 2008, was attenuated by heat-treatment in approximately 10 weeks. This represents an extremely short time compared to 38 to 50 weeks for conventional passage in embryonated eggs. The pathogenic parent virus and attenuated virus had 92.8% amino acid similarity in the 51 glycoprotein and were not genetically similar to other viruses found in the USA. Based on clinical signs, lesions, and challenge virus reisolation, the attenuated GA08/HSp16/08 virus protected broiler chickens against challenge with the pathogenic GA08 virus. This example has also published as Jackwood et al. (*Avian Pathol.* 2010 June; 39(3):227-33).

Example 8

Pathogenesis of GA07, a Recent Field Isolate of Nephrotropic Infectious Bronchitis Virus Infectious Bronchitis Virus (IBV) was isolated from the kidneys of several commercial broiler flocks in northeast Georgia that were exhibiting excessive flushing. Around midsummer, the clinical presentation began to change and isolations of IBV from both trachea and kidney were obtained from multiple broiler flocks. Clinical signs ranging from excessive flushing, respiratory disease, or a combination of the two, were seen within these flocks. In many of the infected flocks, excessive mortality often accompanied the clinical signs. Most of the mortality appeared to be from secondary issues, such as *E. coli* infections, following the original viral infection. Often along with the elevated mortality came high condemnations at the plant for airsacculitis. The airsacculitis ranges from a mild "sudsy" airsacculitis to a more chronic appearing caseous airsacculitis. This example examines the pathogenesis of the earlier viruses that appeared to be more nephrotropic in nature.

Throughout the world there have been a number of reported nephropathogenic IBV (NIBV) field isolates. A few of the more recent outbreaks have been reported from Australia, China, India, Europe, and the United States (Bayry et al., 2005, *J Clin Microbiol;* 43:916-918; Bing et al., 2007, *Virus Genes;* 35:333-337; Ignjatovic et al., 2001, *J Comp Pathol;* 126:115-123; Liu and Kong. 2004, *Avian Pathol;*

33:321-327; Meulemans et al., 1987, *Vet Rec;* 120:205-206; and Ziegler et al., 2002, *Avian Dis;* 46:847-858). Several of these isolates resulted in both respiratory and renal clinical signs in infected birds. A recent IBV isolate in Egypt exhibited moderate to severe respiratory and renal signs with up to 20% mortality in broilers (Abdel-Moneim et al., 2006, *Virol J;* 3:78). Among 25 strains of IBV isolated within Australia from 1961 to 1994, twelve strains were nephropathogenic with mortality ranging from 5-90%, ten resulted only in respiratory disease with no mortality, and three exhibited gross lesions in both the respiratory and renal systems with no mortality (Ignjatovic et al., 2001, *J Comp Pathol;* 126:115-123). Within the United States, several outbreaks of NIBV were reported in the late 1990's and early 2000's in both layers and broilers with up to 23% mortality in the broilers (Ziegler et al., 2002, *Avian Dis;* 46:847-858).

Within current Georgia isolates, IBV ELISA results from many cases exhibited positive geometric mean titers (GMT), but serotype specific HI results were inconclusive. Cross virus neutralization studies using several of these recent isolates in combination with the common current US vaccines strains showed little to no cross-reaction. Along with the use of these serologic based tests, PCR and partial sequencing of the S1 gene was performed to better classify and serotype these viruses. The use of PCR and sequencing to group and type IBV isolates has become more prevalent in recent years. It has been demonstrated that the sequence from the hypervariable region of the IBV S1 gene often correlates well with virus neutralization tests and can be reliably used to serotype an IBV isolate (Lee et al., 2003, *J Vet Diagn Invest;* 15:344-348). Many recent nephropathogenic isolates from several countries have been serotyped and classified as variants based on partial sequencing of the S1 gene (Bayry et al., 2005, *J Clin Microbiol;* 43:916-918; Bing et al., 2007, *Virus Genes;* 35:333-337; Ladman 2006, *Avian Pathol;* 35:127-133; and Liu and Kong. 2004, *Avian Pathol;* 33:321-327). Ladman et al., compared several nephropathogenic field isolates of IBV to a reference strain and showed that protective relatedness values were more strongly correlated with partial S1 sequence identity values than they were to antigenic relatedness values derived from virus neutralization tests and cross-challenge studies (Ladman 2006, *Avian Pathol;* 35:127-133). The nucleotide sequence of the S1 gene from early Georgia isolates was approximately 85% similar to previously published sequences of nephropathogenic strains of IBV. Since the original isolation of GA07, additional IBV sequences have been made available in GenBank that are more related to this virus than previously identified. Specifically, the GA07 S1 nucleotide sequence is 95% similar to a California isolate. This lack of sequence similarity and serologic response may indicate that the currently used IBV vaccine strains will not protect chickens from infection with these newer variant isolates.

With this example, the pathogenesis of one of the earlier viruses isolated from a field case involving excessive flushing was evaluated by experimental challenge in SPF and broiler chickens. Along with the challenge group, a Mass-41 positive control group and a non-challenged negative control group were included. Clinical signs, gross lesions, histopathology, virus isolation, and serology were evaluated for all groups.

Materials and Methods

Challenge Virus. An Infectious Bronchitis Virus (GA-07) was isolated from the kidneys of commercial broilers submitted from the field for excessive flushing. This virus was isolated in 9-11 day old chicken embryos, propagated, and titrated to $10^{4.5}$ EID50/ml for challenge studies.

Positive Control Virus. A Mass-41 IBV challenge virus was used as the positive control. This virus was titrated to $10^{4.5}$ EID50/ml.

SPF layer-type Chickens. 75 1 day-old SPF layer-type chickens were obtained from Merial Select. These birds were divided into 3 groups with 25 birds per group. Group 1 consisted of non-challenged negative controls (SPF-1), Group 2 consisted of Nephropathogenic IBV challenged birds (SPF-2), and Group 3 consisted of the positive control Mass-41 challenged birds (SPF-3). Each group was divided in half with 12 chicks being placed in one Horsfall-type isolator unit and 13 chicks being placed in another for a total of 6 isolators. The chicks were provided feed and water ad libitum. This is shown in Table 7.

Broiler Chickens. 75 1 day-old broiler chickens were obtained from the University of Georgia's Poultry Science Department. The parents of these chicks had a minimal vaccination history. These birds were divided into 3 groups with 25 birds per group. Group 1 consisted of non-challenged negative controls (BRO-1), Group 2 consisted of Nephropathogenic IBV challenged birds (BRO-2), and Group 3 consisted of the positive control Mass-41 challenged birds (BRO-3). Each group was placed into floor pens within individual isolated colony houses. The birds were provided feed and water ad libitum. This is shown in Table 7

Challenge. Two weeks post-placement Group 2 and Group 3 of both the SPF layer-type chickens and the broiler chickens were challenged with their respective treatments, NIBV and Mass-41. 0.05 ml of $10^{4.5}$ EID50/ml of the NIBV challenge was inoculated into the conjunctiva of each eye for a total of a 0.1 ml inoculation. The same was done for the Mass-41 ($10^{4.5}$ EID50/ml) challenged groups. Immediately prior to challenge, blood was taken from all birds to determine baseline IBV titers using a commercial ELISA kit (Idexx). All birds were observed daily over the next 4 weeks. Any clinical signs or other observations were noted. The birds continued to receive feed and water ad libitum. This is shown in Table 7.

Tissue Collection. Starting 4 days post-challenge, 2 birds from each treatment groups of broilers and SPF chickens were euthanized and trachea, kidney, and a portion of the mid-intestinal tract were collected. One portion of each piece of tissue was fixed in 10% buffered formalin for microscopic examination. The other portion was used for virus isolation and PCR. Sample collection continued every 4 days for 4 weeks post-challenge. Gross lesions were observed and noted during necropsy at each time period.

Histopathology. After fixation, the tissue samples were routinely processed, embedded in paraffin, and cut into 5-μm sections for hematoxylin and eosin staining. For the tracheas, epithelial hyperplasia, lymphocytic infiltration, and the severity of epithelial deciliation were scored for each trachea from 1 to 4 with 1=normal, 2=focal to multifocal lesions, 3=necrosis present, and 4=ulcerations present. A numerical score was not assigned to lesions within the mid-intestine or the kidney. Any microscopic lesions present in these tissues were noted and described on an individual section basis.

Serology. Blood was collected from all birds remaining in each group at two weeks (pre-challenge), 4 weeks (2 weeks post-challenge), 5 weeks, and 6 weeks of age. The serum from this blood was used to evaluate IBV titers by both a commercial ELISA kit (Idexx) and through IBV hemagglutination inhibition (HI) tests. HI tests were conducted using Massachusetts, Connecticut, Arkansas 99, and Delaware 072 IBV antigen. A subset of ten birds was randomly selected and wing-banded at two weeks of age. These birds were maintained throughout the study and bled at 2, 4, 5, and 6 weeks of age. Serum from these birds was used to evaluate serum uric acid levels.

Virus Isolation. Tracheas from clinical samples were homogenized in a virus transport medium containing antibiotics and sterile filtered through a 0.45 micron filter. The homogenized/filtered material was inoculated via the chorioallantoic sac of nine day old embryos (0.1 ml/embryo) into each of 3 embryos and incubated at 37 C with 5% CO2. At 72 hours post inoculation, 0.4 ml allantoic fluid was aseptically removed from each of the 3 embryos and pooled. An aliquot of pooled allantoic fluid was treated with neuraminidase as previously described and tested for hemagglutination of 5% chicken red blood cells. The allantoic fluid from the first embryo passage was used to inoculate a second set of 9-day-old embryos. This was repeated for a total of 4 embryo passages. Inoculated embryos were opened on the 7th day post inoculation and examined for lesions characteristic of IBV including mortality, clubbed down, stunting, curled toes and kidney urates. On the fourth embryo passage, embryos displayed kidney urates. Allantoic fluid from this passage was used for PCR.

TABLE 7

Experimental Design.

| Group (n = 25) | Bird Type | Challenge | Age at Challenge |
|---|---|---|---|
| SPR-1 | SPF Leghorn | None | 2 wks |
| SPF-2 | SPF Leghorn | GA-07 | 2 wks |
| SPF-3 | SPF Leghorn | Mass-41 | 2 wks |
| BRO-1 | Broiler | None | 2 wks |
| BRO-2 | Broiler | GA-07 | 2 wks |
| BRO-3 | Broiler | Mass-41 | 2 wks |

Results

Broiler Clinical Signs and Necropsy Findings. Beginning two days post-challenge (P-C) and continuing through 5 days P-C a mild snick was noted in the GA-07 challenge group (BRO-2) and a moderate snick was noted in the Mass-41 challenge group (BRO-3). Along with the snick a mild conjunctivitis was noted in all of the birds in BRO-2 and BRO-3 throughout much of the experiment. Mortality in all three groups was very low throughout the entire experiment with one bird dying in BRO-1 and BRO-3 and 2 birds dying in BRO-2. A necropsy was performed on all mortality and no deaths were attributed to IBV infection or subsequent secondary infections. Clinical signs and necropsy findings for the broilers is shown in Table 8.

TABLE 8

Clinical signs and necropsy findings for the broilers.

| Week | Group | Conjunctivitis | Tracheitis | Airsacculitis |
|---|---|---|---|---|
| 2.5 | BRO-1 | | | |
| | BRO-2 | 2/2 | 1/2 | |
| | BRO-3 | 2/2 | 2/2 | |
| 3.2 | BRO-1 | | | |
| | BRO-2 | 1/2 | | 1/2 |
| | BRO-3 | 2/2 | 1/2 | 1/2 |
| 3.6 | BRO-1 | | | |
| | BRO-2 | 2/2 | | |
| | BRO-3 | 1/2 | | 2/2 |
| 4.3 | BRO-1 | | | |
| | BRO-2 | | | |
| | BRO-3 | 2/2 | | 2/2 |
| 4.7 | BRO-1 | | | |
| | BRO-2 | | | 2/2 |
| | BRO-3 | | | 2/2 |
| 5.4 | BRO-1 | | | |
| | BRO-2 | | | 1/2 |
| | BRO-3 | | | |
| 6.1 | BRO-1 | | | |
| | BRO-2 | | | 5/19 |
| | BRO-3 | | | 1/19 |

The most consistent finding throughout the necropsies was an airsacculitis that first appeared 8 days P-C. The airsacculitis was present in the Mass-41 challenge group and to a slightly lesser extent in the GA-07 group. It was usually mild and ranged from a "sudsy" type airsacculitis in the majority of the birds to a mild caseous airsacculitis in two of the Mass-41 challenged birds. During the 4 day P-C necropsy, a mild tracheitis was noted in the majority of the IBV challenged birds. No macroscopic kidney lesions were observed in any of the birds regardless of challenge.

Broiler Serology. Blood was collected from all birds remaining in each group immediately prior to challenge, 2 weeks P-C, 3 weeks P-C, and 4 weeks P-C. At least 20 birds were bled each week for each group. Both a commercial IBV ELISA (Idexx Inc.) and an in-house HI test were performed using the serum from these birds. ELISAs were conducted using the serum from all of the birds that were bled. HIs were performed using serum from 8 randomly selected birds for each time point that the birds were bled. HIs were performed using Mass, Conn, Ark, and Del 072 IBV antigens.

For BRO-1, ELISA GMTs remained at or below 43 for all time points. ELISA GMTs for BRO-2 were higher, peaking 2 weeks P-C at 1182 and staying around 800 for the remainder of the experiment. The ELISA GMTs for BRO-3 also peaked 2 weeks P-C at 850 and then declined to 473 by 4 weeks P-C. The HI GMTs for all four serotypes for BRO-1 and BRO-2 were consistently below 30 for all time points over the 4 week P-C time period with occasional individual birds with a titer of up to 128. Starting 2 weeks P-C, the BRO-3 Mass HI GMTs were 1024. They remained at this level out to the last measured time point of 4 weeks P-C. The BRO-3 HI GMTs for the remaining serotypes were below 40.

SPF Clinical Signs and Necropsy Findings. A moderate conjunctivitis was noted in many of the birds in SPF-1 and SPF-2 up to approximately one week of age. This conjunctivitis was attributed to high ammonia levels in the isolation units due to leaking drinkers and improper ventilation. These issues were addressed and the conjunctivitis resolved in all birds prior to challenge. Approximately three days following challenge, the birds in SPF-2 and SPF-3 exhibited a mild conjunctivitis that persisted until two weeks P-C. There was no mortality in any of the groups throughout the length of the experiment. The birds in SPF-2 exhibited flushing at the final 4 week P-C necropsy session. Clinical signs and necropsy findings for SPF birds is shown in Table 9.

TABLE 9

Clinical signs and necropsy findings for SPF birds.

| Week | Group | Conjunctivitis | Tracheitis | Airsacculitis |
|---|---|---|---|---|
| 2.5 | SPF-1 | | | |
| | SPF-2 | 2/2 | | |
| | SPF-3 | 2/2 | 1/2 | |
| 3.2 | SPF-1 | | | |
| | SPF-2 | 1/2 | | 1/2 |
| | SPF-3 | 1/2 | | 2/2 |
| 3.6 | SPF-1 | | | |
| | SPF-2 | | | |
| | SPF-3 | 1/2 | | 1/2 |
| 4.3 | SPF-1 | | | |
| | SPF-2 | | | 1/2 |
| | SPF-3 | | | 1/2 |
| 4.7 | SPF-1 | | | |
| | SPF-2 | | | 1/2 |
| | SPF-3 | | | |
| 5.4 | SPF-1 | | | |
| | SPF-2 | | | |
| | SPF-3 | | | 1/2 |
| 6.1 | SPF-1 | | | |
| | SPF-2 | | | 1/13 |
| | SPF-3 | | | 3/13 |

As with the broilers, the most consistent finding throughout the necropsies was an airsacculitis that also first appeared around 8 days P-C in both SPF-2 and SPF-3. The airsacculitis was mild and often consisted of a small amount of "sudsy" exudates. During the 4 day P-C necropsy, a mild tracheitis was noted in one of the Mass-41 challenged birds. No macroscopic kidney lesions were observed in any of the birds regardless of challenge.

SPF Serology. Blood was collected from all birds remaining in each group immediately prior to challenge, 2 weeks P-C, 3 weeks P-C, and 4 weeks P-C. At least 20 birds were bled each week for each group. Both a commercial IBV ELISA (Idexx Inc.) and an in-house HI test were performed using the serum from these birds. ELISAs were conducted using the serum from all of the birds that were bled. HIs were performed using serum from 8 randomly selected birds for each time point that the birds were bled. HIs were performed using Mass, Conn, Ark, and Del 072 IBV antigens.

Figure 4:
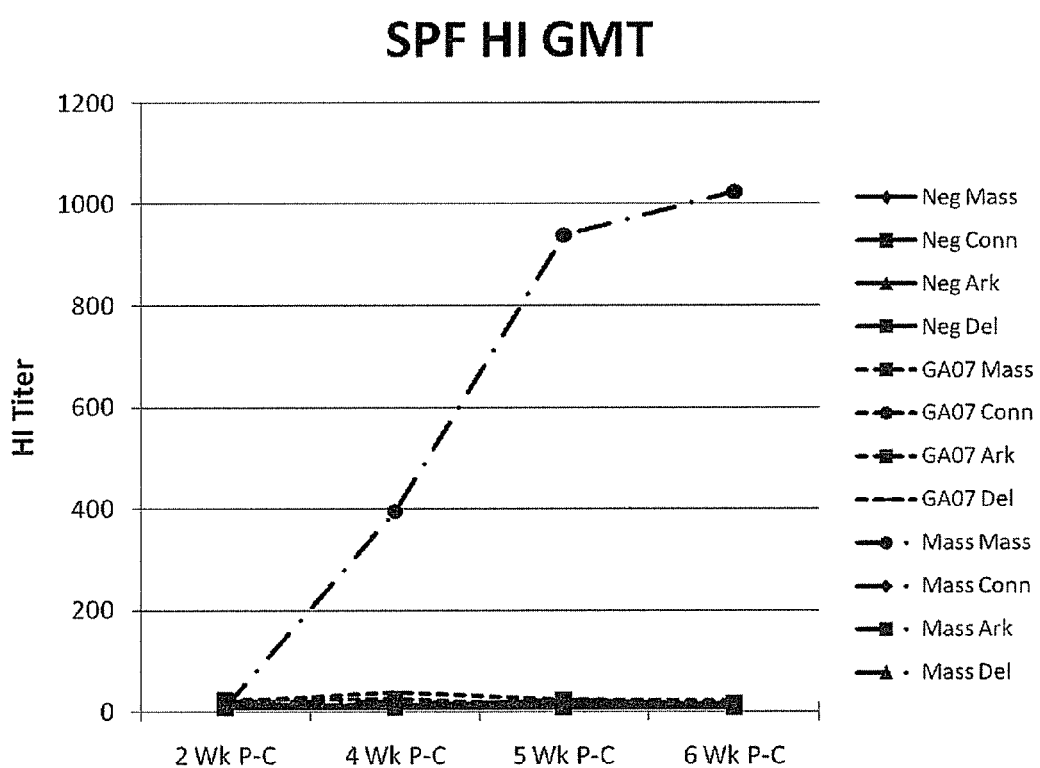
FIG. 4. Geometric mean titers (GMT) from hemagglutination inhibition tests (HI) of SPF-layer type chickens.

For SPF-1, ELISA GMTs were 0 for all time points. ELISA GMTs for SPF-2 at 2 weeks P-C were 361, 263 at 3 weeks P-C, and 375 at 4 weeks P-C. The ELISA GMTs for SPF-3 peaked 2 weeks P-C at 576 and declined to 271 by 4 weeks P-C. The HI GMTs for all four serotypes for SPF-1 and SPF-2 were consistently below 40 for all time points over the 4 week P-C time period. For SPF-3 the Mass HI GMTs were 395 at 2 weeks P-C, 939 at 3 weeks P-C, and 1024 at 4 weeks P-C. The SPF-3 Ark, Conn, and Del 072 HI GMTs for all time points were below 25. This is shown in FIG. 4.

Histopathology. Microscopic results for the trachea reveals SPF-1 (negative control) birds averaged a lesion score of 1 (normal) for sampling time periods day 4 PC to day 24 PC. Day 28 PC averaged a lesion score of 1.5 (one section with 2 foci of mild lymphocytic infiltrates in the lamina propria). The SPF-2 group had occasional deciliation of respiratory epithelial cells, respiratory epithelial cell hyperplasia, mild goblet cell hyperplasia and multifocal, mild to moderate lymphocytic infiltrates in the lamina propria starting day 4 PC until day 12 PC, average score 2. Days 16, 20, and 24 had variable degrees of epithelial cell hyperplasia, the presence of goblet cell hyperplasia or not and focal mild lymphocytic infiltrates in the lamina propria (average score 1.5) Day 28 PC was normal with average score of 1. The SPF-3 group had in days 4 PC and 8 PC diffuse deciliation of the respiratory epithelium, diffuse mild to moderate lymphocytic infiltrates in the lamina propria and occasion bird with respiratory epithelium hyperplasia (average scores 2 for each time period). Days 12 PC to day 28 PC had focal to multifocal mild lymphocytic infiltrates in the lamina propria in the half of the samples (5/10) with average scores 2 (day 12 & 28) and 1.5 (days 16-24).

Microscopic tracheal results for BRO-1 (negative control) birds reveals the majority of samples (9/14) have focal to multifocal mild lymphocytic infiltrates in the lamina propria with an average score ranging from 1.5-2 regardless of time point. Only day 8 PC had no microscopic changes present (score 1). The BRO-2 group had multifocal to diffuse, mild lymphocytic infiltrates in the lamina propria at all time periods. Days 4 PC and 8 PC had multifocal deciliation of the respiratory epitehelium while days 24 and 28 had goblet cell hyperplasia. Average score was 2 for all time periods. The BRO-3 group had similar lymphocytic results as BRO-2 at all time periods. Days 4 PC and 8 PC had diffuse deciliation of the respiratory epithelium while day 12 PC and 20 PC had goblet cell hyperplasia and day 24 PC and 28 PC had mild amounts of excess mucin in the lumen. Average score at all time periods, was 2.

Microscopic results for the kidneys revealed that the SPF-1 group had focal mild mononuclear infiltrates in the interstitium in 1 out of the 2 samples submitted on days 4, 12, 16, 24 and 28 post challenge. No microscopic changes were noted in the glomeruli or medullary cones at any time period. In the SPF-2 group 7 out of 14 samples had mild to severe, focal mononuclear infiltrates in the interstitium at all time periods except Day 20 PC which had none. Multifocal proximal tubular degeneration characterized by vacuoles in the cytoplasm and hypereosinophilia occurred at day 16 PC and 28 PC. Mild lymphocytic infiltrates in some medullary cones occurred at day 12 PC and 16 PC. No glomerular changes were noted at any time period. In the SPF-3 group, focal severe mononuclear infiltrates in the interstitium were seen at days 4, 8 and 16 post challenge. Scattered proximal tubular degeneration occurred at days 16 PC and 20 PC. No microscopic changes were noted in the glomeruli or medullary cones at any time period. In the BRO-1 group, there were focal moderate mononuclear infiltrates in the interstitium of one section at days 4, 8, and 12 post challenge and severe focal mononuclear infiltrates in one section at day 24 PC. Remaining sections and days 16 and 28 had none.

There were no microscopic lesions in the proximal tubules, glomeruli or medullary cones at any time period. In the BRO-2 group, all time periods had multifocal mononuclear infiltrates ranging from mild to severe in the interstitium. Days 16, 24 and 28 post challenge had germinal center formation in the interstitium, in addition to the mononuclear infiltrates. Day 8 PC had one section with multiple areas of mild proximal tubular degeneration present. Day 4 PC had one section with a few glomeruli with fibrin in the glomerular loops and day 8 PC had rare glomeruli with similar fibrin deposition. Remaining time periods had no glomerular changes. Medullary cone lesions ranged from moderate amounts of edema in the interstitium between tubules and collecting ducts of one cone (day 4 PC) (photo 1) to severe lymphocytic infiltrates in multiple cones on day 28 PC (photo 2). Day 12 PC and day 20 PC had no medullary cone lesions. In the BRO-3 group, days 4 PC and day 8 PC had both sections with focal moderate mononuclear infiltrates in the interstitium. Day 12 PC had multifocal mild mononuclear infiltrates in the interstitium in both sections. Day 20 PC had 2 foci of mild mononuclear infiltrates in the interstitium while days 23 PC and 28 PC had focal mild mononuclear infiltrates in the interstitium. Day 16 had no in filtrates in the interstitium. There were no changes in the proximal tubules or ductules, glomeruli or medullary cones at all time periods. Microscopic results for the intestines revealed the presence or absence of gut associated lymphoid tissue in all time periods, regardless of treatment or SPF or BRO status.

Discussion:

Tracheal scores did not differ significantly between all treatment groups regardless of status of breed. However, the amount of inflammation varied greatly. SPF-2 birds typically had a focal area of lymphocytic infiltrates in the lamina propria while the SPF-3 birds tended to have multifocal to diffuse lymphocytic infiltrates. Goblet cell proliferation and respiratory epithelium hyperplasia were more prevalent in the SPF-2 group than the SPF-3 group. The broiler groups BRO-2 and 3 were more similar to each other in terms of lesion scores (2 versus 2) and amount of inflammation present. However, the control group BRO-1 also had numerous samples with multifocal mild lymphocytic infiltrates in the lamina propria (9/14 sections). Because no virus was isolated from the control groups, the inflammatory infiltrates are most likely the result of antigenic stimulation from the dust and feather dander in the isolation units.

Kidney lesions were much more pronounced in the BRO-2 group than any other group with both edema and lymphocytic infiltrates in the interstitium of the medullary cones. This group also had fibrin in the glomerular loops in 2 time periods. The lesions were most similar to field cases submitted to PDRC diagnostic laboratory with a history of flushing. The amounts of mononuclear infiltrates were also increased in the SPF2 and BRO-2 groups as compared to the SPF-3 and BRO-3 respectively. Vaccination with IBV often results in mild mononuclear infiltrates in the interstitium of the kidney. The Mass-41 vaccinated groups had mild lymphocytic infiltrates in the interstitium in both the SPF birds and BRO birds as expected. However, the control groups for both types of chickens had mild to moderate, focal mononuclear infiltrates in the interstitium and no IBV virus was isolated. The presence of some lymphoid aggregates in the interstitium can be considered normal. This does hinder direct comparisons to the control birds with some lymphoid aggregates and vaccinated birds with some lymphoid aggregates. The kidney lesions in this experiment do not include necrosis of the tubules which has been documented with other nephropathogenic strains from Australia.

Example 9

Molecular Characterization of GA07

Figures 5, 5C:
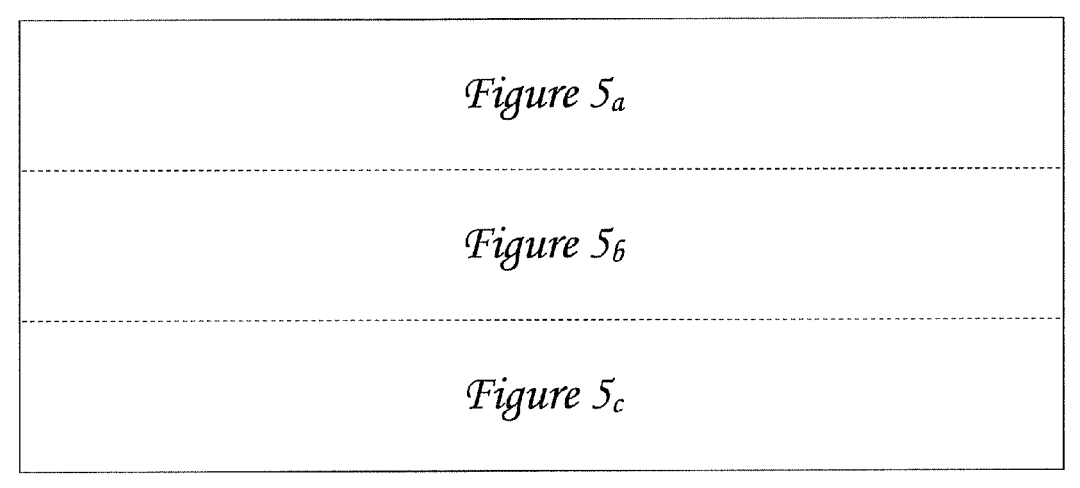

The S1 subunit of the spike gene for the pathogenic GA07 was sequenced. The nucleotide (SEQ ID NO:9) and amino acid sequences (SEQ ID NO:10) for the GA07 pathogenic strain are shown in FIG. 5.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims All headings are for the convenience of the reader and should not be used to limit the meaning of the text that follows the heading, unless so specified.

Sequence Listing Free Text

SEQ ID NO:1 Partial nucleotide sequence of the S1 subunit of the spike gene for pathogenic GA07.

SEQ ID NO:2 Partial nucleotide sequence of the S1 subunit of the spike gene for pathogenic GA08.

SEQ ID NO:3 Nucleotide sequence of the S1 subunit of the spike gene for a pathogenic GA08 isolate.

SEQ ID NO:4 Partial amino acid sequence of the S1 subunit of the spike gene for pathogenic GA07.

SEQ ID NO:5 Partial amino acid sequence of the S1 subunit of the spike gene for pathogenic GA08.

SEQ ID NO:6 Amino acid sequence of the S1 subunit of the spike gene for a pathogenic GA08 isolate.

SEQ ID NO:7 Nucleotide sequence of the S1 subunit of the spike gene for the heat attenuated GA08 isolate GA08/HSp16/08.

SEQ ID NO:8 Amino acid sequence of the S1 subunit of the spike gene for the heat attenuated GA08 isolate GA08/HSp16/08.

SEQ ID NO:9 Nucleotide sequence of the S1 subunit of the spike gene for a pathogenic GA07 isolate.

SEQ ID NO:10 Amino acid sequence of the S1 subunit of the spike gene for a pathogenic GA07 isolate.

SEQ ID NO:11 Partial nucleotide sequence of the S1 subunit of the spike gene for the attenuated GA08 isolate E71.

SEQ ID NO:12 Partial amino acid sequence of the S1 subunit of the spike gene for the attenuated GA08 isolate E71.

SEQ ID NO:13-19 Synthetic oligonucleotide primers

What is claimed is:

1. A composition of matter comprising a purified S1 glycoprotein subunit comprising an amino acid sequence having at least 90% sequence identity to SEQ ID NO:12.

2. A composition of matter, wherein the composition of matter is an isolated infectious bronchitis virus (IBV) comprising an S1 glycoprotein subunit comprising an amino acid sequence having at least 90% sequence identity to SEQ ID NO:12.

3. The isolated infectious bronchitis virus (IBV) of claim 2, wherein the virus is the GA07 isolate, or an attenuated variant thereof.

4. The isolated infectious bronchitis virus (IBV) of claim 2, wherein the virus is the GA08 isolate, or an attenuated variant thereof.

5. The isolated infectious bronchitis virus (IBV) of claim 2, wherein the IBV virus is attenuated.

6. The isolated infectious bronchitis virus (IBV) of claim 2, wherein the virus is the E71 attenuated GA08 isolate, GA08/GU301925/08, GA08/pass4/08, GA08/08/08 strain passage 16, GA08/HSp16/08, or GA08 isolate 64513.

7. An isolated polypeptide having at least 90% sequence identity to SEQ ID NO:12.

8. A diagnostic kit comprising one or more isolated polypeptides of claim 7 and an antibody that binds to infectious bronchitis virus (IBV).

9. The composition of matter of claim 1, wherein the purified S1 glycoprotein subunit comprises an amino acid sequence having at least 95% sequence identity to SEQ ID NO:12.

10. The composition of matter of claim 1, wherein the composition is lyophilized.

11. A method comprising introducing a composition comprising the composition of matter of claim 1 into the body of poultry.

12. The method of claim 11 wherein the composition is administered by spraying.

13. The method of claim 11 wherein the composition further comprises other viral material.

14. A method of producing an immune response to an IBV virus in poultry, the method comprising administering a composition of matter of claim 1.

15. The composition of matter of claim 1, wherein the purified S1 glycoprotein subunit comprises the amino acid sequence SEQ ID NO:12.

16. The isolated infectious bronchitis virus (IBV) of claim 2, wherein the virus is the E71 attenuated GA08 isolate.

17. The composition of matter of claim 1, wherein the purified S1 glycoprotein subunit comprises the amino acid sequence SEQ ID NO:5, SEQ ID NO:6, or SEQ ID NO:8.

18. The composition of matter of claim 2, wherein the composition of matter is lyophilized.

19. A diagnostic kit comprising a composition of matter of claim 2.

20. The composition of matter of claim 2, wherein the S1 glycoprotein subunit comprises an amino acid sequence having at least 95% sequence identity to SEQ ID NO:12.

21. The composition of matter of claim 2, wherein the S1 glycoprotein subunit comprises the amino acid sequence SEQ ID NO:12.

22. The composition of matter of claim 2, wherein the S1 glycoprotein subunit comprises the amino acid sequence SEQ ID NO:5, SEQ ID NO:6, or SEQ ID NO:8.

23. The isolated polypeptide of claim 7, the isolated polypeptide having at least 95% sequence identity to SEQ ID NO:12.

24. The isolated polypeptide of claim 7, the isolated polypeptide comprising the amino acid sequence SEQ ID NO:12.

25. The isolated polypeptide of claim 7, the isolated polypeptide comprising the amino acid sequence SEQ ID NO:5, SEQ ID NO:6, or SEQ ID NO:8.

* * * * *